(12) United States Patent
Kim et al.

(10) Patent No.: US 12,295,258 B2
(45) Date of Patent: May 6, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Won Sam Kim, Cheonan-si (KR); Jung Geun Lee, Cheonan-si (KR); Je Woo Lee, Cheonan-si (KR); Sun Hee Lee, Cheonan-si (KR); Soung Yun Mun, Cheonan-si (KR); Jung Wook Lee, Cheonan-si (KR); Hyung Dong Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/814,978

(22) Filed: Aug. 26, 2024

(65) Prior Publication Data

US 2025/0031567 A1    Jan. 23, 2025

Related U.S. Application Data

(63) Continuation-in-part of application No. 18/568,709, filed as application No. PCT/KR2022/009846 on Jul. 7, 2022.

(30) Foreign Application Priority Data

Jul. 21, 2021  (KR) .................. 10-2021-0095920
Aug. 19, 2021  (KR) .................. 10-2021-0109156

(51) Int. Cl.
*H10K 85/60*    (2023.01)
*C07D 307/91*    (2006.01)
(Continued)

(52) U.S. Cl.
CPC ........ *H10K 85/636* (2023.02); *C07D 307/91* (2013.01); *C07D 307/92* (2013.01);
(Continued)

(58) Field of Classification Search
CPC .............. H10K 85/633; H10K 85/636; H10K 85/6574; H10K 85/6576
See application file for complete search history.

(56) References Cited

U.S. PATENT DOCUMENTS

2023/0131749 A1*  4/2023  Jeong .................. H10K 85/636
                                                                257/40
2023/0263050 A1*  8/2023  Lee ...................... C07D 307/91
                                                                257/40
2023/0331689 A1*  10/2023  Lee ...................... H10K 85/633

FOREIGN PATENT DOCUMENTS

CN    111196822 A    5/2020
CN    112266371 A    1/2021
(Continued)

OTHER PUBLICATIONS

Machine-generated English-language translation of CN-113121366-A.*

(Continued)

*Primary Examiner* — Vu A Nguyen

(74) *Attorney, Agent, or Firm* — Vorys, Sater, Seymour and Pease LLP; Mih Suhn Koh

(57) ABSTRACT

Provided is a compound of Formula 1 capable of improving the light-emitting efficiency, stability, and lifespan of an organic electronic element, a composition comprising the same, an organic electronic element using same, and an electronic device thereof.

15 Claims, 2 Drawing Sheets

(51) Int. Cl.
  *C07D 307/92* (2006.01)
  *C07D 333/76* (2006.01)
  *C07D 407/12* (2006.01)
  *C07D 409/04* (2006.01)
  *C07D 409/12* (2006.01)
  *C09K 11/06* (2006.01)
  *H10K 50/12* (2023.01)
  *H10K 50/155* (2023.01)

(52) U.S. Cl.
  CPC ........ *C07D 333/76* (2013.01); *C07D 407/12* (2013.01); *C07D 409/04* (2013.01); *C07D 409/12* (2013.01); *C09K 11/06* (2013.01); *H10K 85/633* (2023.02); *C09K 2211/1007* (2013.01); *C09K 2211/1011* (2013.01); *C09K 2211/1014* (2013.01); *C09K 2211/1022* (2013.01); *H10K 50/12* (2023.02); *H10K 50/155* (2023.02); *H10K 85/622* (2023.02); *H10K 85/626* (2023.02); *H10K 85/6574* (2023.02); *H10K 85/6576* (2023.02)

(56) References Cited

FOREIGN PATENT DOCUMENTS

| CN | 113121366 A | * | 7/2021 | ........... C07C 211/61 |
|----|----|----|----|----|
| KR | 20170138799 A | * | 12/2017 | ........... C07D 307/94 |
| KR | 10-2018-0041607 A | | 4/2018 | |
| KR | 10-2018-0118748 A | | 10/2018 | |
| KR | 102076958 B1 | * | 2/2020 | ........... C07D 307/91 |
| WO | 2021/141356 A1 | | 7/2021 | |
| WO | WO-2021206375 A1 | * | 10/2021 | ........... C07D 493/04 |
| WO | WO-2021261946 A1 | * | 12/2021 | ........... C07D 307/91 |

OTHER PUBLICATIONS

Machine-generated English-language translation of KR-20170138799-A.*

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

The most problematic issues with organic electroluminescent devices are lifespan and efficiency, and as displays become larger in area, these efficiency and lifespan issues must be resolved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to each of the emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value, therefore the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic element are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against Joule heating generated when the device is driven, while delaying penetration of the metal oxide from the anode electrode (ITO), which is one of the causes of shortening the lifespan of the organic electronic element, into the organic layer. The low glass transition temperature of the hole transport layer material has a characteristic that when the device is driven, the uniformity of the surface of the thin film is lowered, which has been reported to have a great influence on the lifespan of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required.

BRIEF DESCRIPTION OF THE INVENTION

Summary

In order to solve the problems of the background art described above, the present invention has revealed a compound having a novel structure, and that when the compound is applied to an organic electronic element, the luminous efficiency, stability and lifespan of the element are greatly improved.

Accordingly, it is an object of the present invention to provide a novel compound, an organic electronic element using the same, and an electronic device thereof.

Technical Solution

The present invention provides a compound represented by Formula 1.

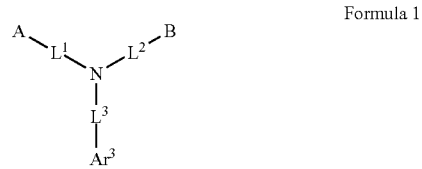

Formula 1

In another aspect, the present invention provides an organic electronic element comprising a compound represented by Formula 1 and an electronic device thereof.

Effects of the Invention

By using the compound according to the present invention, it is possible to achieve a high luminous efficiency, a low driving voltage, and a high heat resistance of the element, and can greatly improve the color purity and lifespan of the element.

Figure 1:
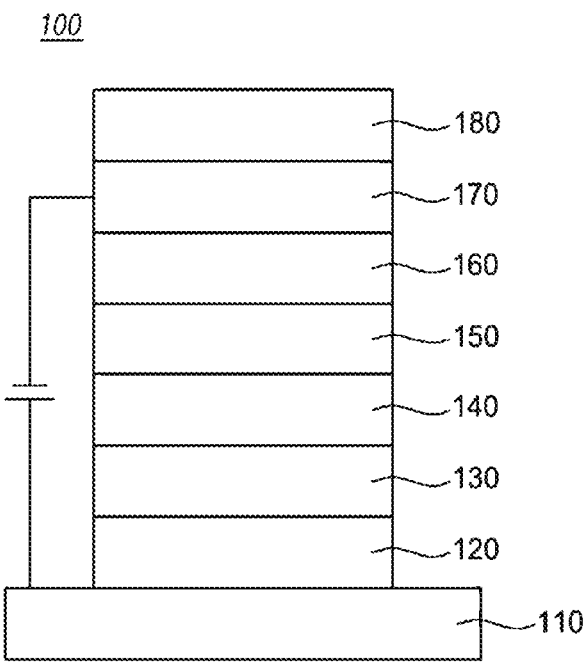
FIG. 1 to FIG. 3 illustrate an example of an organic electronic element according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected ", " coupled" or "connected" between each component.

As used in the specification and the accompanying claims, unless otherwise stated, the following is the meaning of the term as follows.

Unless otherwise stated, the term "halo" or "halogen", as used herein, includes fluorine (F), bromine (Br), chlorine (Cl), or iodine (I).

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes compound below.

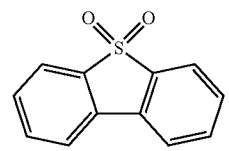 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R'are bonded to each other to form a spiro compound together with the carbon to which they are bonded.

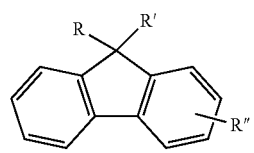

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include one or more heteroatoms, but are not limited thereto.

Unless otherwise stated, the term "substituted or unsubstituted", as used herein, means that substitution is substituted by at least one substituent selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophen group, a $C_6$-$C_{20}$ arylthiophen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited thereto.

Unless otherwise expressly stated, the Formula used in the present invention, as used herein, is applied in the same manner as the substituent definition according to the definition of the exponent of the following Formula.

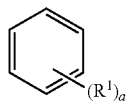

wherein, when a is an integer of 0, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

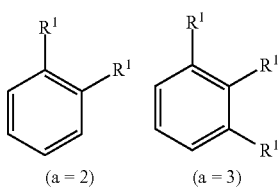

Hereinafter, a compound according to an aspect of the present invention and an organic electronic element comprising the same will be described.

The present invention provides a compound represented by Formula 1:

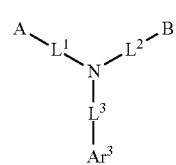

Formula 1

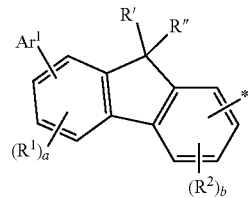

Formula A

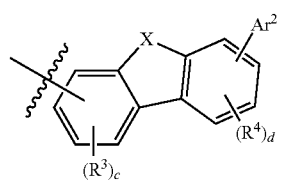

Formula B wherein:
1) A is a substituent represented by Formula A,
2) B is a substituent represented by Formula B,
3) X is O or S,
4) $R^1$, $R^2$, $R^3$ and $R^4$ are each independently the same or different, and each independently selected from the group consisting of a hydrogen; deuterium; halogen; cyano group; nitro group; an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or an adjacent plurality of $R^1$s or of plurality of $R^2$s or of plurality of $R^3$s or of plurality of $R^4$s may be bonded to each other to form a ring, wherein in case $R^1$, $R^2$, $R^3$ and $R^4$ are an aryl group, it may be preferably a $C_6$-$C_{30}$ aryl group, and more preferably a $C_6$-$C_{25}$ aryl group, for example, it may be phenyl, biphenyl, naphthyl, terphenyl, etc., wherein in case $R^1$, $R^2$, $R^3$ and $R^4$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein in case $R^1$, $R^2$, $R^3$ and $R^4$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case $R^1$, $R^2$, $R^3$ and $R^4$ are an alkyl group, it may be preferably a $C_1$-$C_{30}$ alkyl group, and more preferably a $C_1$-$C_{24}$ alkyl group, wherein in case $R^1$, $R^2$, $R^3$ and $R^4$ are an alkenyl group, it may be preferably a $C_2$-$C_{30}$ alkenyl group, and more preferably a $C_2$-$C_{24}$ alkenyl group, wherein in case $R^1$, $R^2$, $R^3$ and $R^4$ are an alkynyl group, it may be preferably a $C_2$-$C_{30}$ alkynyl group, and more preferably a $C_2$-$C_{24}$ alkynyl group, wherein in case $R^1$, $R^2$, $R^3$ and $R^4$ are alkoxy groups, it may be preferably a $C_1$-$C_{30}$ alkoxy group, and more preferably a $C_1$-$C_{24}$ alkoxy group, wherein in case $R^1$, $R^2$, $R^3$ and $R^4$ are an aryloxy group, it may be preferably a $C_6$-$C_{30}$ aryloxy group, and more preferably a $C_6$-$C_{24}$ aryloxy group, 5) R' and R" are each independently selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group; or R' and R" can be bonded to each other to form a spiro, wherein in case R' and R" are an aryl group, it may be preferably a $C_6$-$C_{30}$ aryl group, and more preferably a $C_6$-$C_{25}$ aryl group, for example, it may be phenyl, biphenyl, naphthyl, terphenyl, etc., wherein in case R' and R" are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein in case R' and R" are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

wherein in case R' and R" are an alkyl group, it may be preferably a $C_1$-$C_{30}$ alkyl group, and more preferably a $C_1$-$C_{24}$ alkyl group, wherein in case R' and R" are an alkoxy groups, it may be preferably a $C_1$-$C_{24}$ alkoxy group, wherein in case R' and R" are an aryloxy group, it may be preferably a $C_6$-$C_{24}$ aryloxy group, 6) a, b, c and d are each independently an integer of 0 to 3, 7) $Ar^1$ and $Ar^2$ are each independently selected from the group consisting of a hydrogen; deuterium; an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group, wherein in case $Ar^1$ and $Ar^2$ are an aryl group, it may be preferably a $C_6$-$C_{30}$ aryl group, and more preferably a $C_6$-$C_{25}$ aryl group, for example, it may be phenyl, biphenyl, naphthyl, terphenyl, etc., wherein in case $Ar^1$ and $Ar^2$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein in case $Ar^1$ and $Ar^2$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case $Ar^1$ and $Ar^2$ are an alkyl group, it may be preferably a $C_1$-$C_{30}$ alkyl group, and more preferably a $C_1$-$C_{24}$ alkyl group, wherein in case $Ar^1$ and $Ar^2$ are an alkenyl group, it may be preferably a $C_2$-$C_{30}$ alkenyl group, and more preferably a $C_2$-$C_{24}$ alkenyl group, wherein in case $Ar^1$ and $Ar^2$ are an alkynyl group, it may be preferably a $C_2$-$C_{30}$ alkynyl group, and more preferably a $C_2$-$C_{24}$ alkynyl group, wherein in case $Ar^1$ and $Ar^2$ are alkoxy groups, it may be preferably a $C_1$-$C_{30}$ alkoxy group, and more preferably a $C_1$-$C_{24}$ alkoxy group, wherein in case $Ar^1$ and $Ar^2$ are an aryloxy group, it may be preferably a $C_6$-$C_{30}$ aryloxy group, and more preferably a $C_6$-$C_{24}$ aryloxy group, 8) $Ar^3$ is selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring, wherein in case $Ar^3$ is an aryl group, it may be preferably a $C_6$-$C_{30}$ aryl group, and more preferably a $C_6$-$C_{25}$ aryl group, for example, it may be phenyl, biphenyl, naphthyl, terphenyl, etc., wherein in case $Ar^3$ is a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein in case $Ar^3$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, 9) $L^1$, $L^2$ and $L^3$ are each independently selected from the group consisting of a single bond; a $C_6$-$C_{60}$ arylene group; fluorenylene group; a $C_2$-$C_{60}$ heterocyclic group including at least one heteroatom of O, N, S, Si or P; a $C_3$-$C_{60}$ aliphatic ring, wherein in case $L^1$, $L^2$ and $L^3$ are an arylene group, it may be preferably a $C_6$-$C_{30}$ arylene group, more preferably a $C_6$-$C_{24}$ arylene group, for example, phenylene, biphenylene, naphthylene, terphenylene, etc., wherein in case $L^1$, $L^2$ and $L^3$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein in case $L^1$, $L^2$ and $L^3$ are an aliphatic ring group, it may be preferably a $C_3$-$C_{30}$ aliphatic ring, and more preferably a $C_3$-$C_{24}$ aliphatic ring.

10) * refers to the position to be bonded to $L^1$ of Formula 1, 11) refers to the position to be bonded to $L^2$ of Formula 1, 12) wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_6$-$C_{20}$ aryloxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_1$-$C_{20}$ heteroalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula A is represented by any one of Formulas A-1 to A-4.

Formula A-1

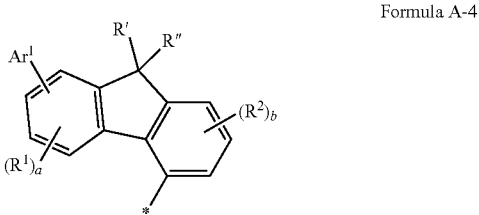

Formula A-2

Formula A-3

Formula A-4 wherein, Ar$^1$, R$^1$, R$^2$, R', R", a, b and * are the same as defined above.

Formula A may be any one of the following compounds.

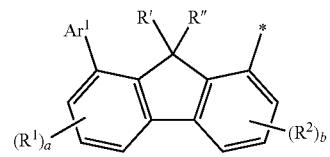

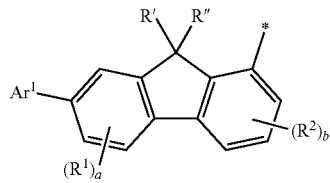

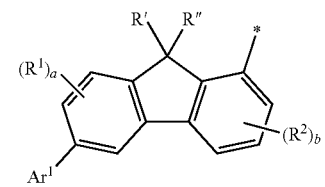

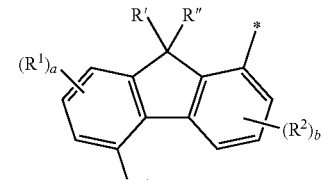

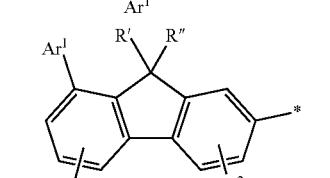

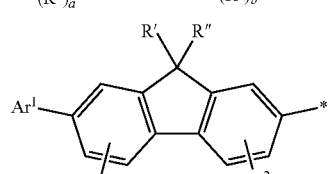

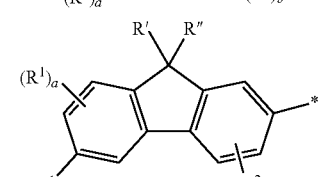

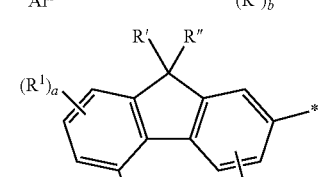

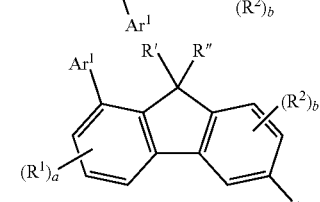

-continued
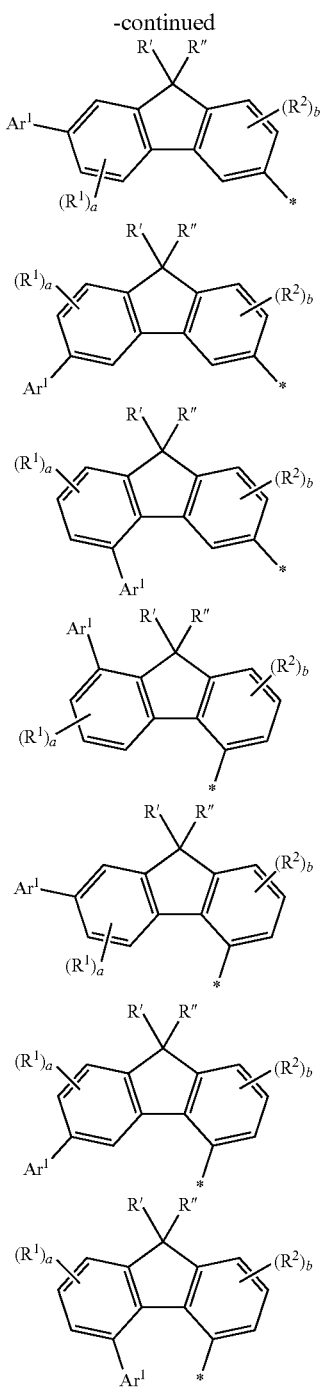
Also, Formula B is represented by any one of the following Formulas B-1 to B-4:
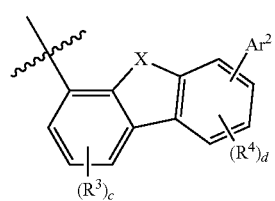
Formula B-1
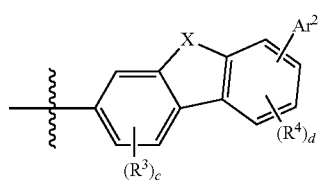
Formula B-2
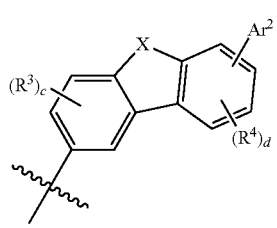
Formula B-3
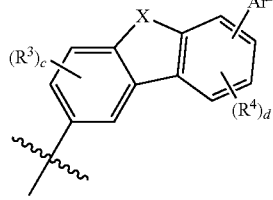
Formula B-4
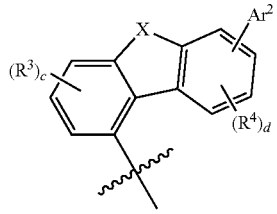
wherein, $Ar^2$, X, $R^3$, $R^4$, c, d and 〰〰 are the same as defined above.
Formula B may be any one of the following compounds.
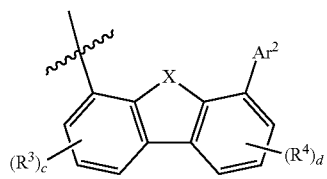
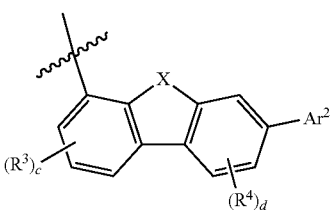
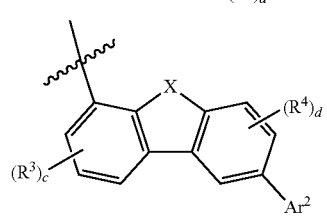
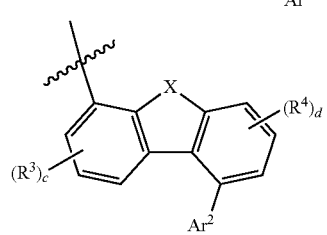

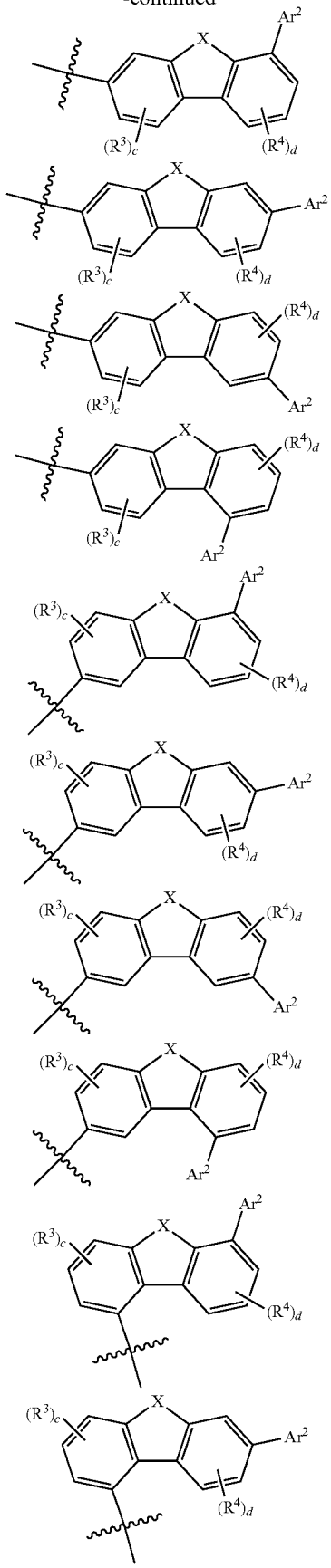
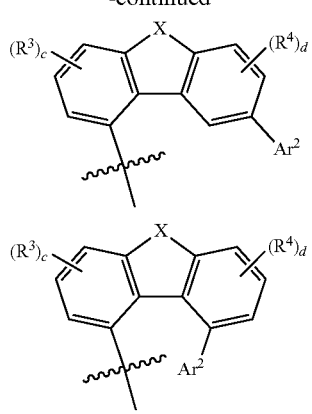
Also, Ar¹ to Ar³ are represented by any one of the following Formulas Ar-1 to Ar-6:
Formula Ar-1
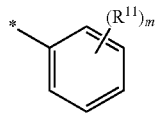
Formula Ar-2
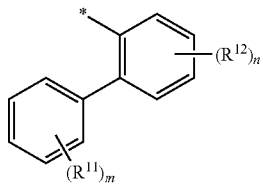
Formula Ar-3
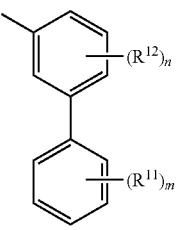
Formula Ar-4
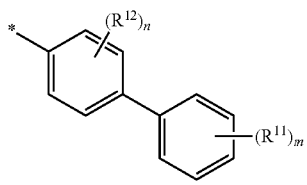
Formula Ar-5
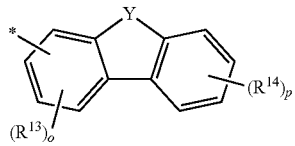
Formula Ar-6
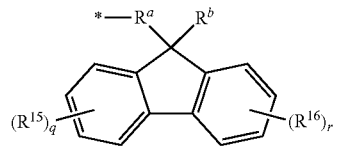

Wherein,
1) * is the position to be bonded to L³ of Formula 1; the position to be bonded to Formula A; or the position to be bonded to Formula B;
2) R¹¹, R¹², R¹³, R¹⁴, R¹⁵ and R¹⁶ are the same as definition of R¹,
3) Y is O, S, CR$^x$R$^y$ or NR$^z$,
4) R$^a$, R$^b$, R$^x$, R$^y$ and R$^z$ are the same as the definition of R', alternatively, R$^a$ and R$^b$ or R$^x$ and R$^y$ can be bonded to each other to form a ring,
5) m is an integer of 0 to 5, n, p, q and r are each independently an integer of 0 to 4, o is an integer of 0 to 3.

Ar¹ to Ar³ may be any one of the following compounds.

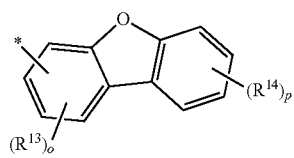

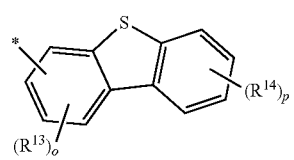

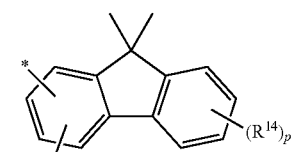

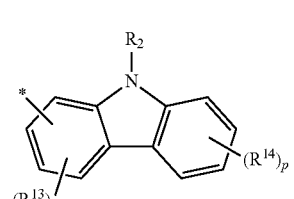

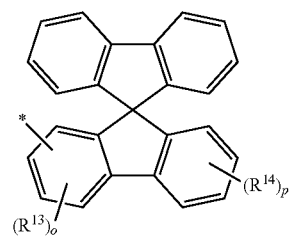

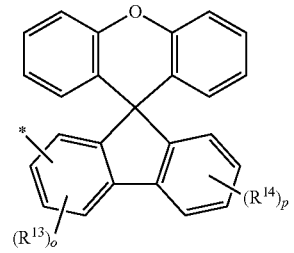

-continued

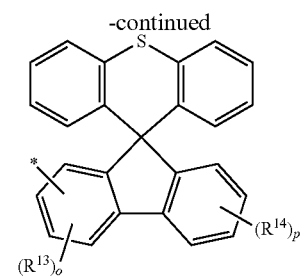

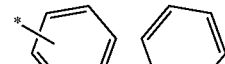

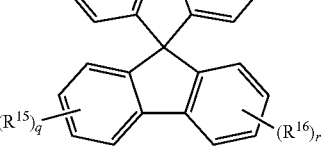

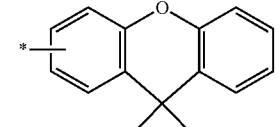

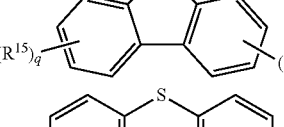

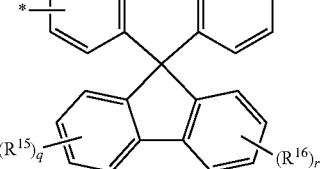

More preferably, Ar¹ to Ar³ may be any one of the following compounds.

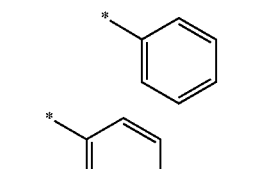

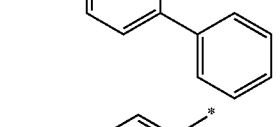

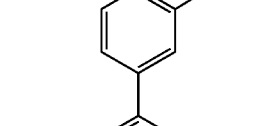

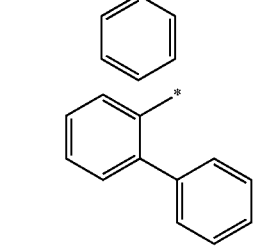

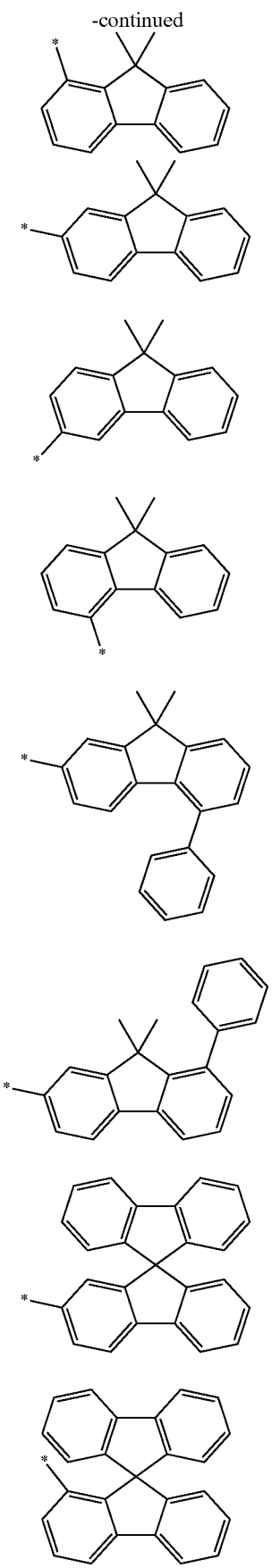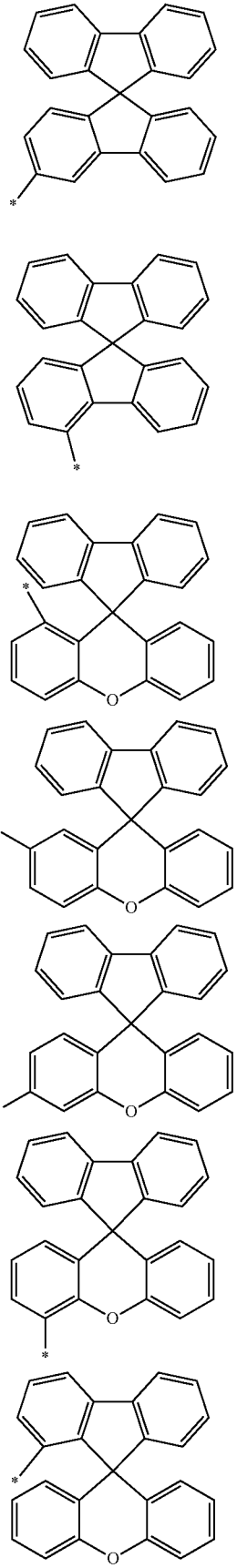

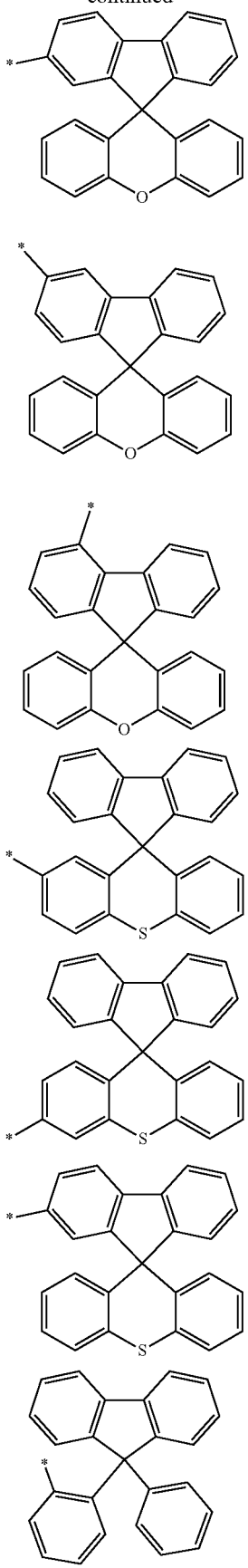
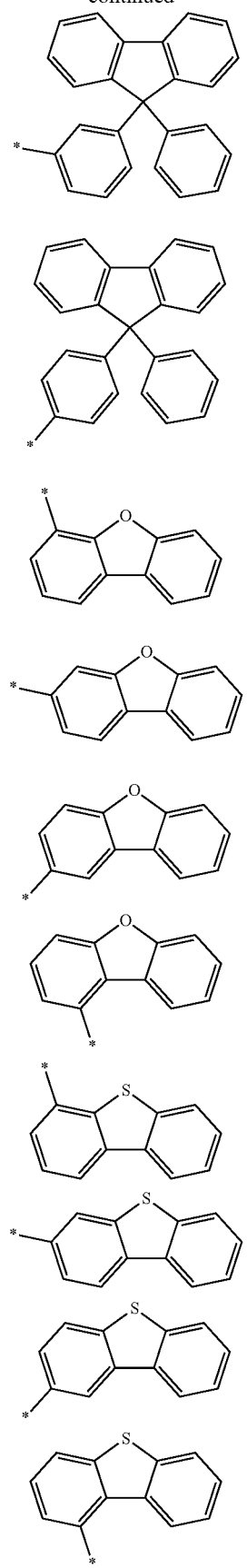

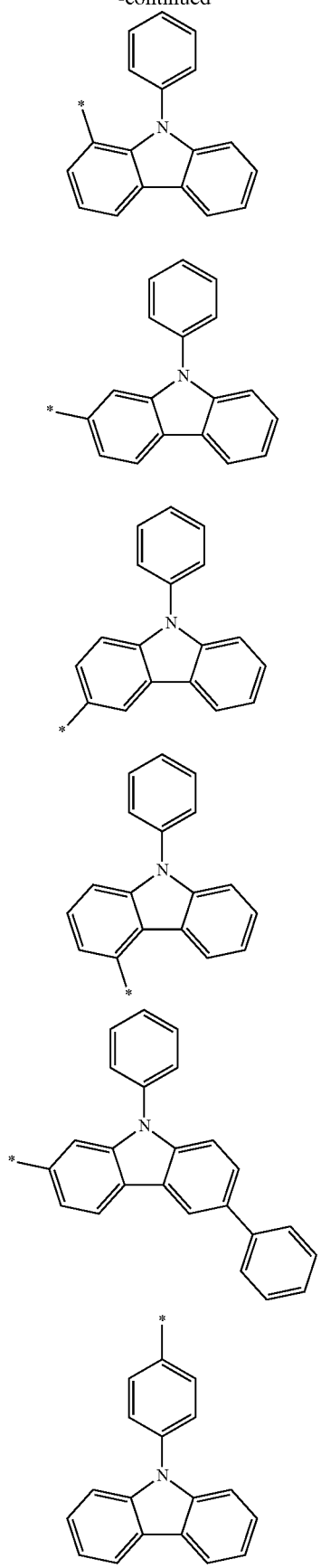
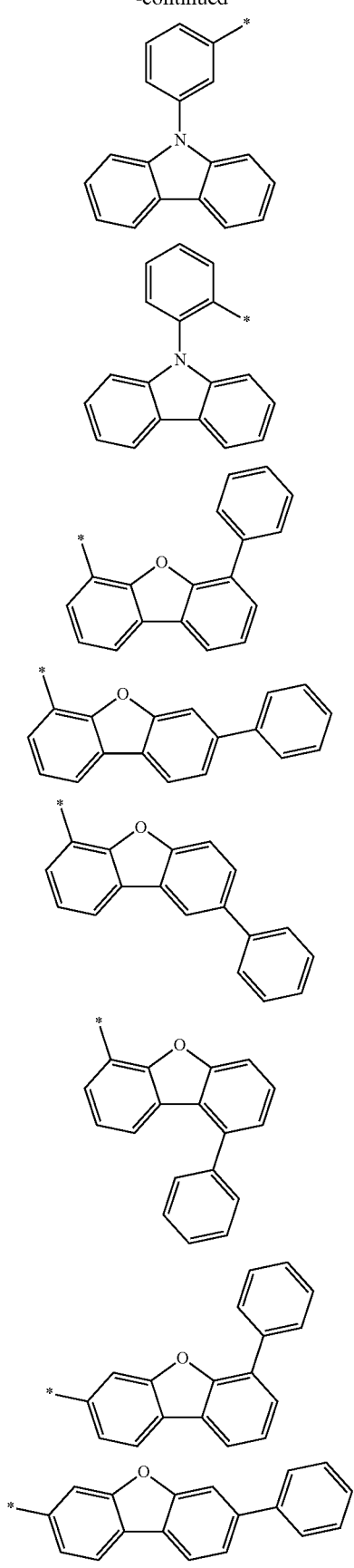

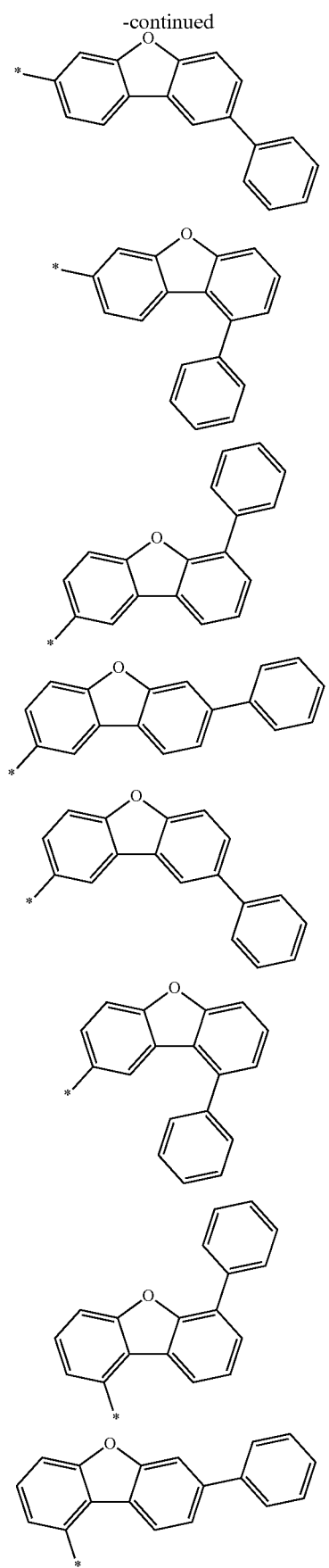
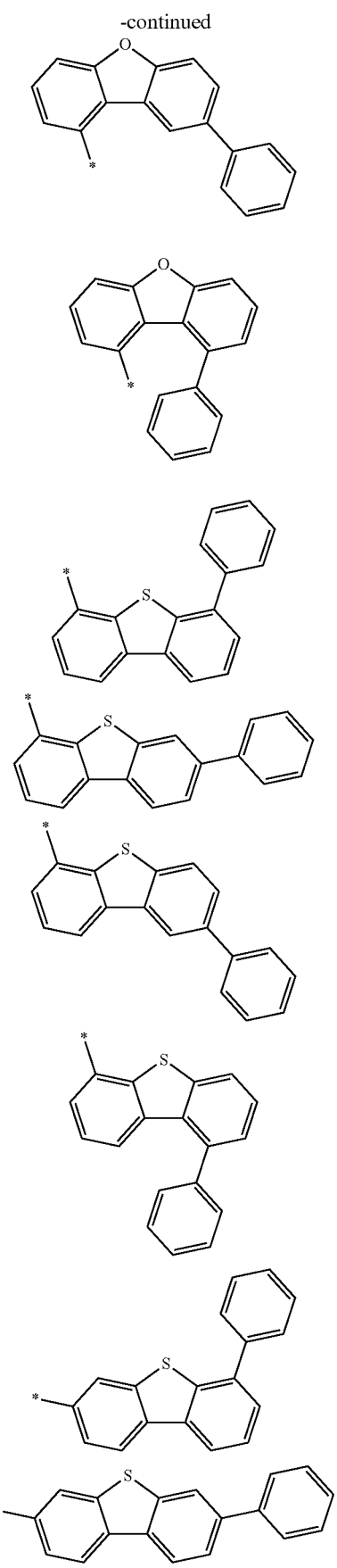

-continued

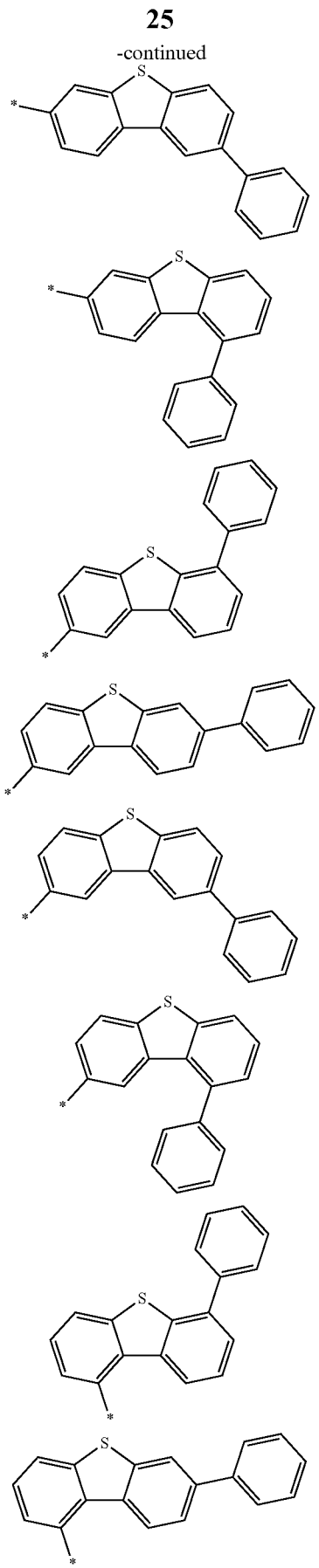

-continued

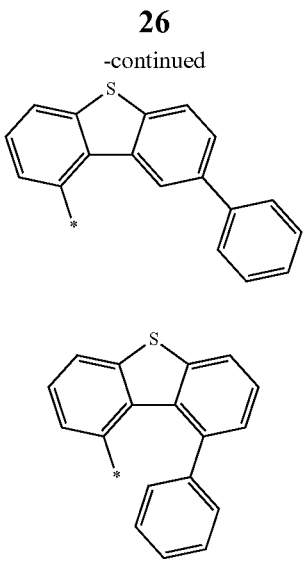

Also, at least one of $L^1$ to $L^3$ is represented by any one of the following Formulas L-1 to L-3.

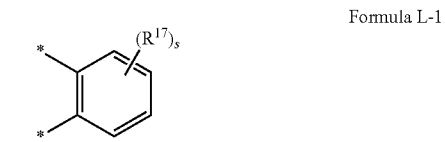
Formula L-1

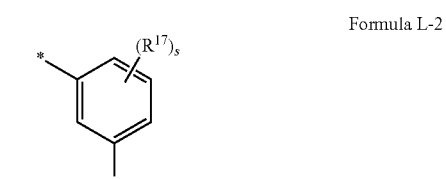
Formula L-2

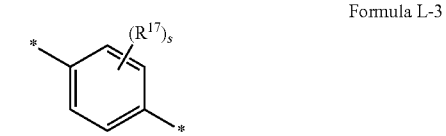
Formula L-3

Wherein:
1) $R^{17}$ is the same as the definition of $R^1$,
2) s is an integer of 0 to 4,
3) * means the position to be bonded.

Additionally, both $L^1$ and $L^2$ are single bonds.

Also, $Ar^1$ and $Ar^2$ are each independently selected from the group consisting of an $C_6$-$C_{16}$ aryl group; a $C_2$-$C_{60}$ heterocyclic group including at least one heteroatom of O, N, S, Si or P; a $C_1$-$C_{60}$ alkyl group;

Also, $Ar^1$ and $Ar^2$ are each independently selected from the group consisting of phenyl group, biphenyl group, naphthyl group, fluorenyl group, methyl group, t-butyl group and $C_3$-$C_{10}$ cycloalkyl group.

Also, $Ar^1$ is a hydrogen, and $Ar^2$ is selected from the group consisting of phenyl group, biphenyl group, naphthyl group, fluorenyl group, methyl group, t-butyl group and $C_3$-$C_{10}$ cycloalkyl group.

Also, Formula 1 is represented by any of the following Formulas 1-1 to 1-8:
Formula 1-1
Formula 1-2
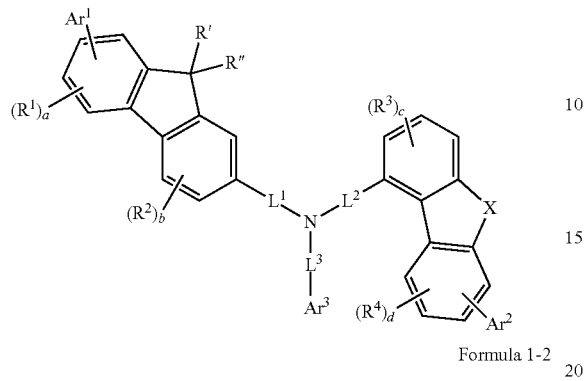
Formula 1-3
Formula 1-4
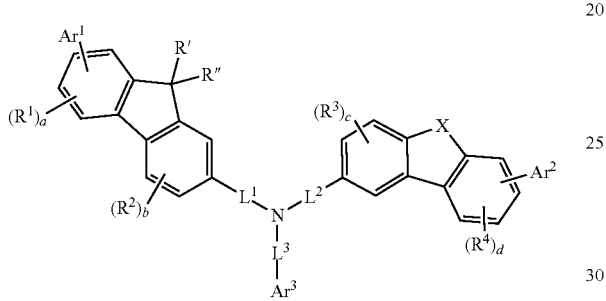
Formula 1-5
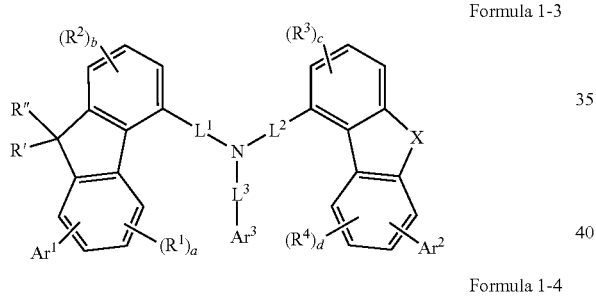
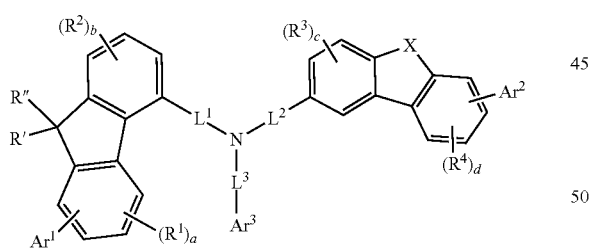
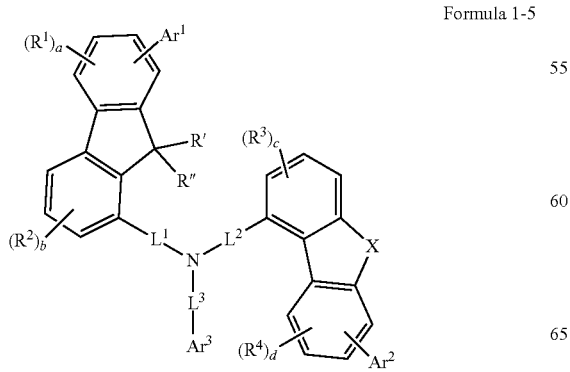
Formula 1-6
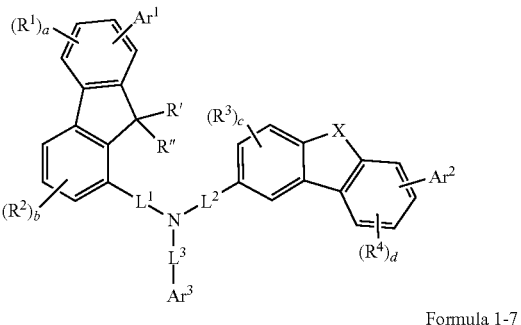
Formula 1-7
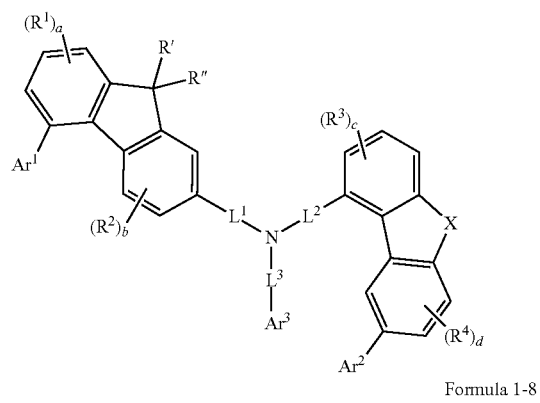
Formula 1-8
wherein, X, $R^1$, $R^2$, $R^3$, $R^4$, R', R", $Ar^1$, $Ar^2$, $Ar^3$, $L^1$, $L^2$, $L^3$, a, b, c and d are the same as defined above.
Preferably, Formula 1 may be represented by Formula 1-9.
Formula 1-9
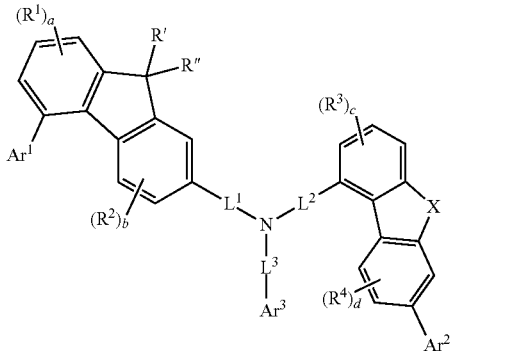

Wherein, X, R¹, R², R³, R⁴, R', R", Ar¹, Ar², Ar³, L¹, L², L³, a, b, c and d are the same as defined above.
Also, the compound represented by Formula 1 is represented by any one of the following compounds P-1 to P-160.
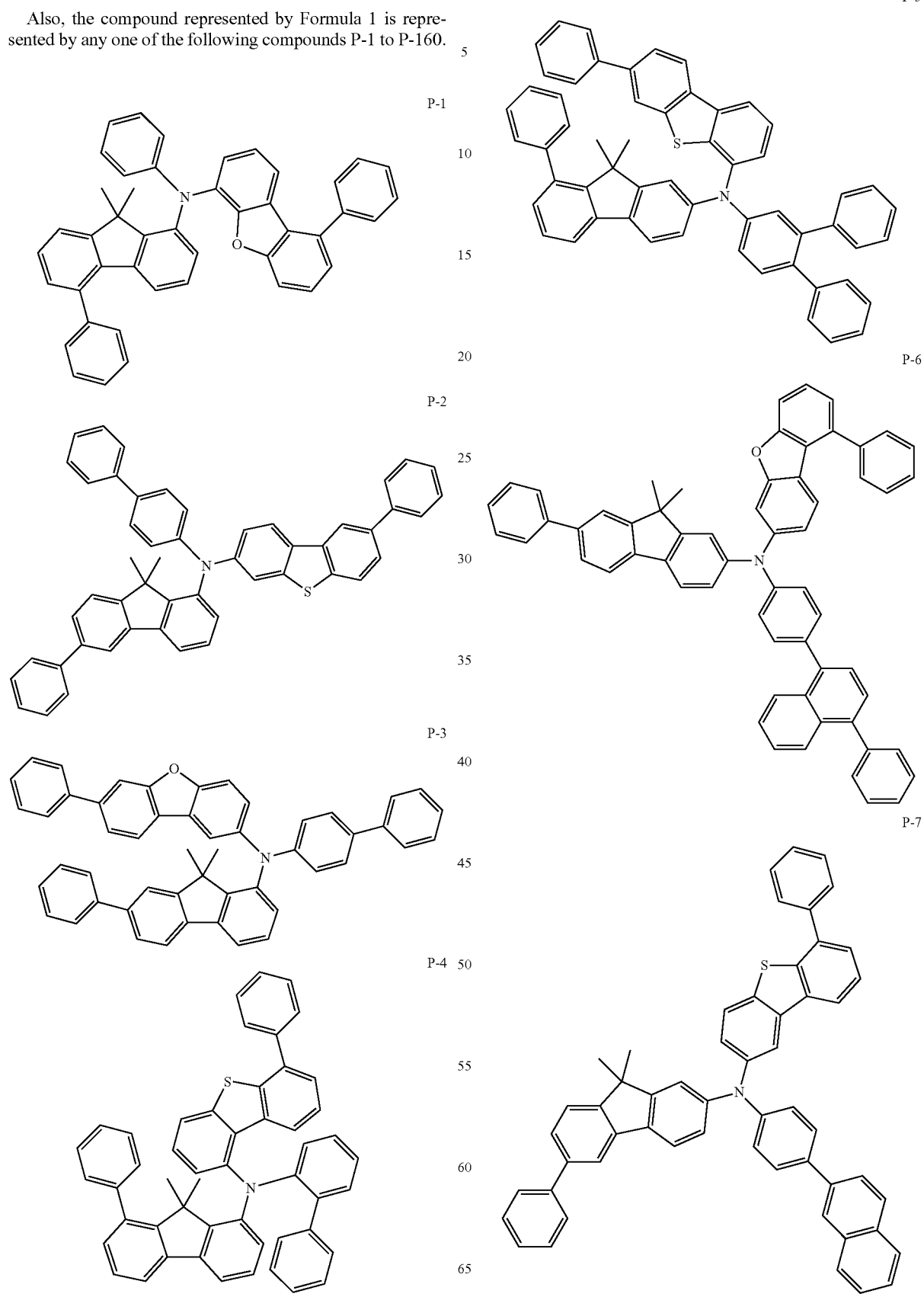

P-8
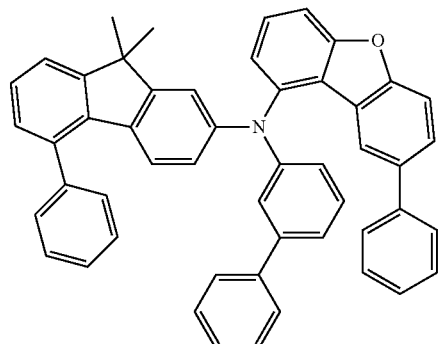
P-11
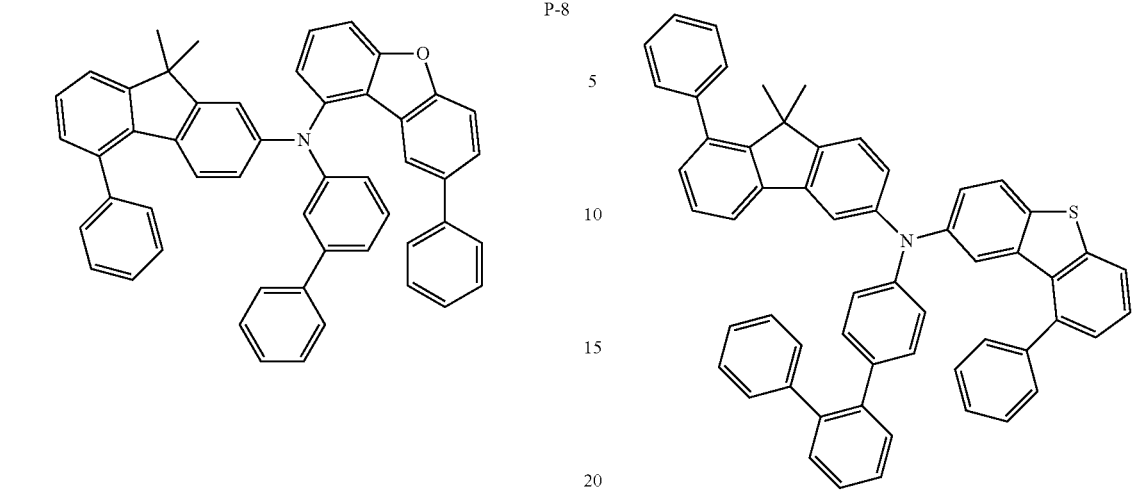
P-9
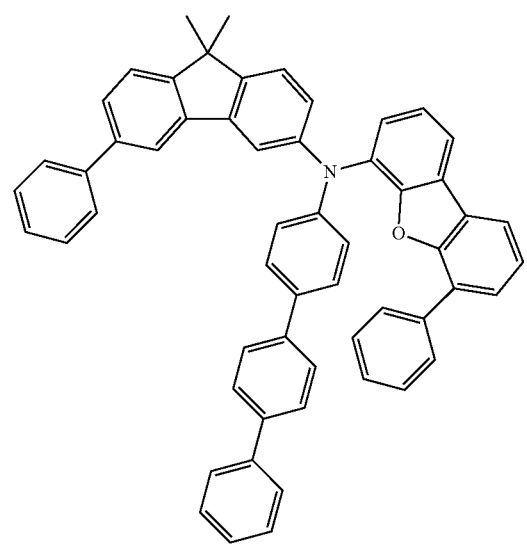
P-12
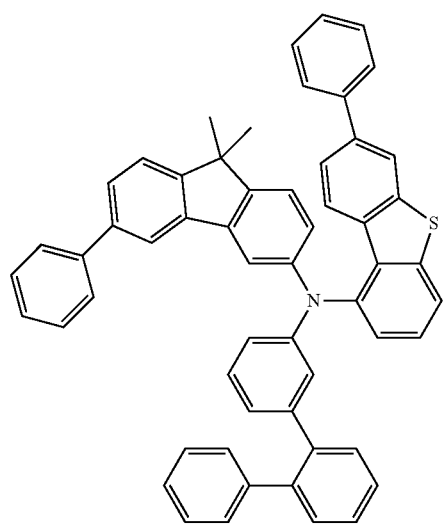
P-13
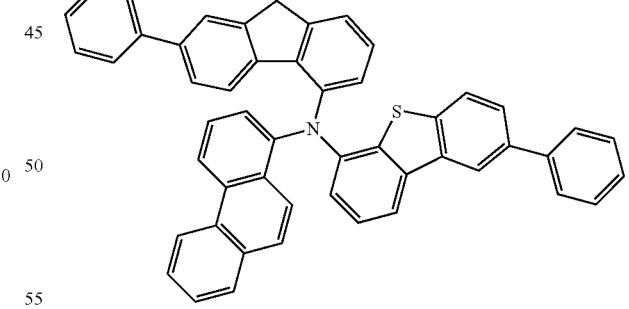
P-10
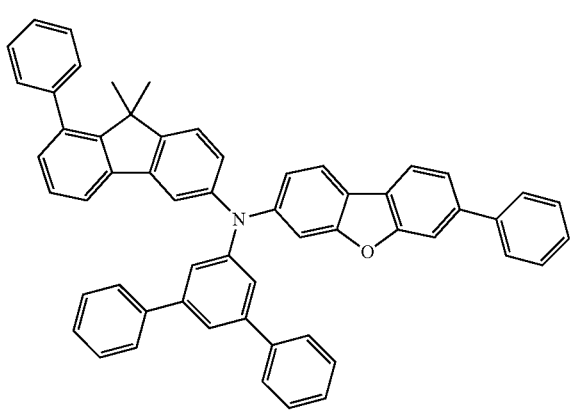
P-14
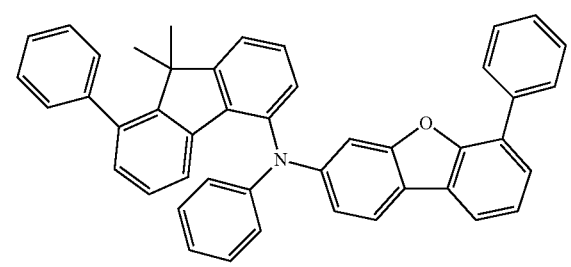

P-15
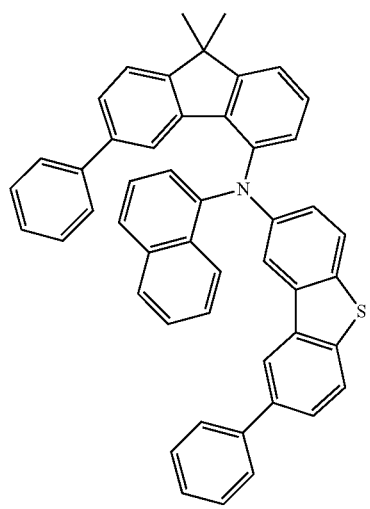
P-16
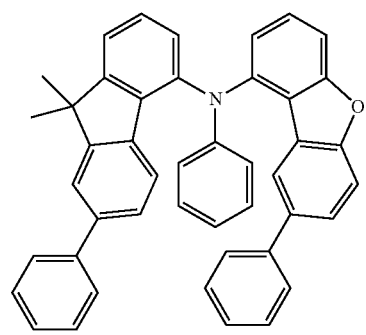
P-17
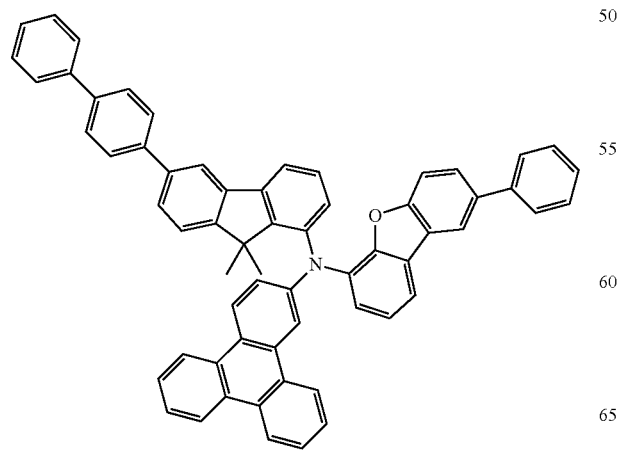
P-18
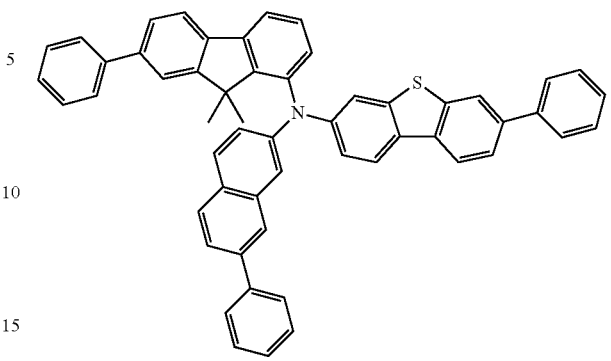
P-19
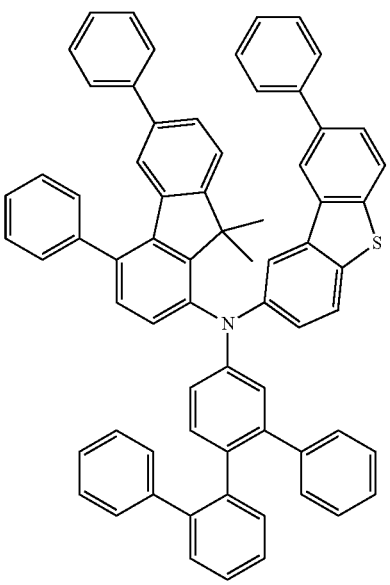
P-20
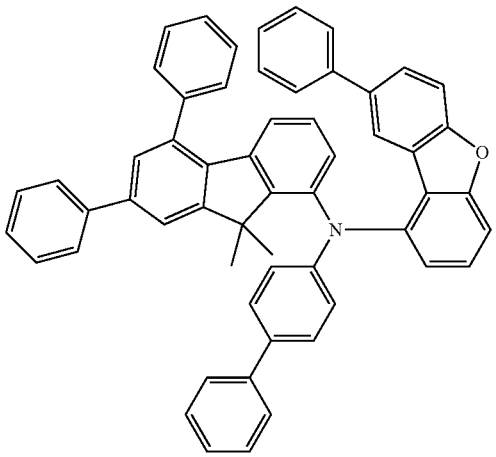

P-21
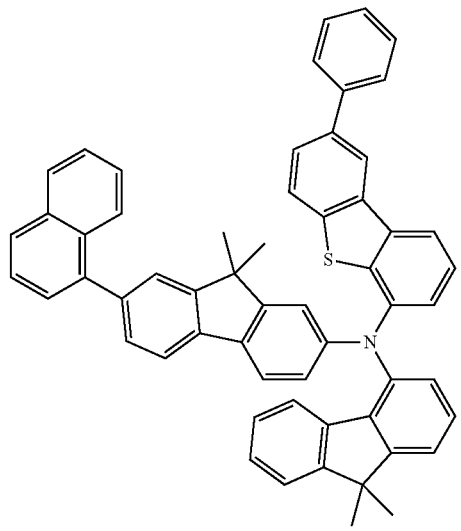
P-22
P-23
P-24
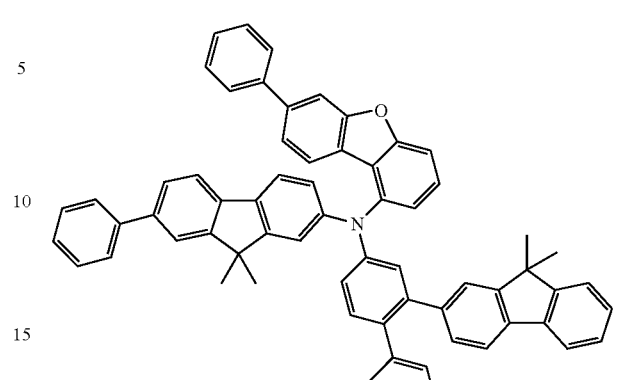
P-25
P-26
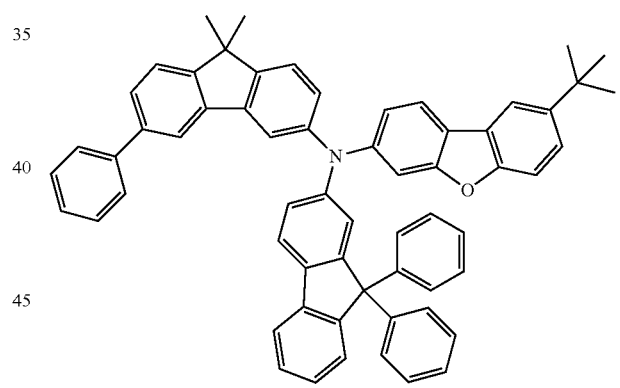
P-27
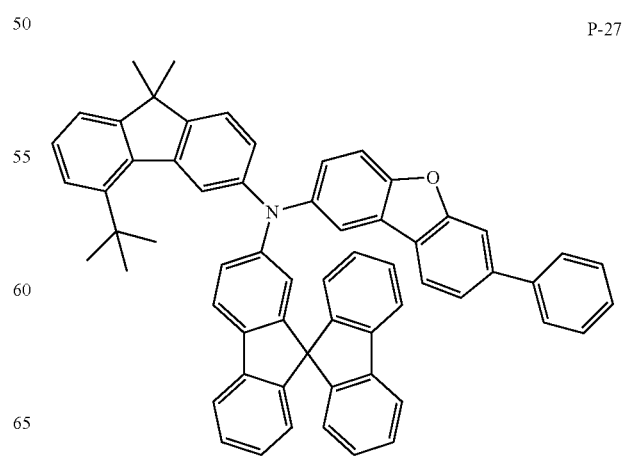

P-28
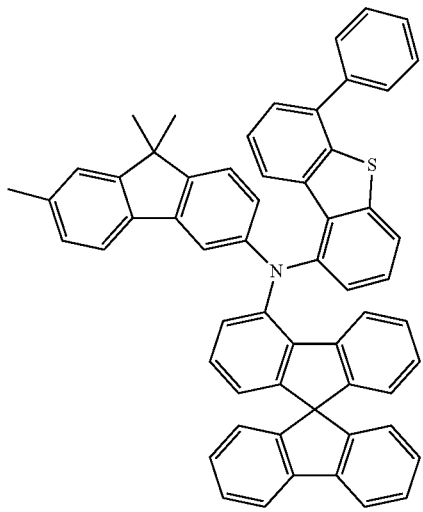
P-31
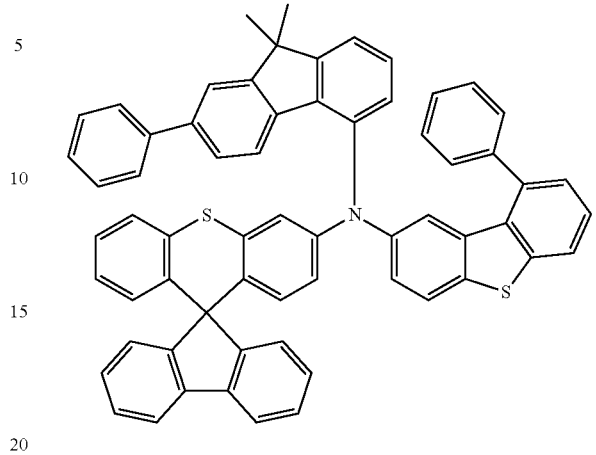
P-29
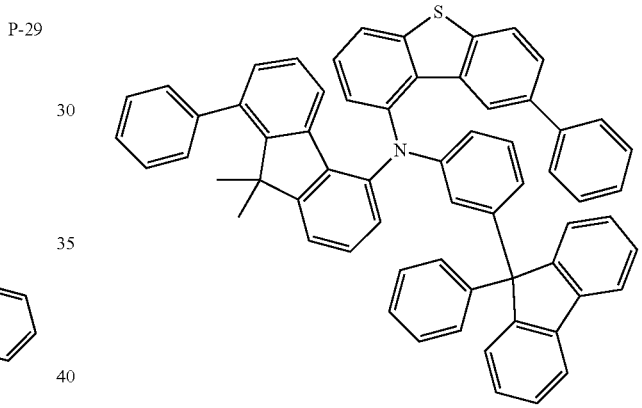
P-32
P-30
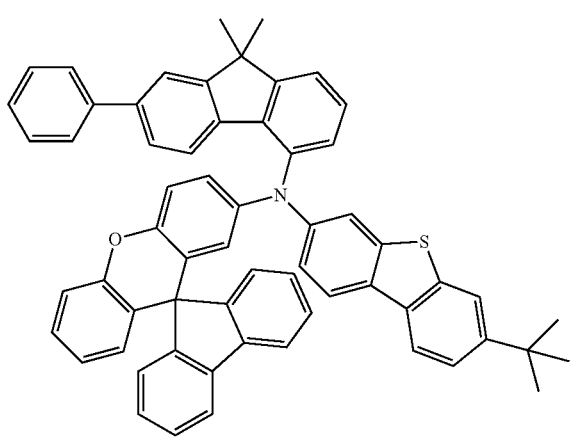
P-33
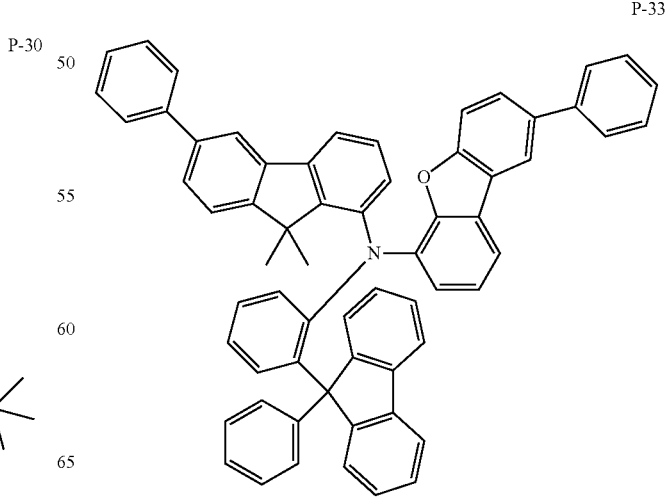

P-34
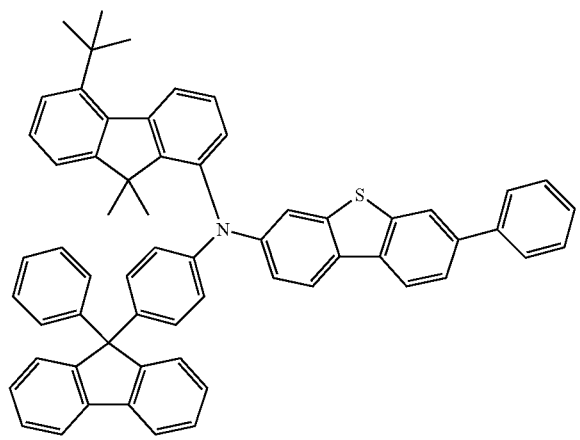
P-35
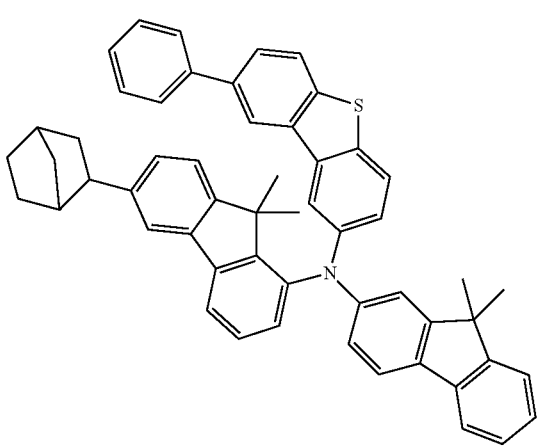
P-36
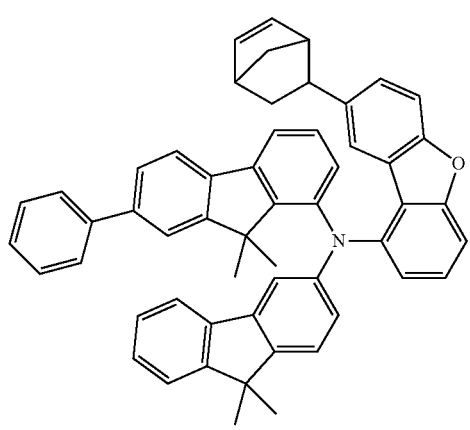
P-37
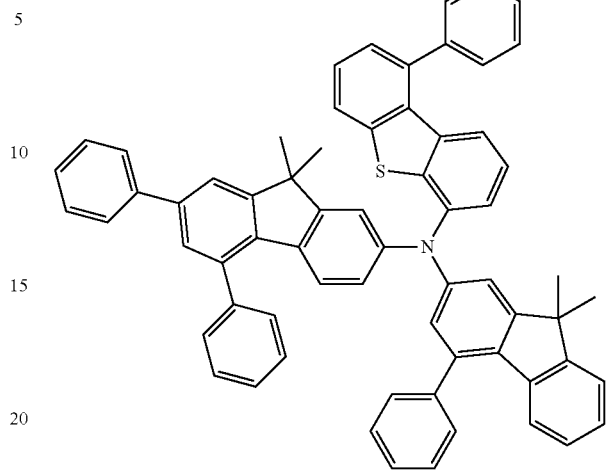
P-38
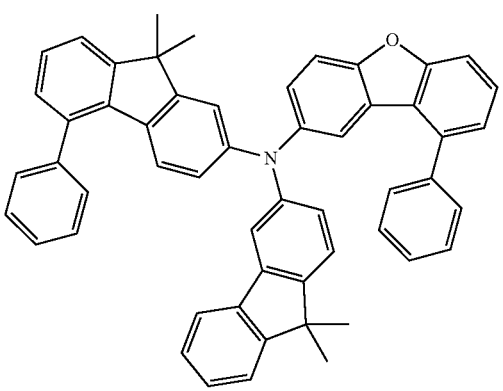
P-39

-continued
P-40
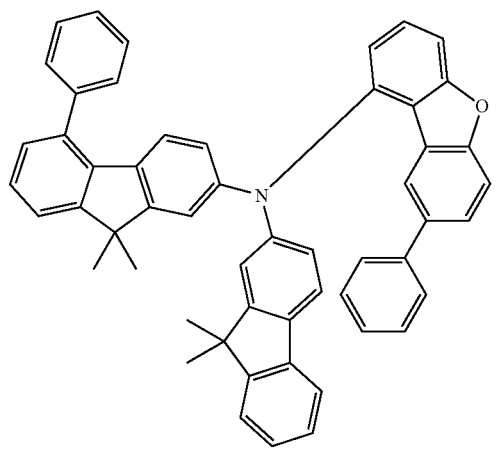
P-44
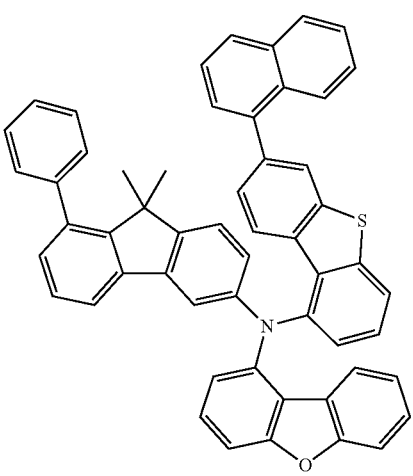
P-41
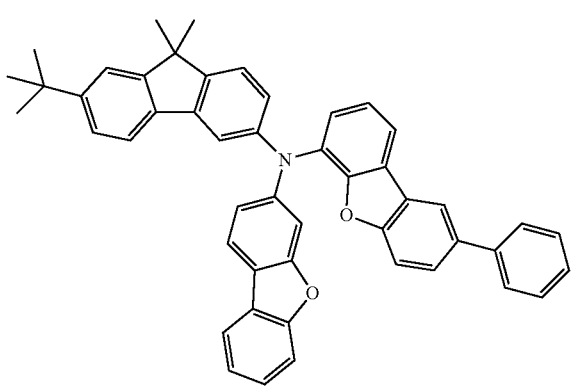
P-45
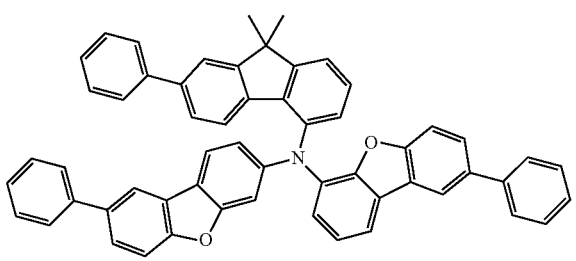
P-42
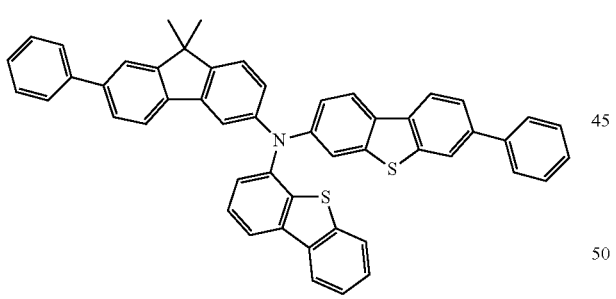
P-43
P-46
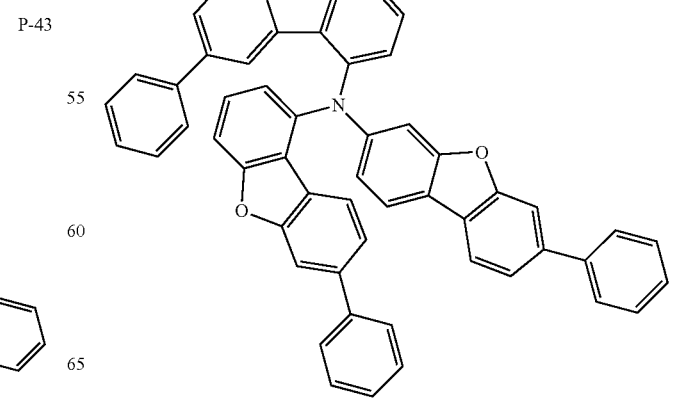

P-47
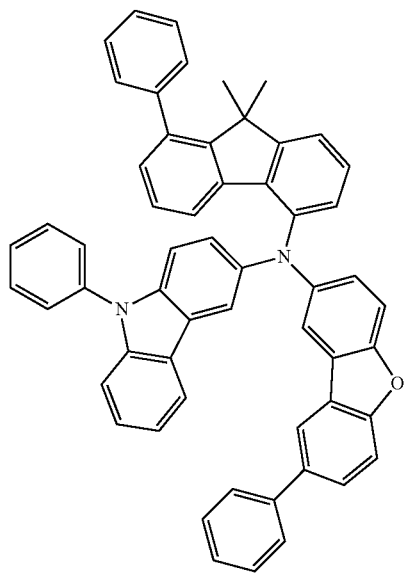
P-50
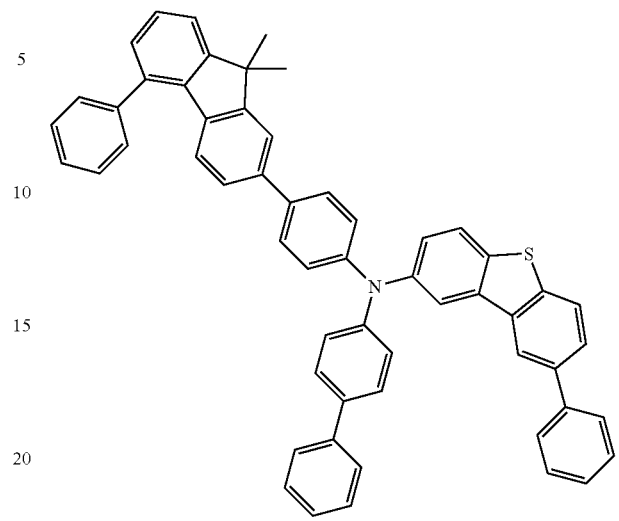
P-48
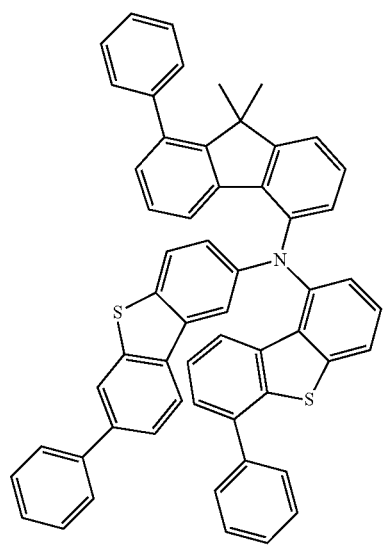
P-51
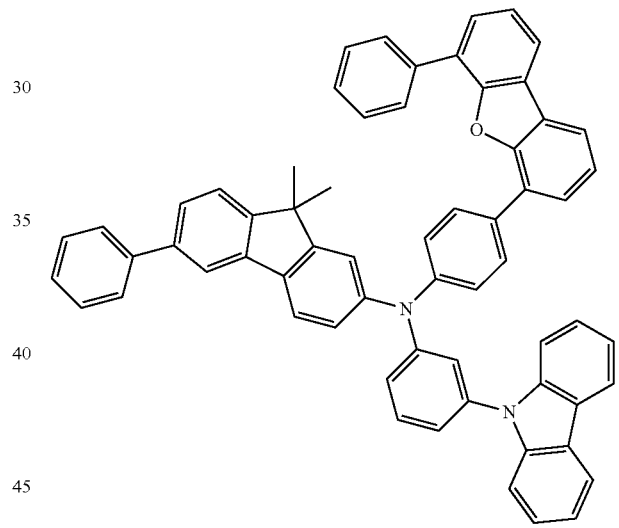
P-49
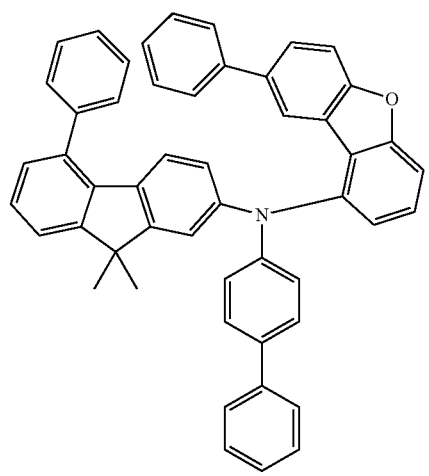
P-52
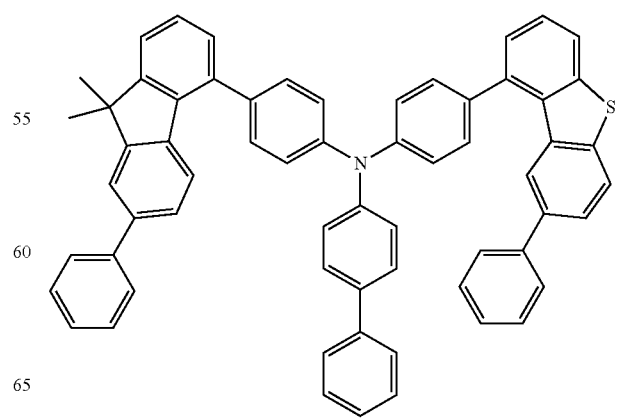

-continued
P-53
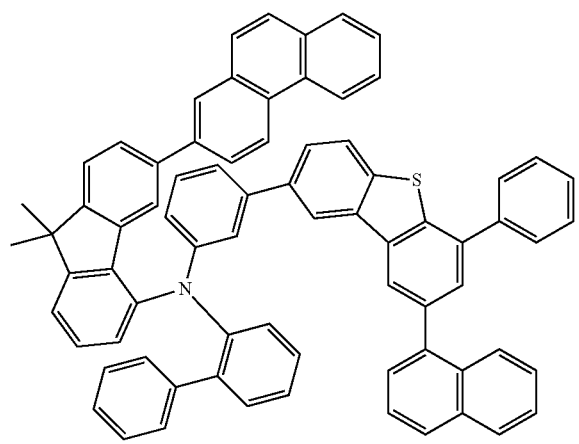
P-54
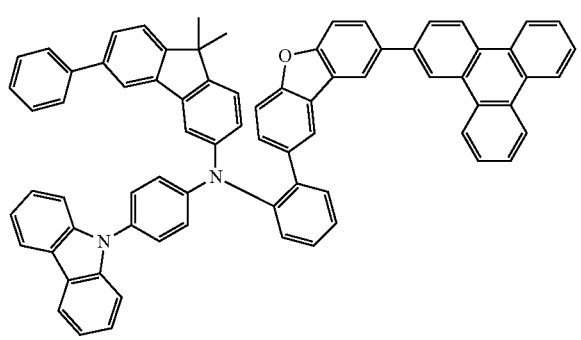
P-55
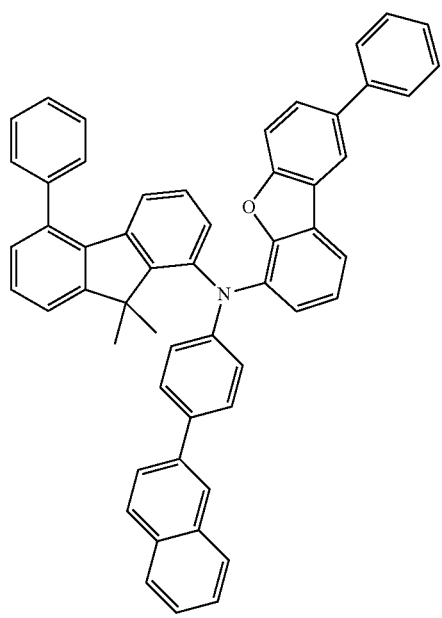
-continued
P-56
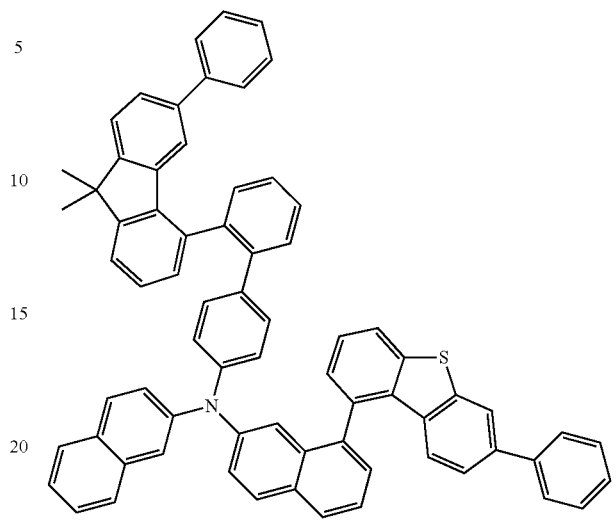
P-57
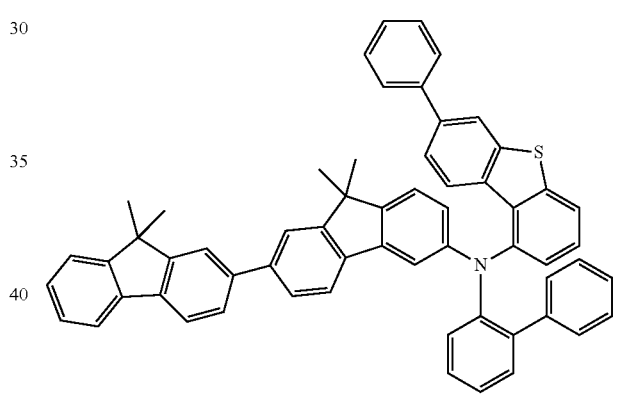
P-58
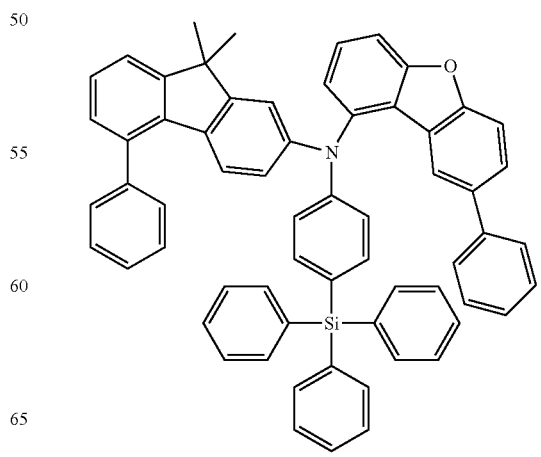

P-59
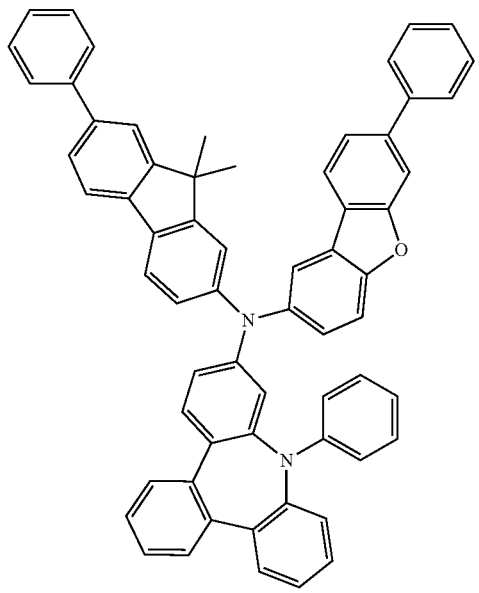
P-62
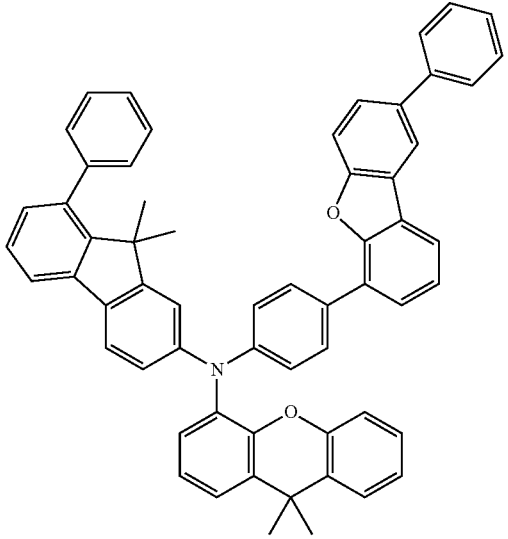
P-60
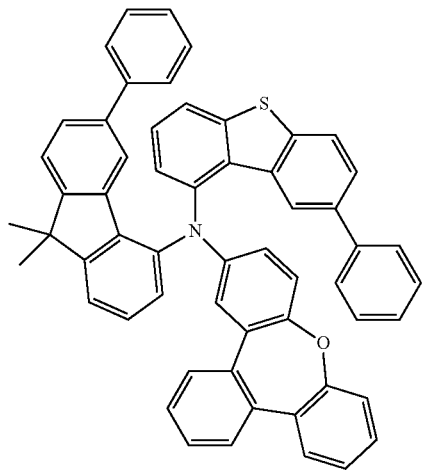
P-63
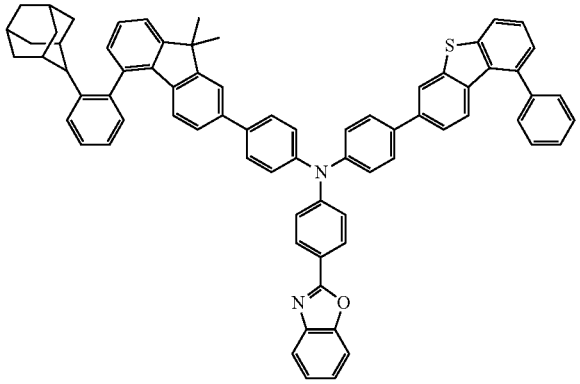
P-61
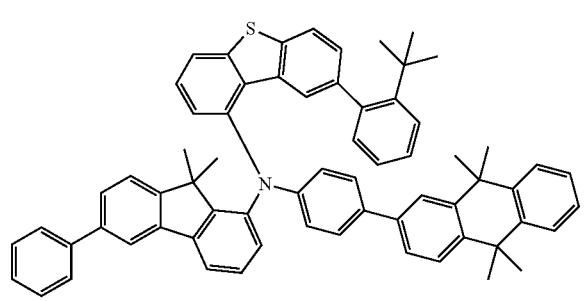
P-64
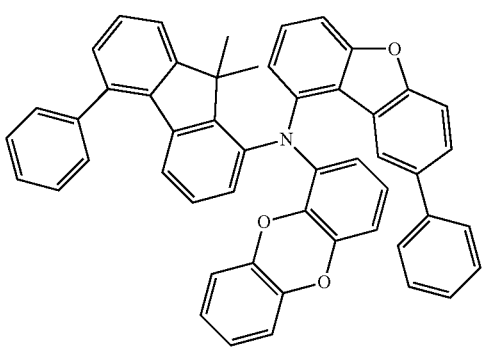

P-65
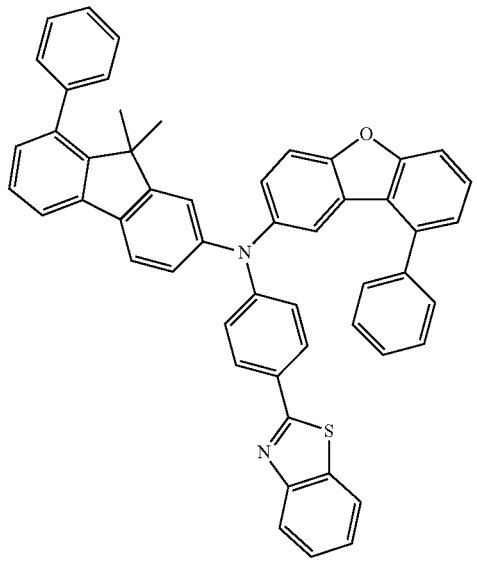
P-66
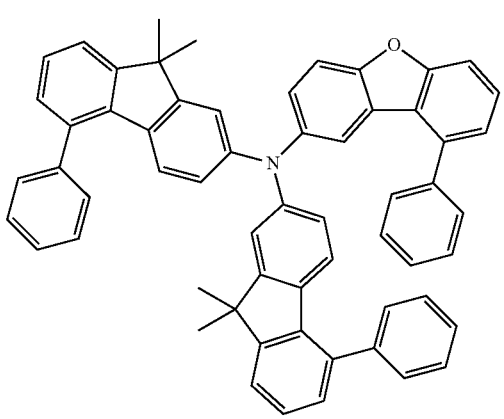
P-67
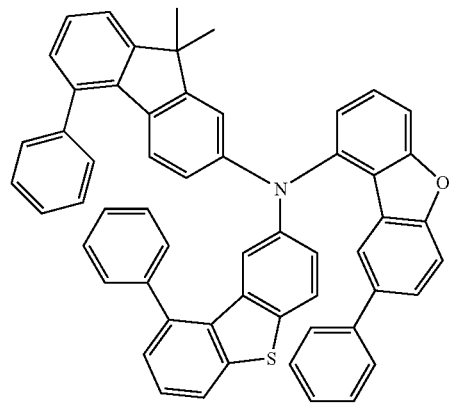
P-68
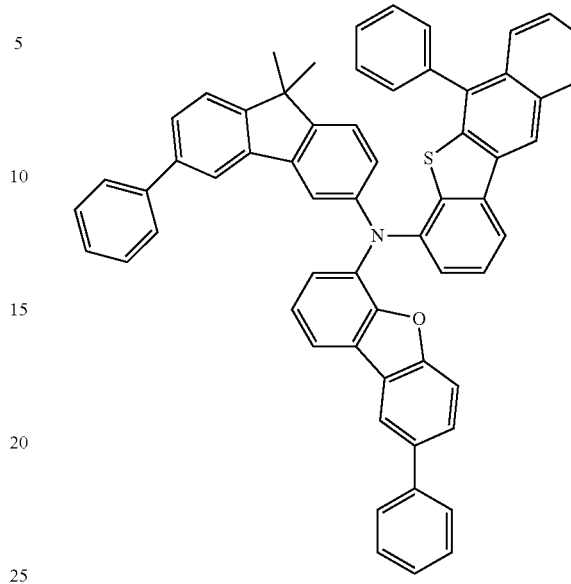
P-69
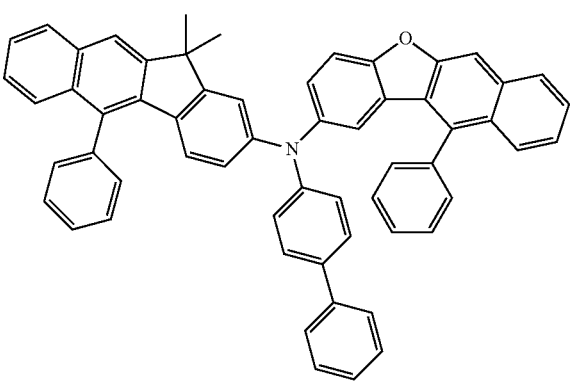
P-70
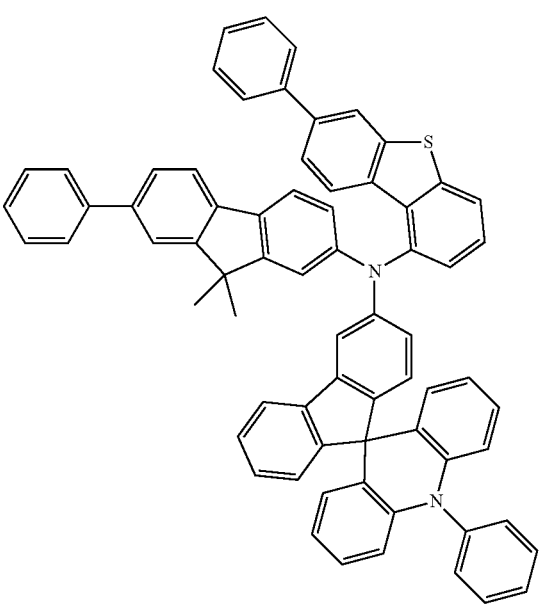

-continued
P-71
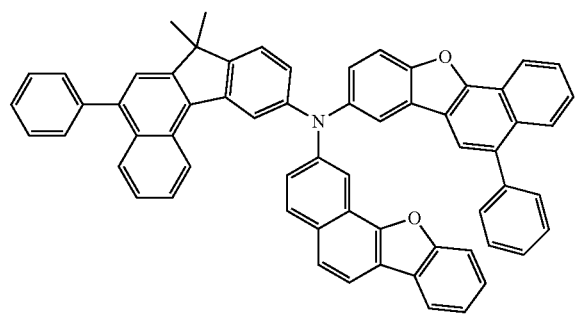
P-72
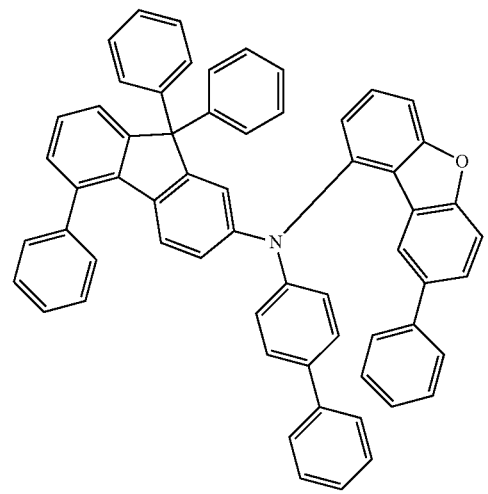
P-73
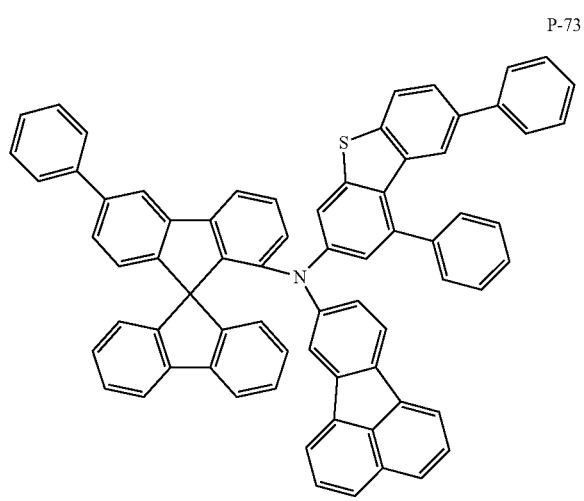
-continued
P-74
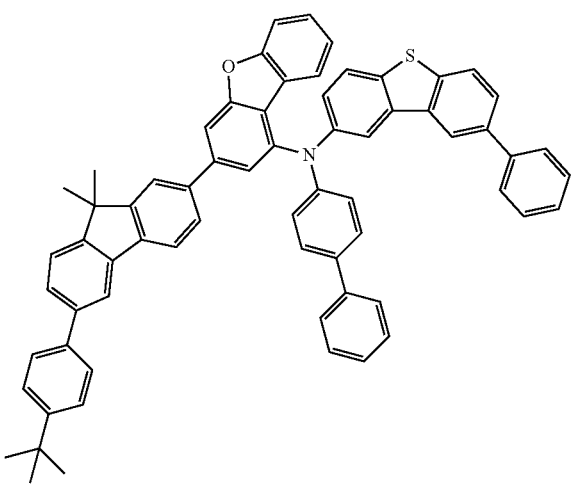
P-75
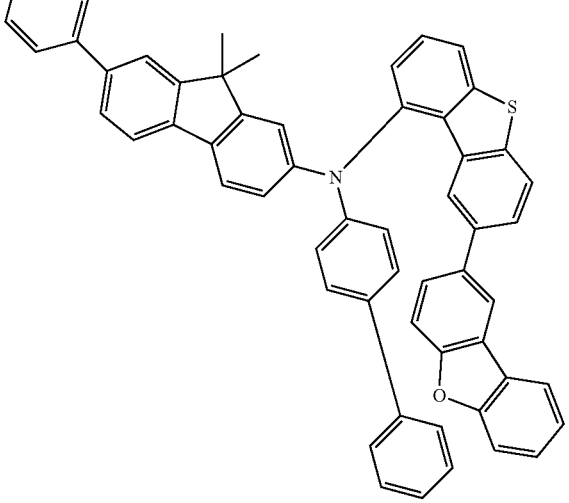
P-76
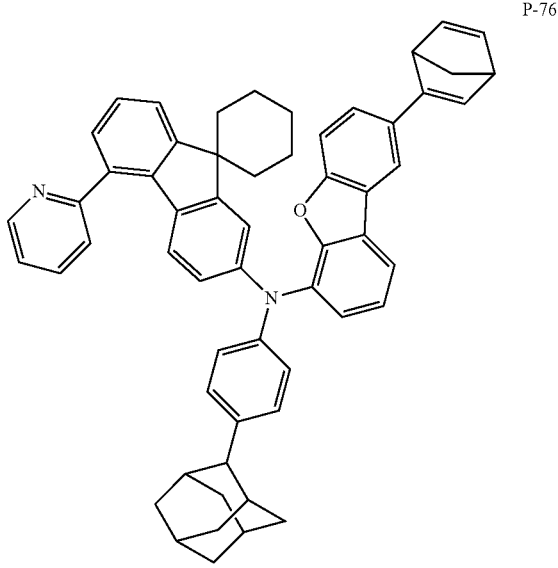

P-77
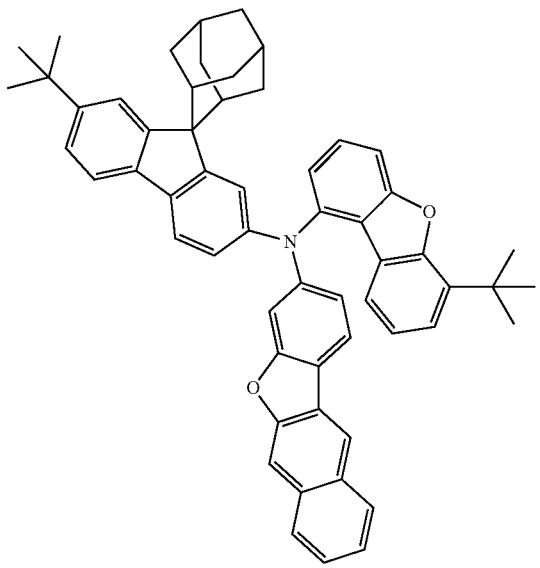
P-78
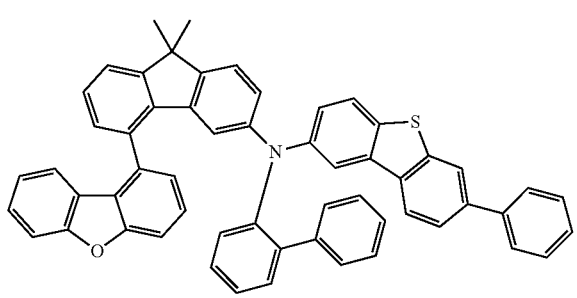
P-79
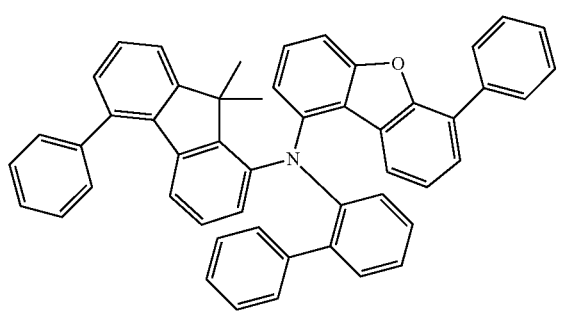
P-80
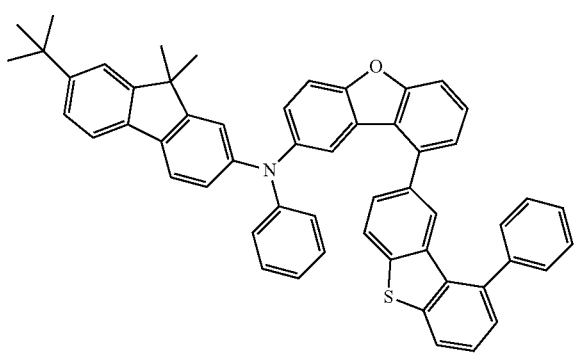
P-81
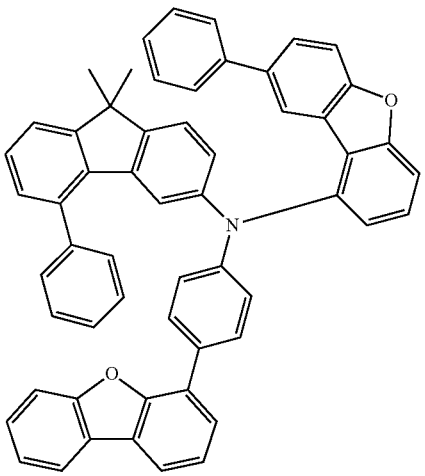
P-82
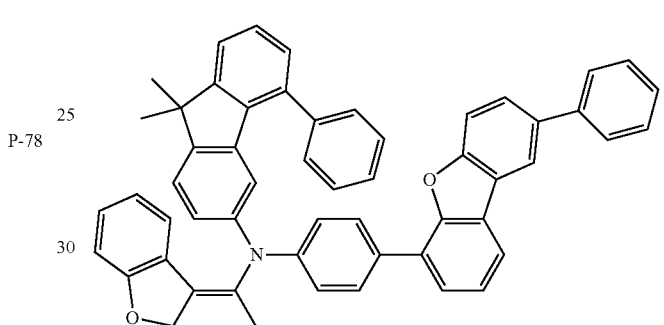
P-83
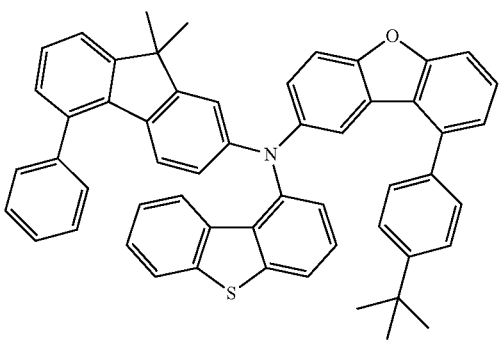
P-84
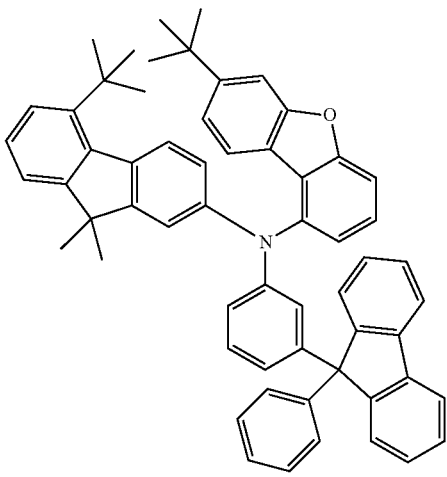

-continued
P-85
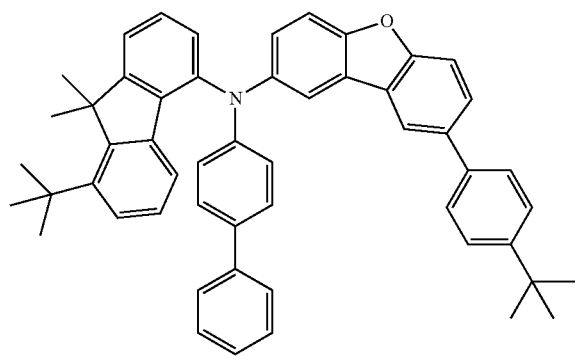
P-86
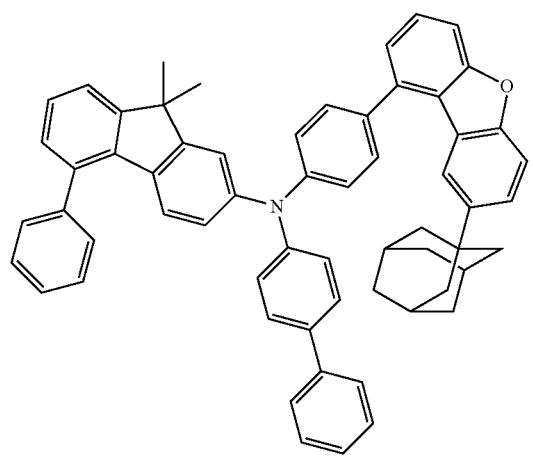
P-87
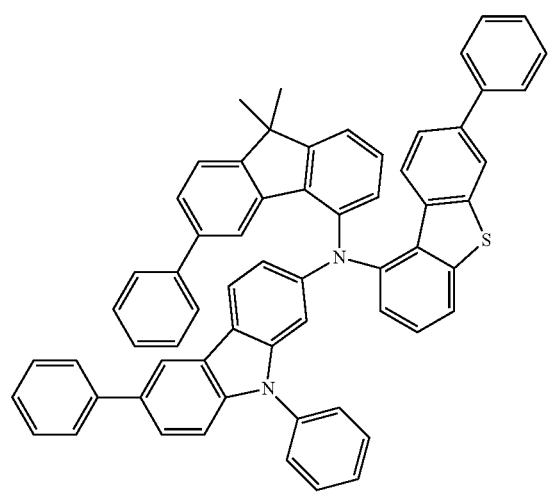
-continued
P-88
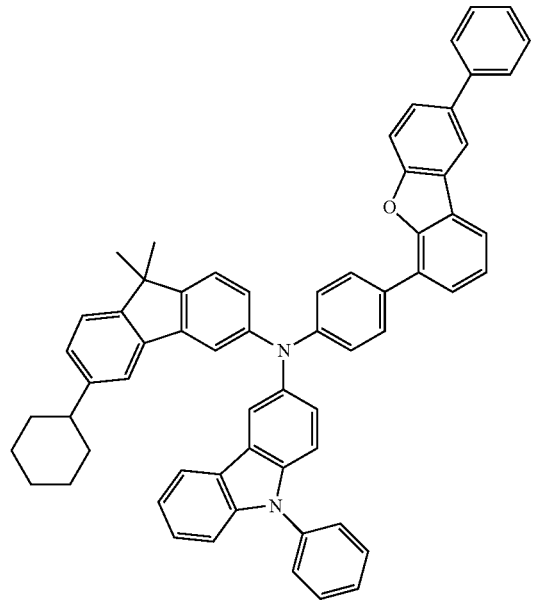
P-89
P-90
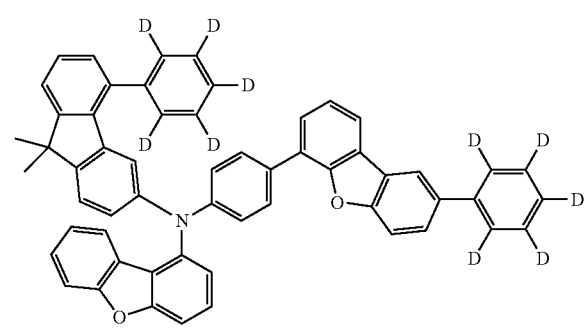

P-91
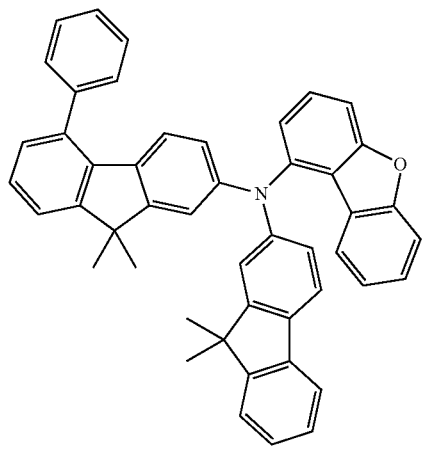
P-94
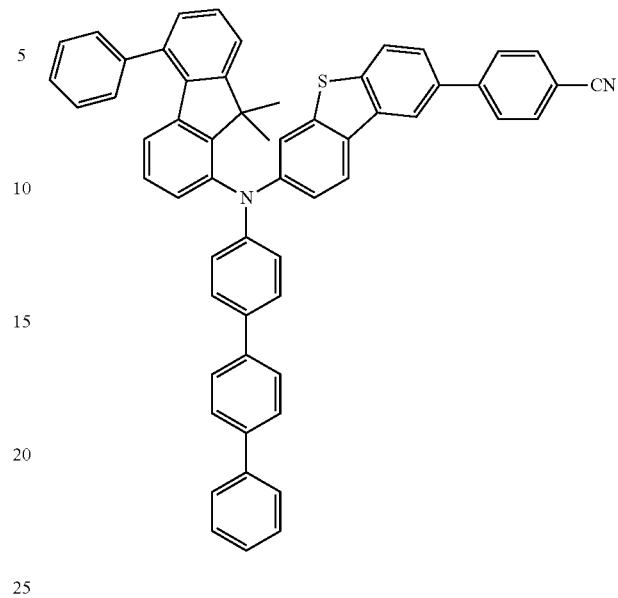
P-92
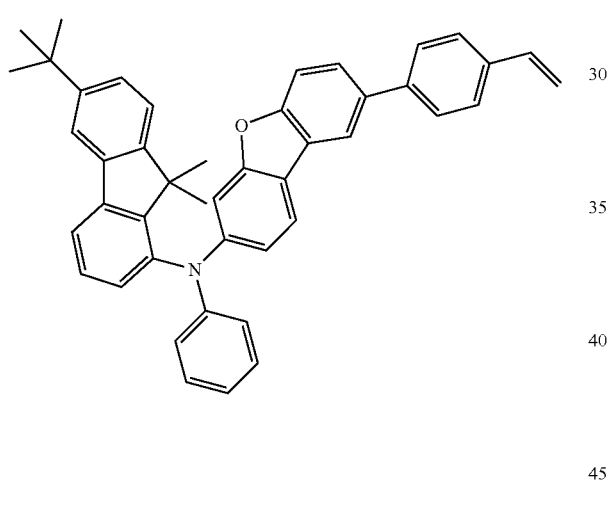
P-95
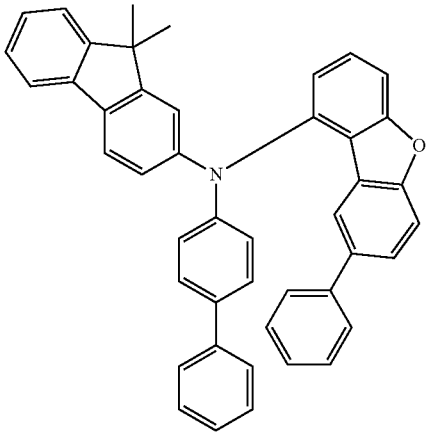
P-93
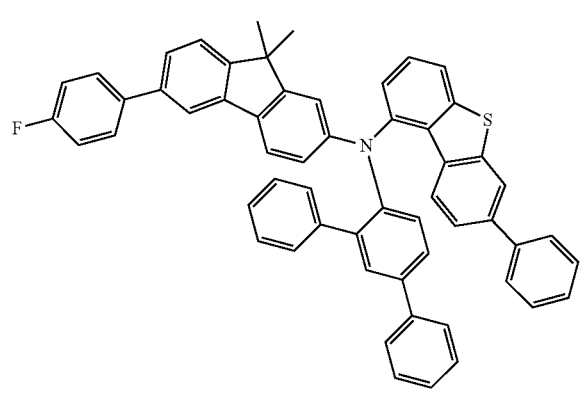
P-96
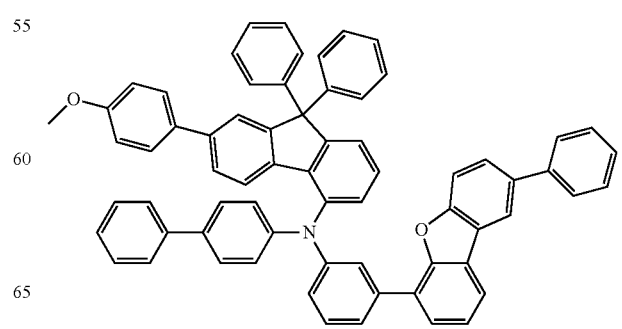

P-97
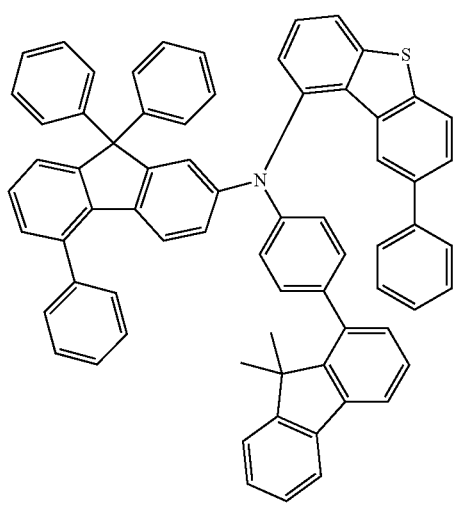
P-100
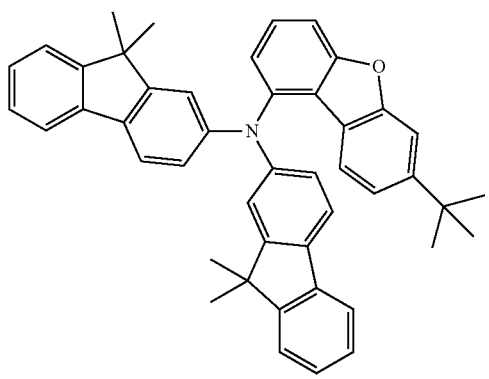
P-98
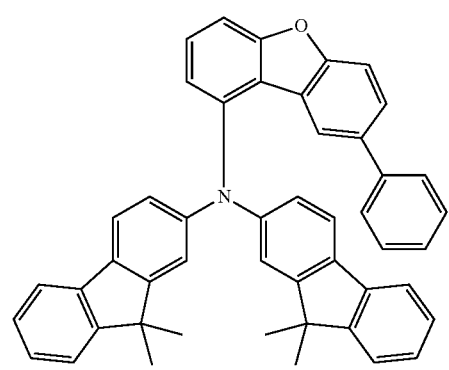
P-101
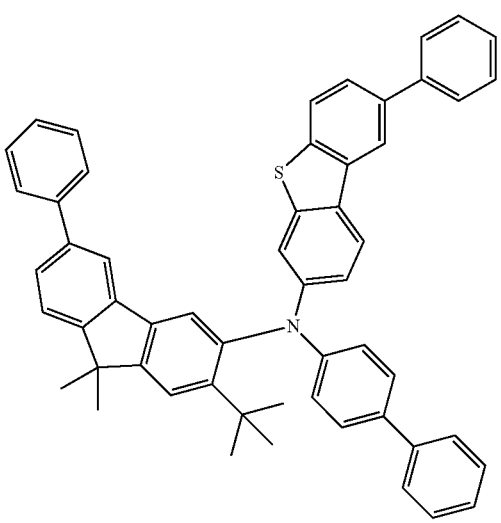
P-99
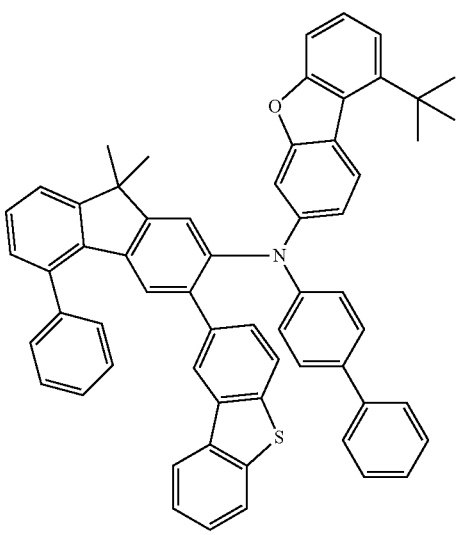
P-102

P-103
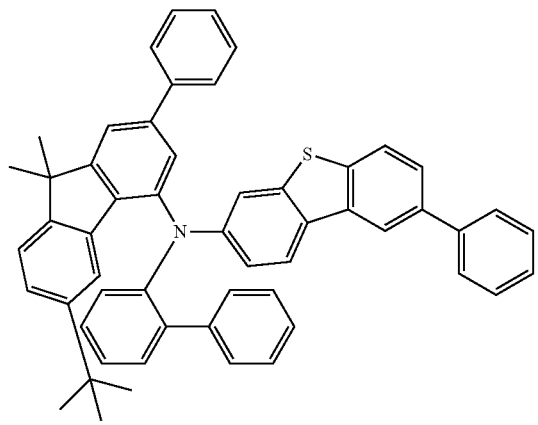
P-106
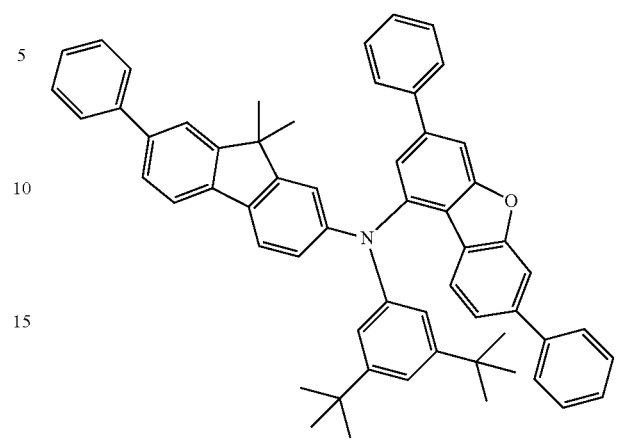
P-104
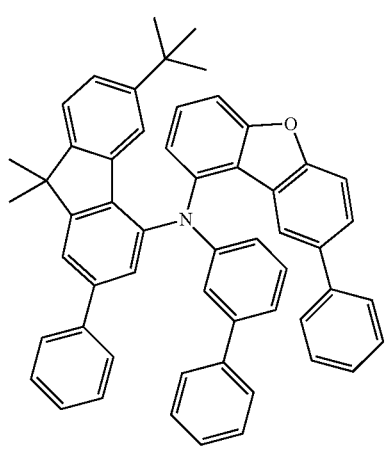
P-107
P-108
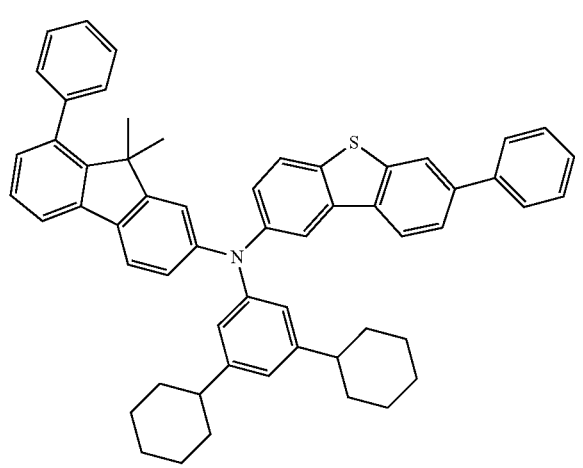
P-105
P-109
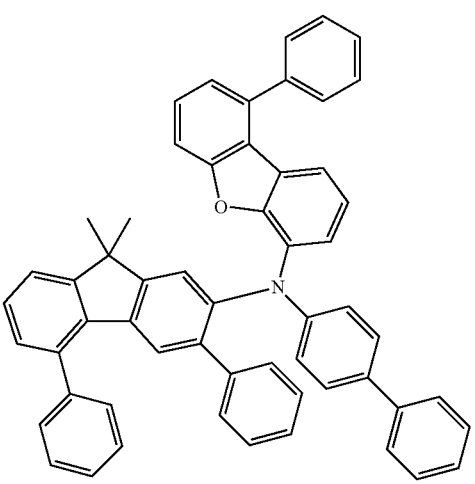

P-110
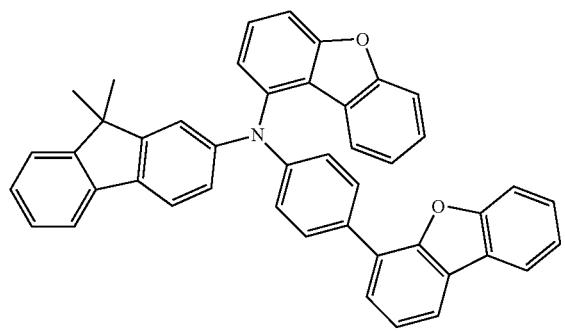
P-111
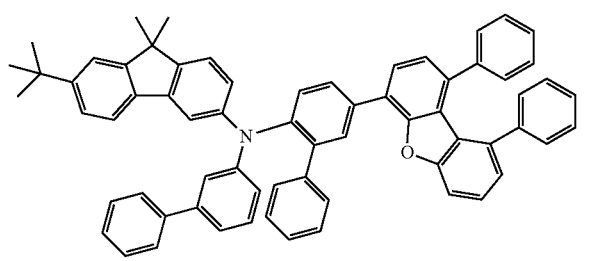
P-112
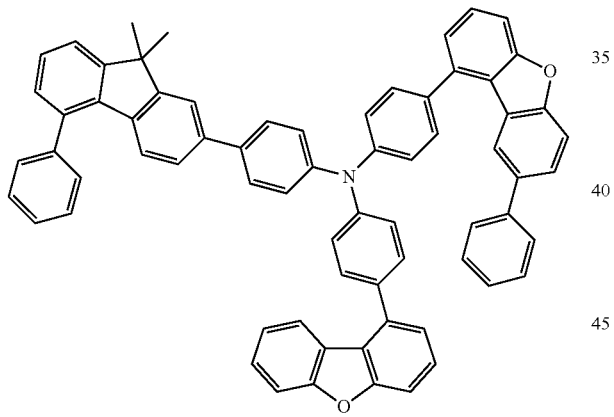
P-113
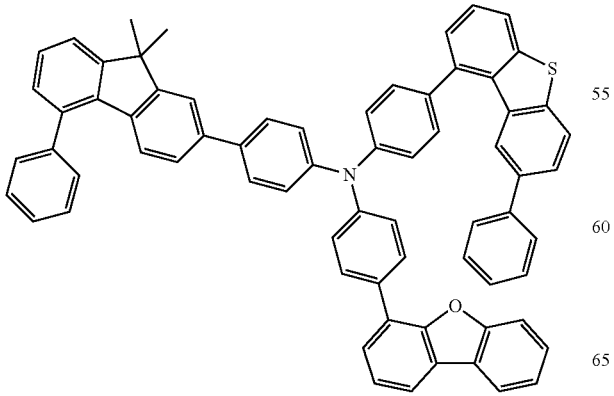
P-114
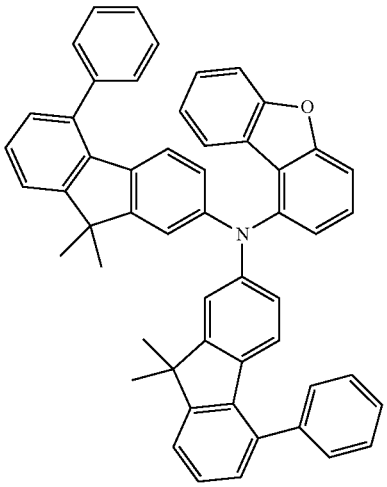
P-115
P-116
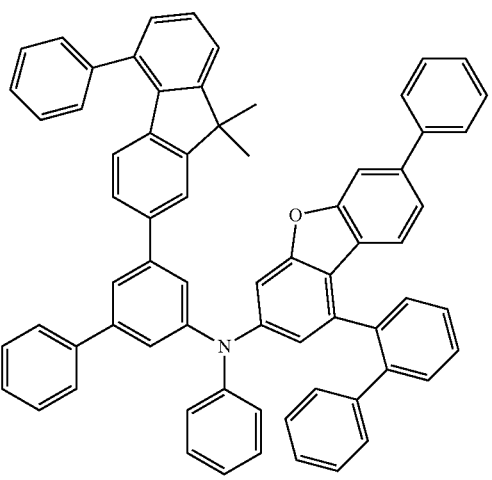

P-117
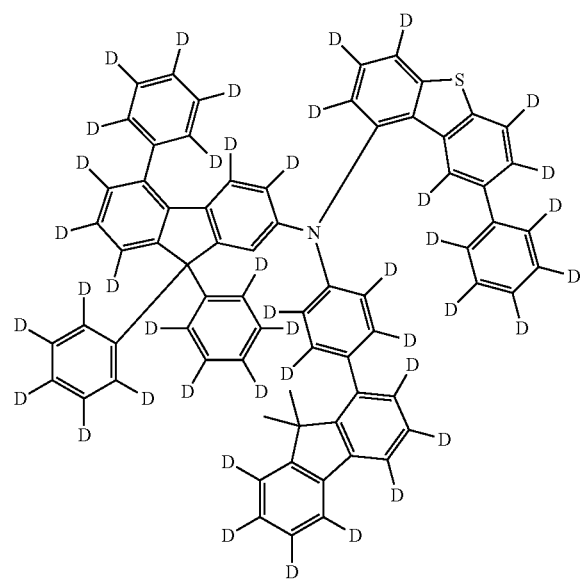
P-118
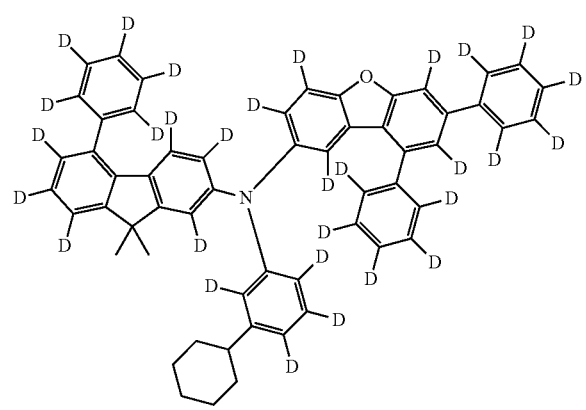
P-119
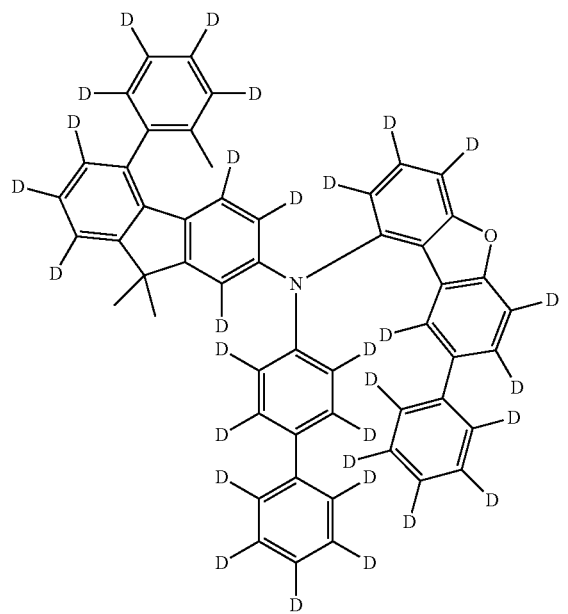
P-120
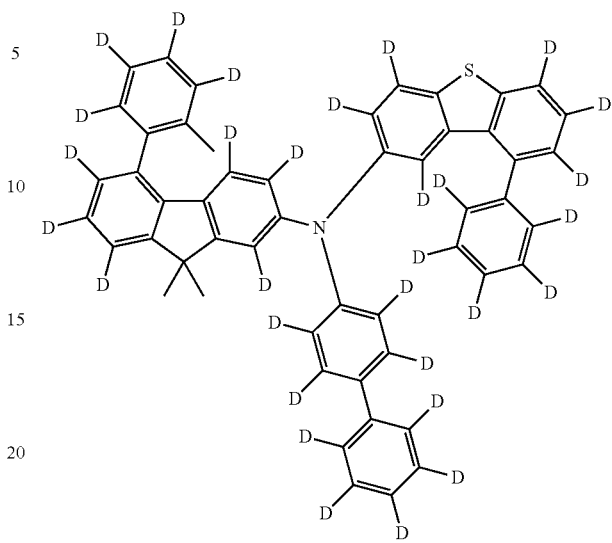
P-121
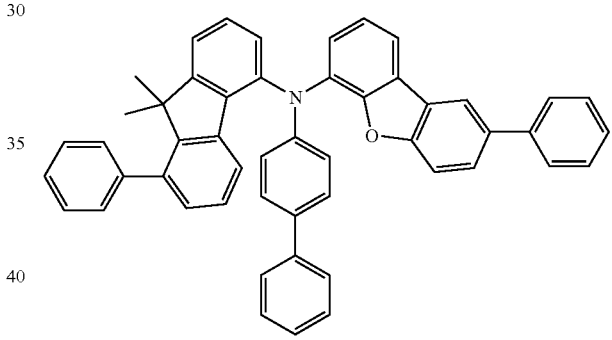
P-122
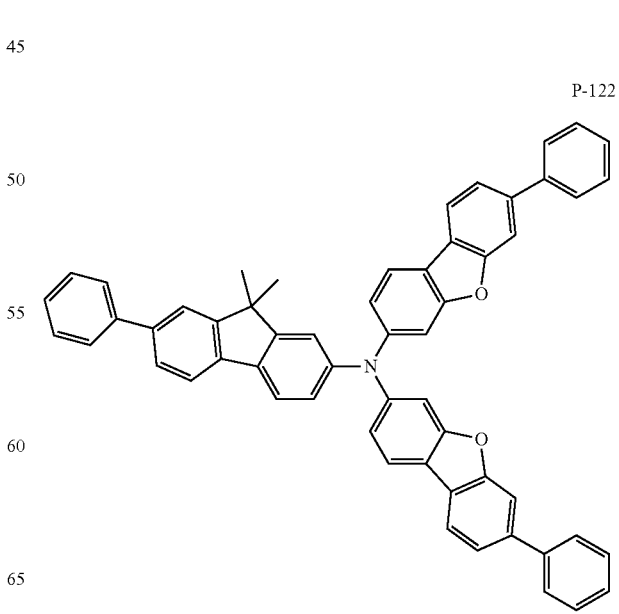

P-123
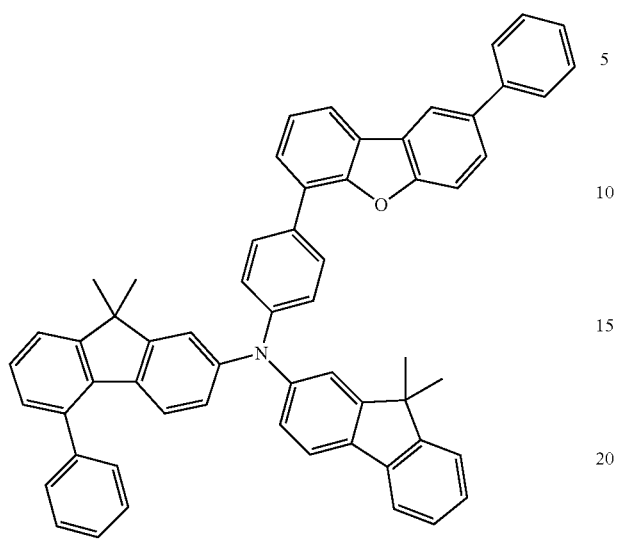
P-124
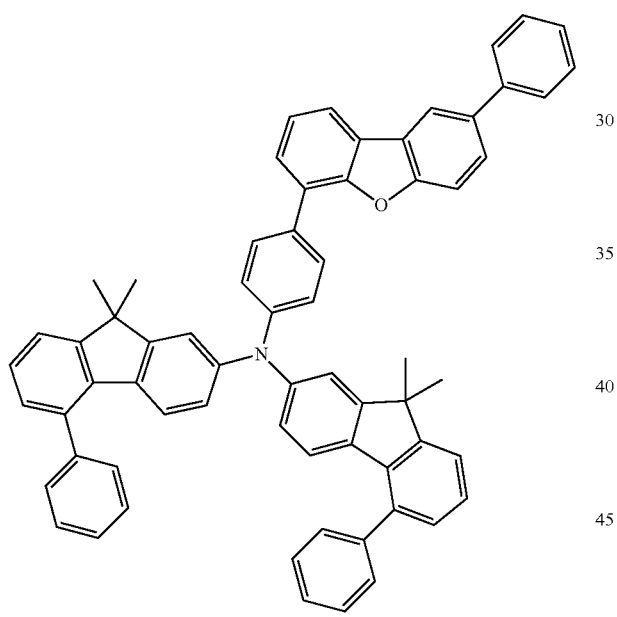
P-125
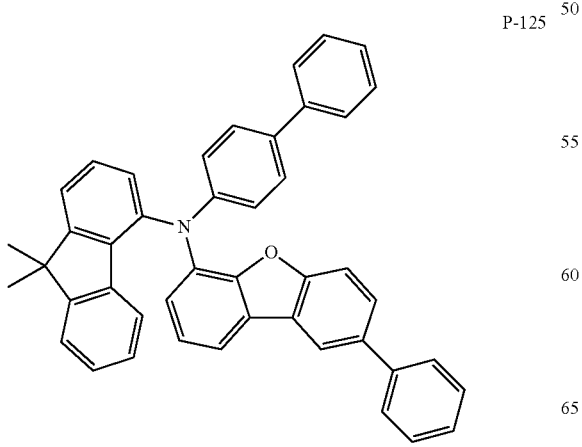
P-126
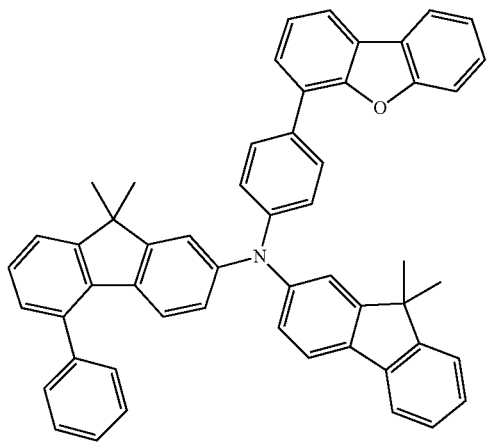
P-127
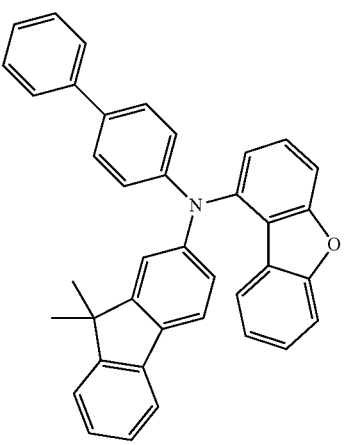
P-128
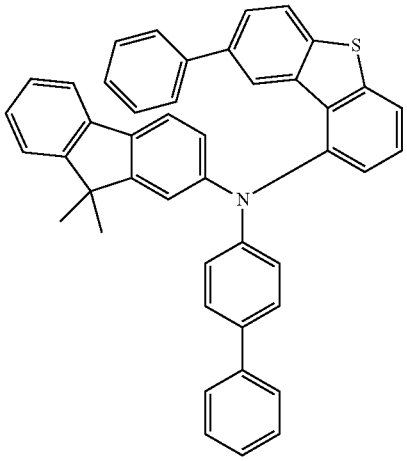

P-129
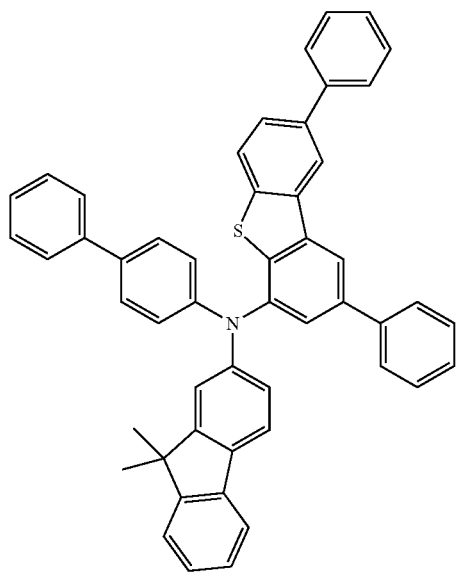
P-130
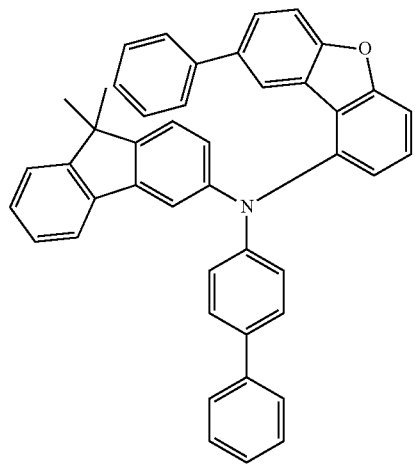
P-131
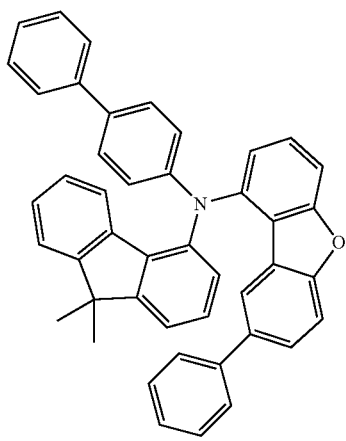
P-132
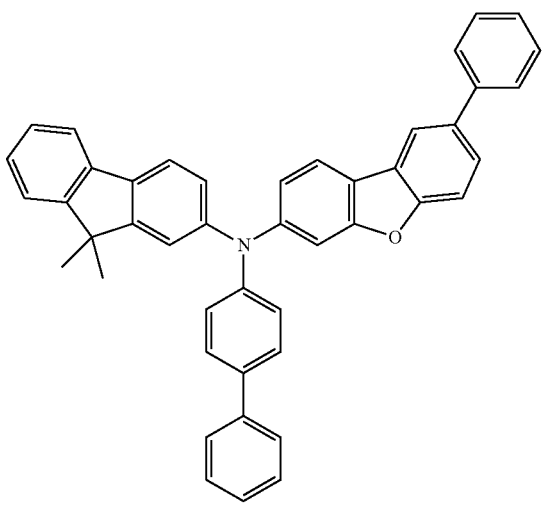
P-133
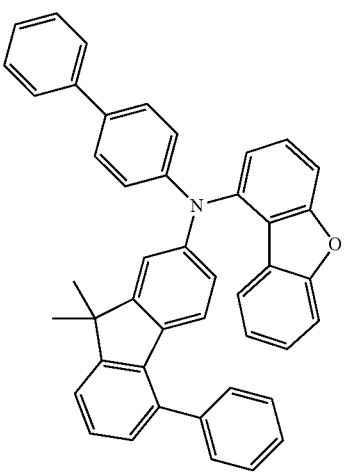
P-134
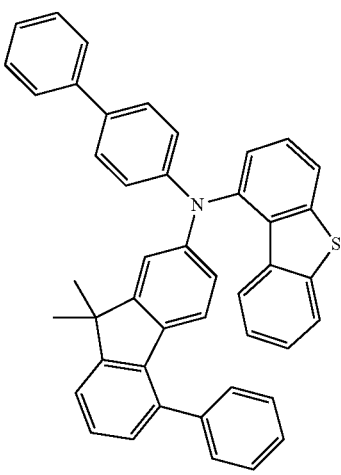

P-135
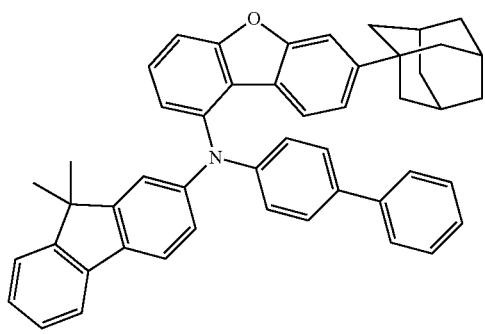
P-136
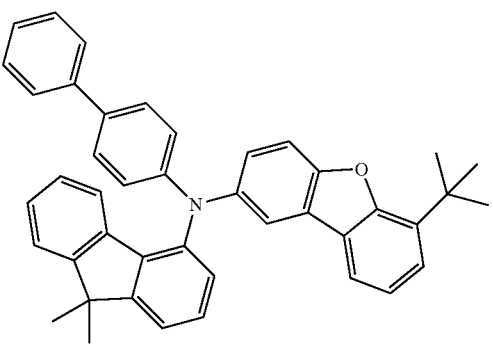
P-137
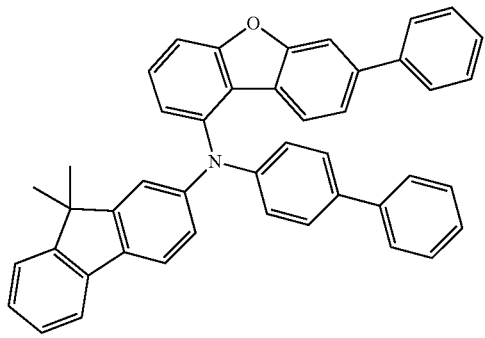
P-138
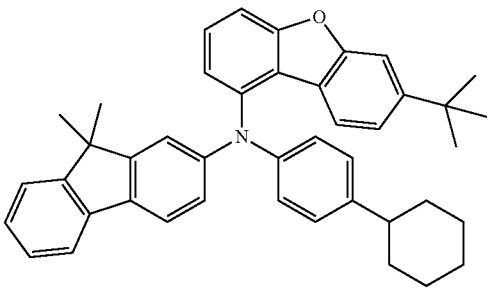
P-139
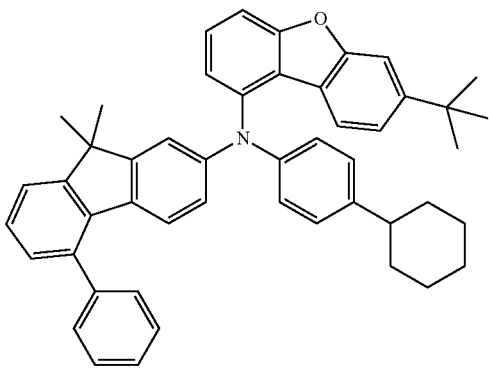
P-140
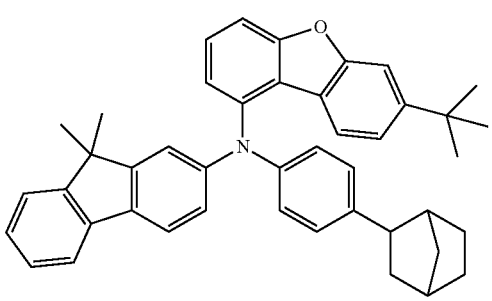
P-141
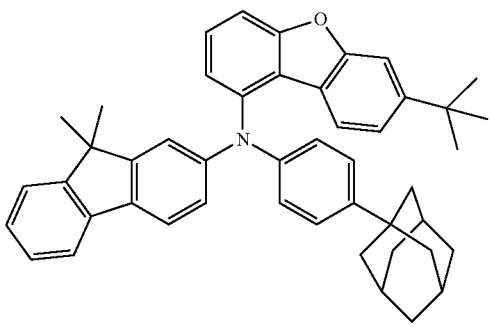
P-142
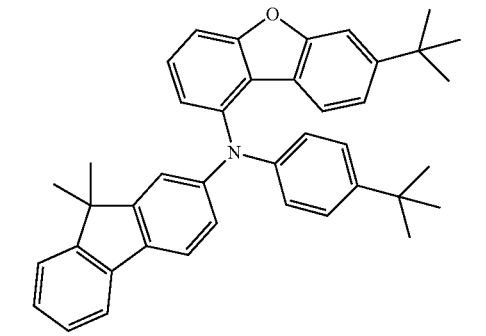

P-143
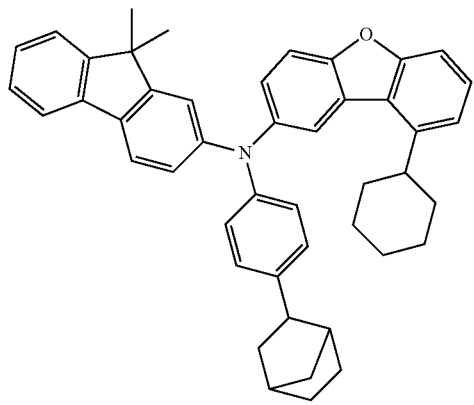
P-144
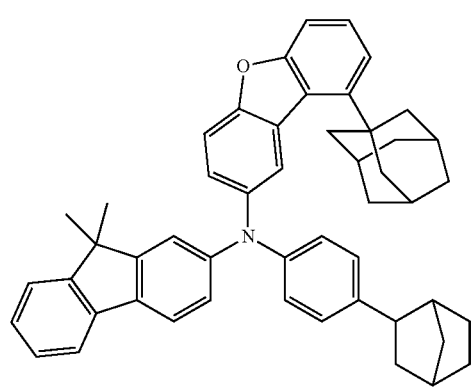
P-145
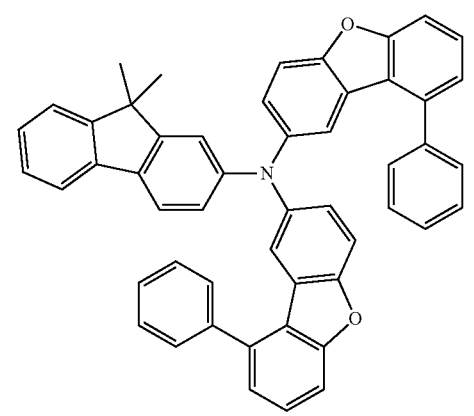
P-146
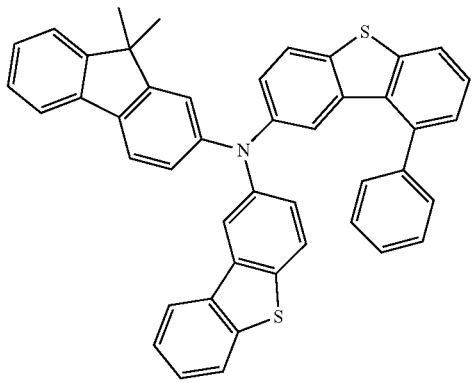
P-147
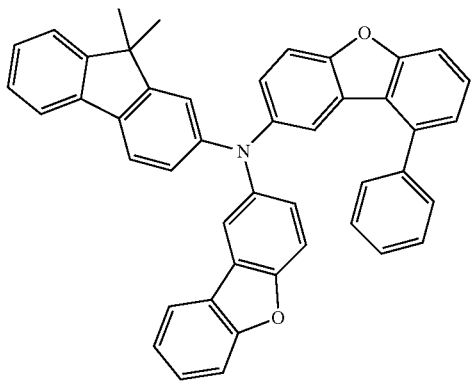
P-148
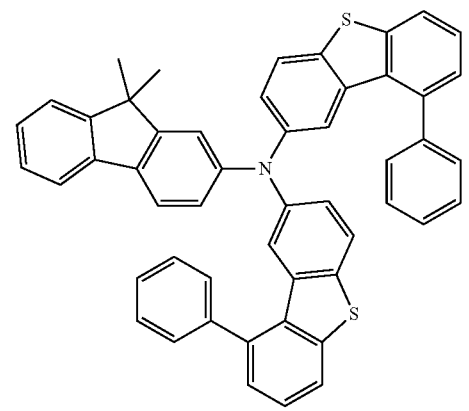
P-149
P-150

P-151
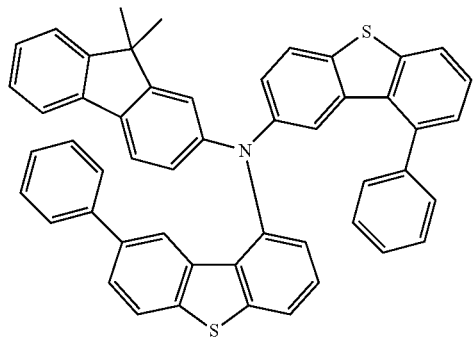
P-152
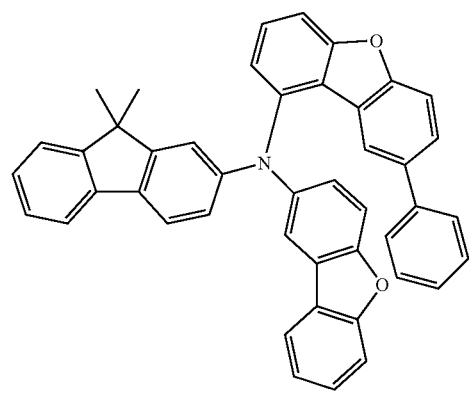
P-153
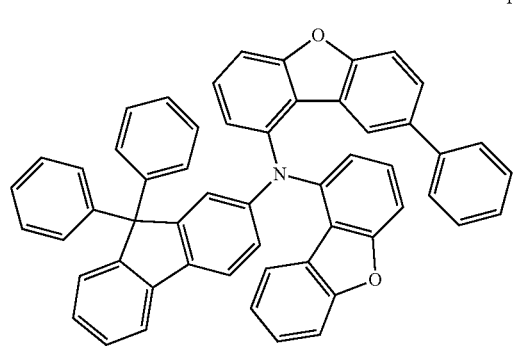
P-154
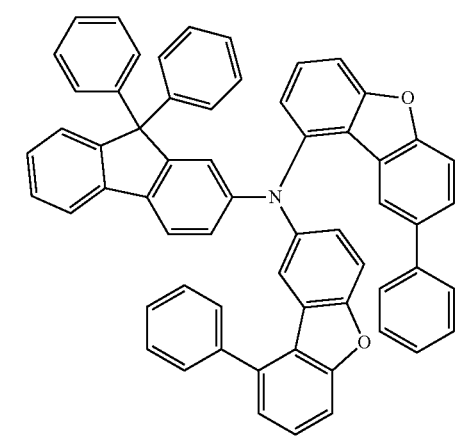
P-155
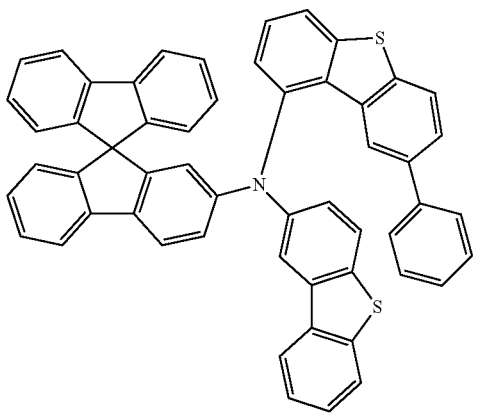
P-156
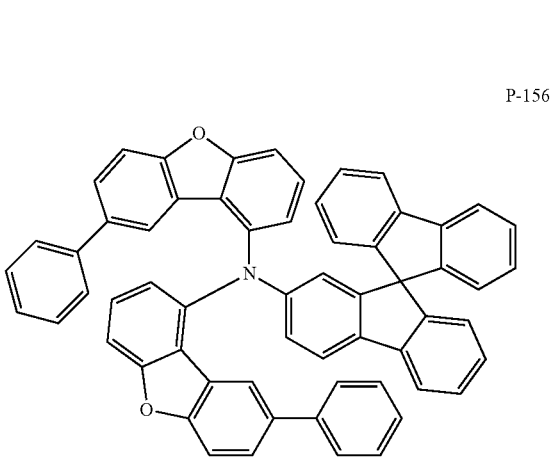
P-157
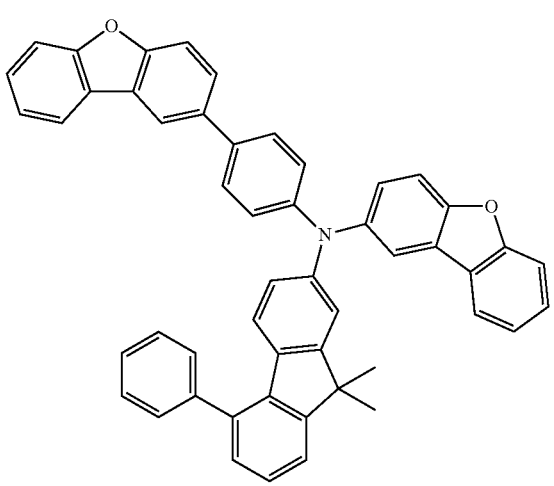

P-158
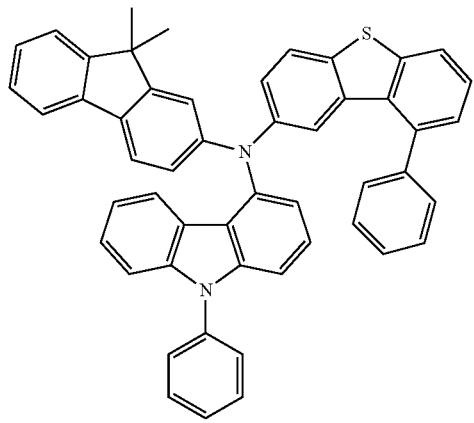
P-159
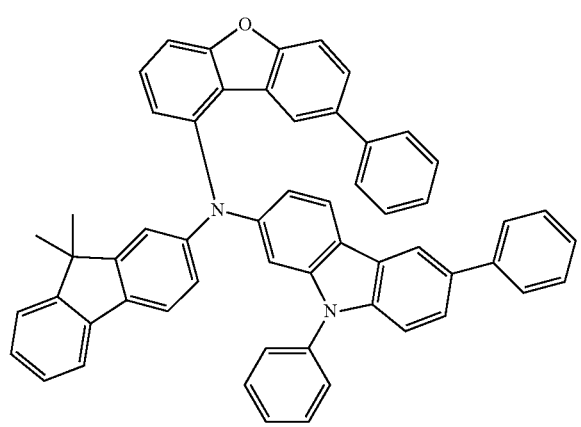
P-160
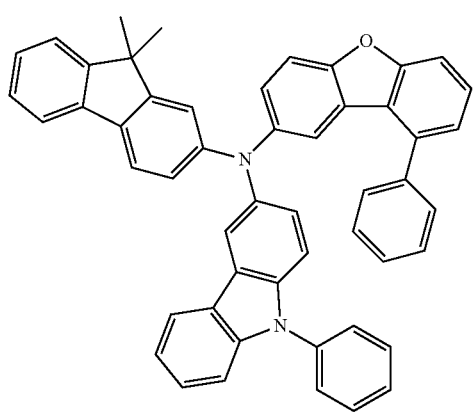
P-161
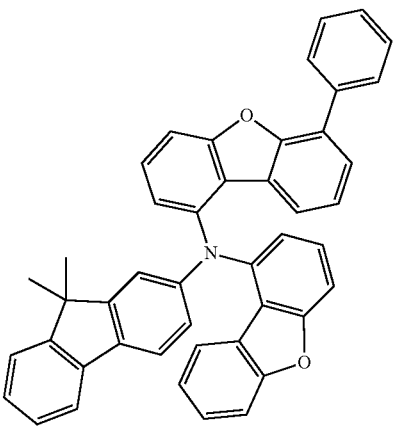
P-162
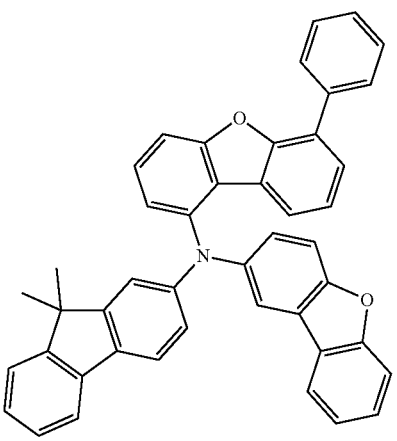
P-163

P-164
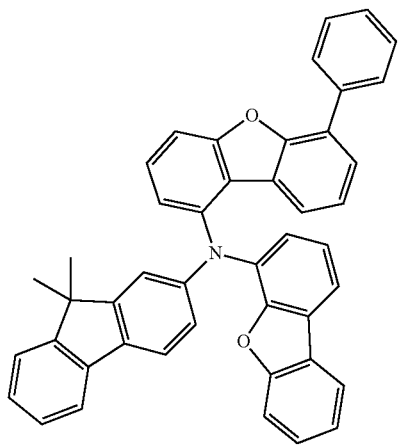
P-167
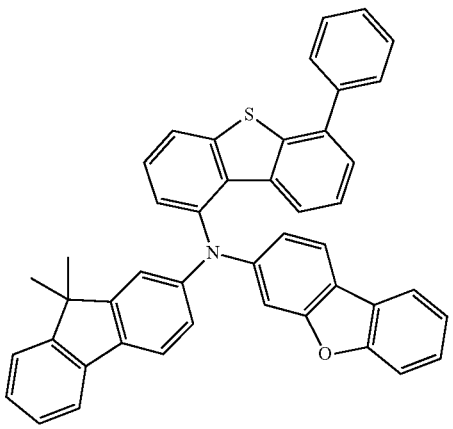
P-165
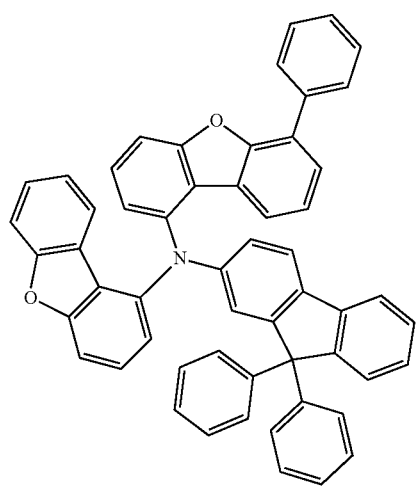
P-168
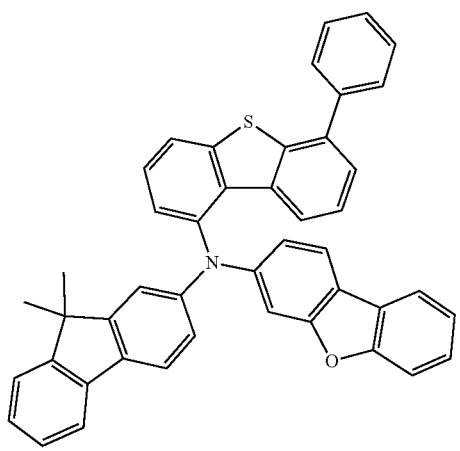
P-166
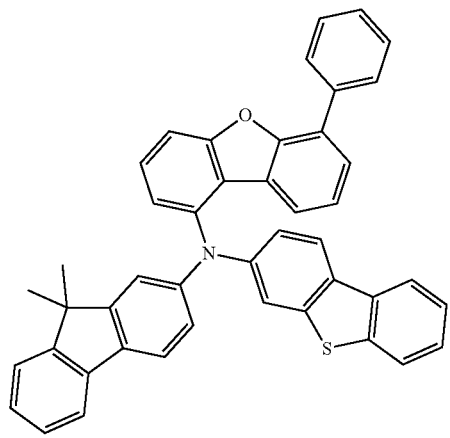
P-169
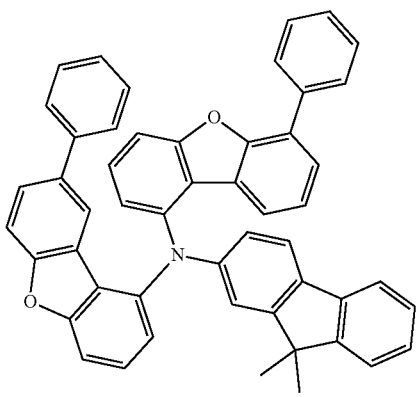

P-170
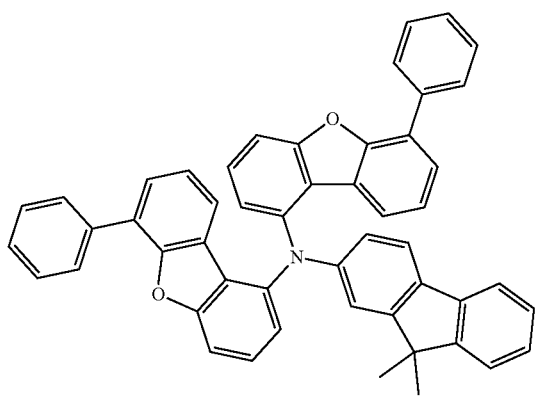
P-173
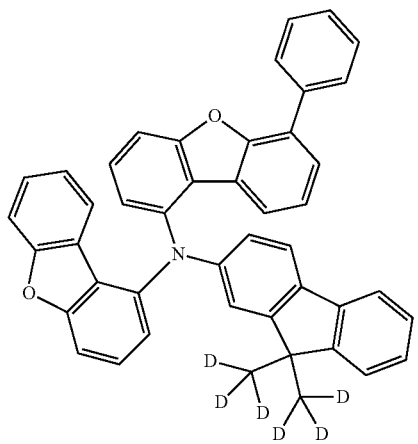
P-171
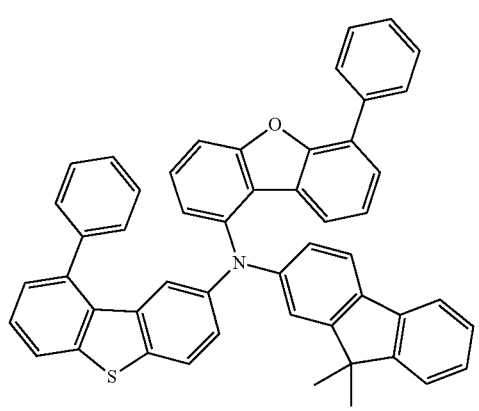
P-174
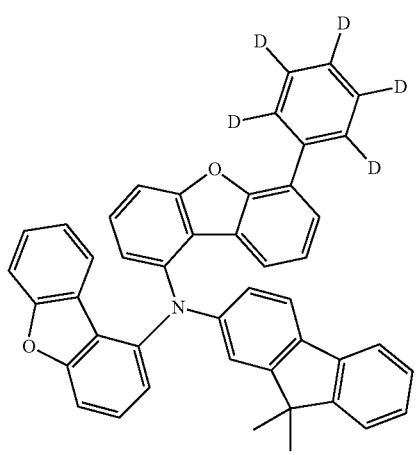
P-172
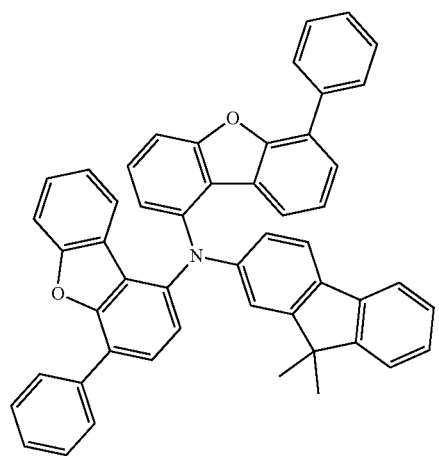
P-175
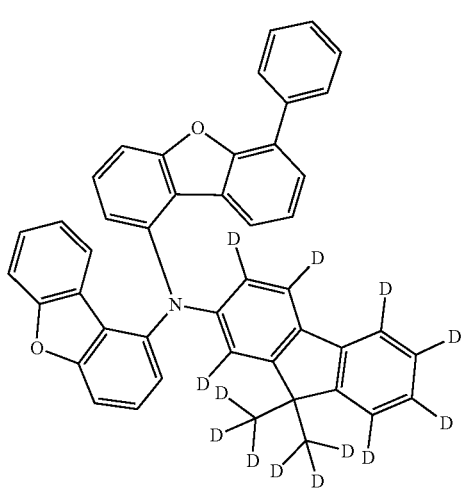

P-176
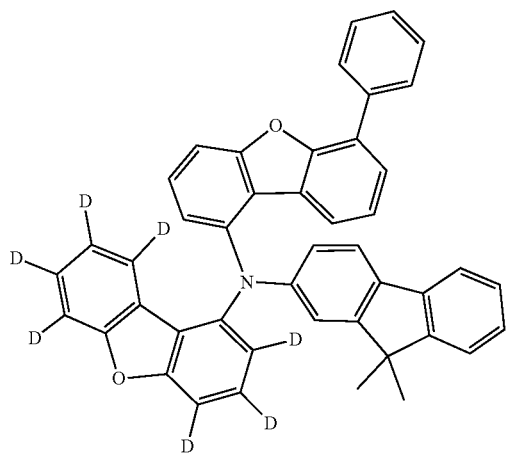
P-177
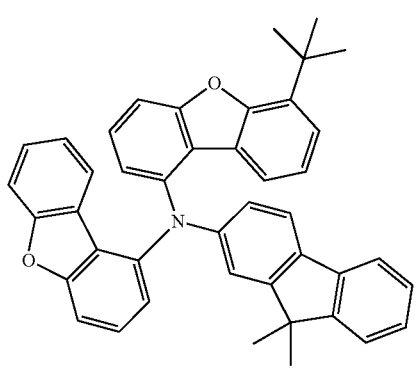
P-178
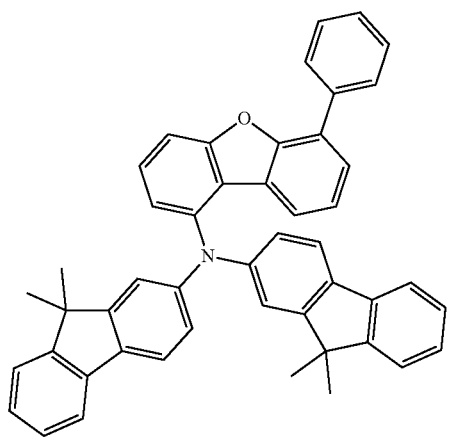
P-179
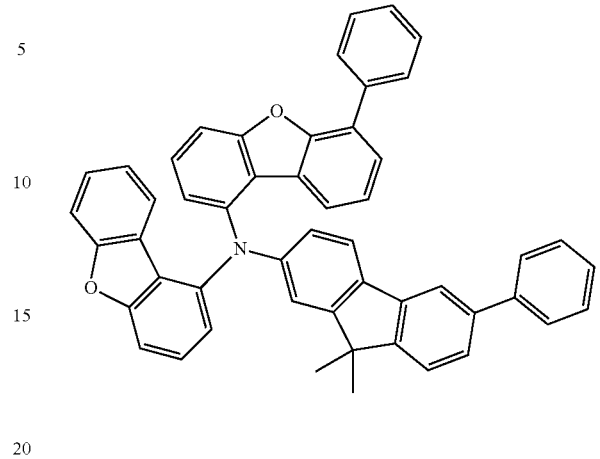
P-180
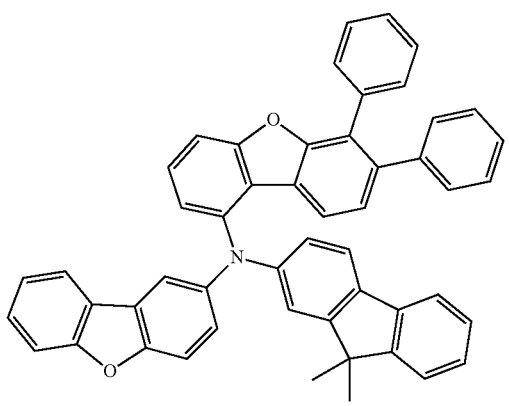
P-181
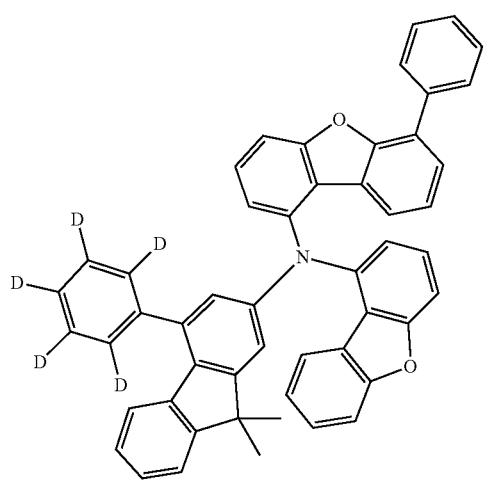

-continued

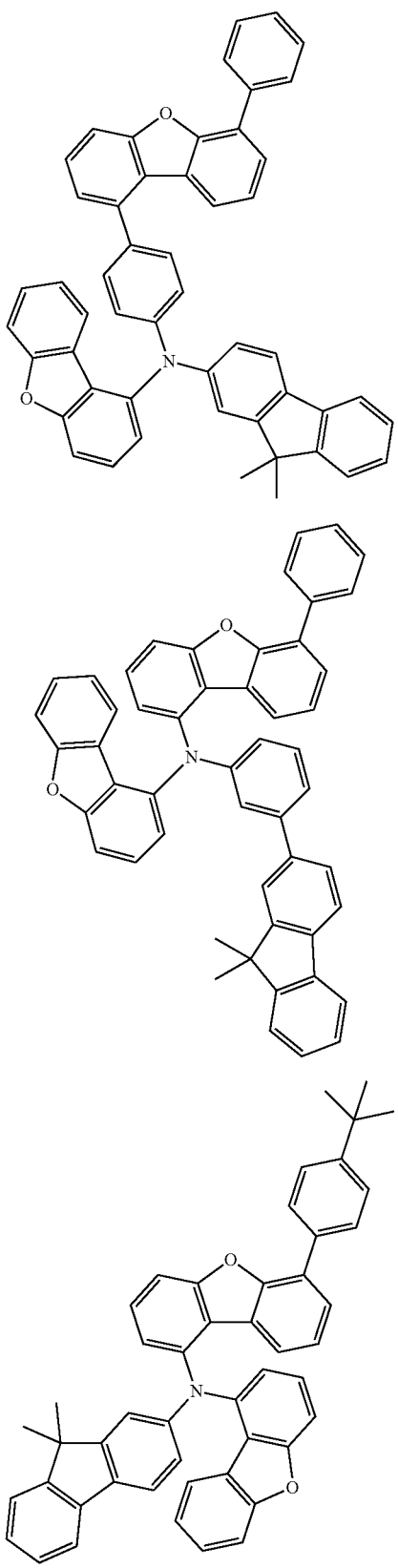

P-182

P-183

P-184

Also, the present invention provides an organic electronic element comprising a first electrode; a second electrode; and an organic material layer formed between the first electrode and the second electrode: wherein the organic material layer comprises a compound represented by Formula 1.

Also, the organic material layer comprises an emitting layer; and a hole transport band formed between the first electrode and the emitting layer; wherein the hole transport band comprises the compound represented by Formula 1.

Also, the hole transport band comprises an emitting auxiliary layer, wherein the emitting auxiliary layer comprises a compound represented by Formula 1.

Also, the emitting-auxiliary layer comprises a first emitting-auxiliary layer adjacent to the hole transport layer and a second emitting-auxiliary layer adjacent to the emitting layer, wherein the first emitting-auxiliary layer and/or the second emitting-auxiliary layer comprise compounds represented by Formula 1

Also, the present invention provides the organic electronic element comprising a first electrode; a second electrode; an organic material layer formed between the first electrode and the second electrode, wherein the organic material layer comprises an emitting layer; a hole transport layer formed between the first electrode and the emitting layer; and a plurality of emitting-auxiliary layers formed between the emitting layer and the hole transport layer, wherein the emitting-auxiliary layer comprises a first emitting-auxiliary layer adjacent to the hole transport layer and a second emitting-auxiliary layer adjacent to the emitting layer, wherein the first emitting-auxiliary layer comprises a compound represented by Formula 1.

Also, on the other aspect, the organic electronic element comprises a first electrode; a second electrode; an organic material layer formed between the first electrode and the second electrode, wherein the organic material layer comprises an emitting layer; a hole transport layer formed between the first electrode and the emitting layer; and a plurality of emitting-auxiliary layers formed between the emitting layer and the hole transport layer, wherein the emitting-auxiliary layer comprises a first emitting-auxiliary layer adjacent to the hole transport layer and a second emitting-auxiliary layer adjacent to the emitting layer, wherein the second emitting-auxiliary layer comprises a compound represented by Formula 1.

Referring to FIG. 1, the organic electronic element (100) according to the present invention comprises a first electrode (110), a second electrode (170), an organic material layer comprising single compound or 2 or more compounds represented by Formula 1 between the first electrode (110) and the second electrode (170). Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
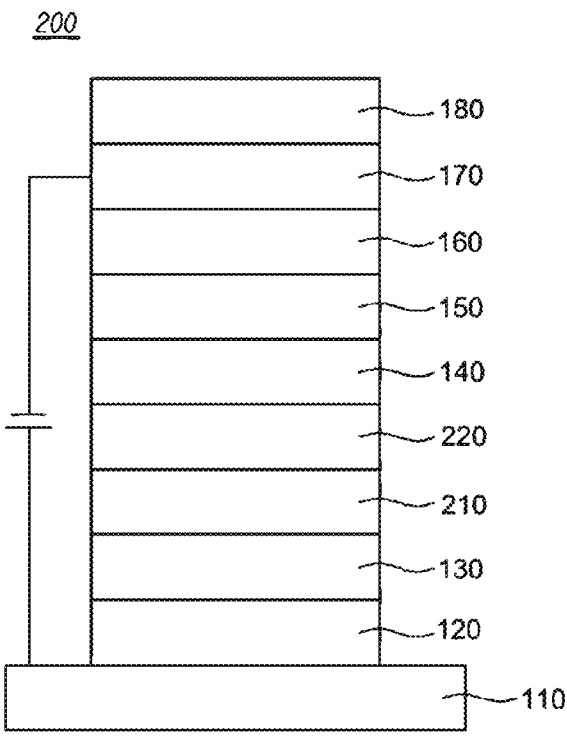

The organic material layer may sequentially comprise a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the compound according to Formula 1 of the present invention can be used as a material for the emitting-auxiliary layer or the hole transport layer.

Figure 3:
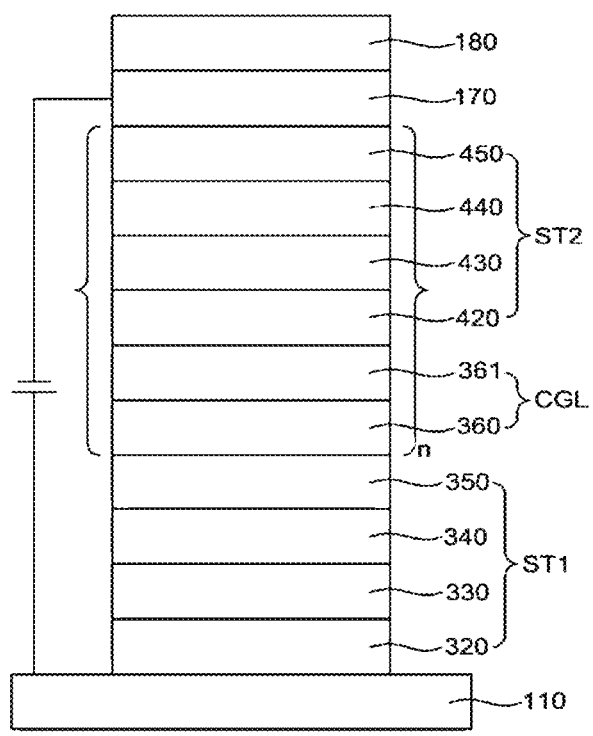
Figure 4:
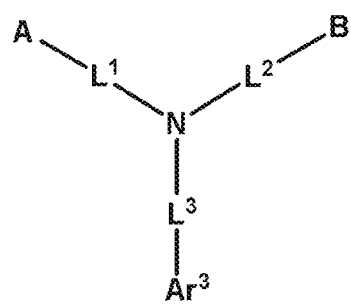
FIG. 4 shows a Formula according to one aspect of the present invention.

The organic material layer may comprise 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula 1 to the organic material layer.

Also, the present invention provides a composition for an emitting-auxiliary layer comprising the compound represented by Formula 1, and provides an organic electronic element comprising the emitting-auxiliary layer.

Also, the present invention provides a composition for a hole transport layer comprising the compound represented by Formula 1, and provides an organic electronic element comprising the hole transport layer.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1, and preparation examples of the organic electronic element of the present invention will be described in detail by way of example, but are not limited to the following examples.

EXAMPLES

Synthesis Example 1

The compound (final products) represented by Formula 1 according to the present invention is synthesized as shown in Reaction Scheme 1, but is not limited thereto.

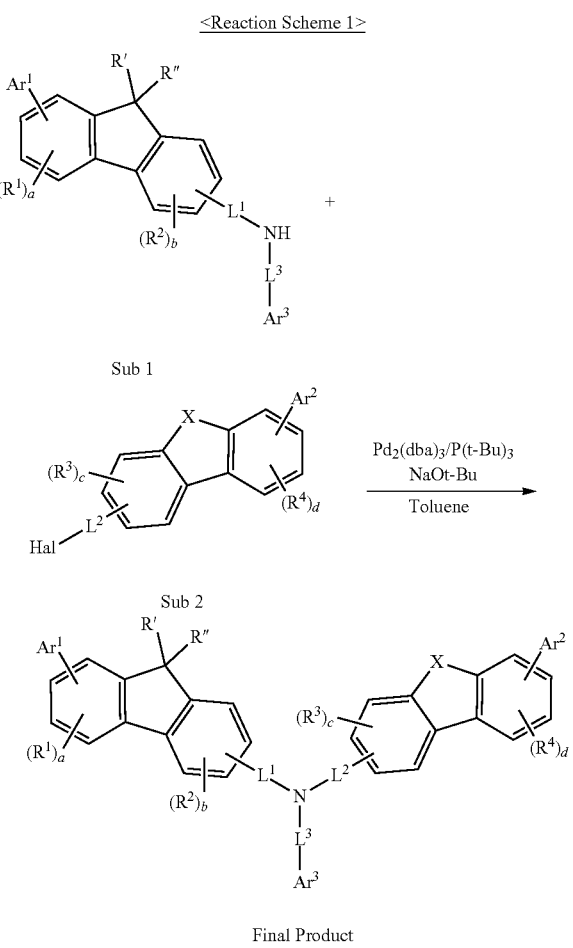

Wherein,
1) Hal is I, Br or Cl,
2) $Ar^1$, $Ar^2$, $Ar^3$, $L^1$, $L^2$, $L^3$, $R^1$, $R^2$, $R^3$, $R^4$, R', R'', X, a, b, c and d are the same as defined above.

89
I. Synthesis of Sub 1

Sub 1 of Reaction Scheme 1 may be synthesized through the reaction route of Reaction Scheme 2, but is not limited thereto. Hal is I, Br or Cl.

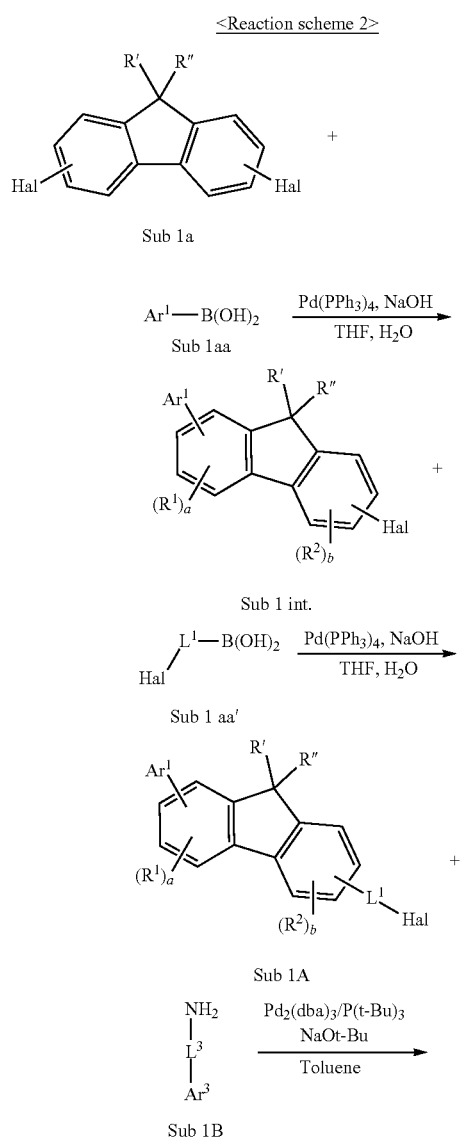

In Reaction Scheme 2, if $L^1$ of Sub 1 is absent, the step of reacting with $L^1$ can be omitted.

90
1. Synthesis Example of Sub 1-11

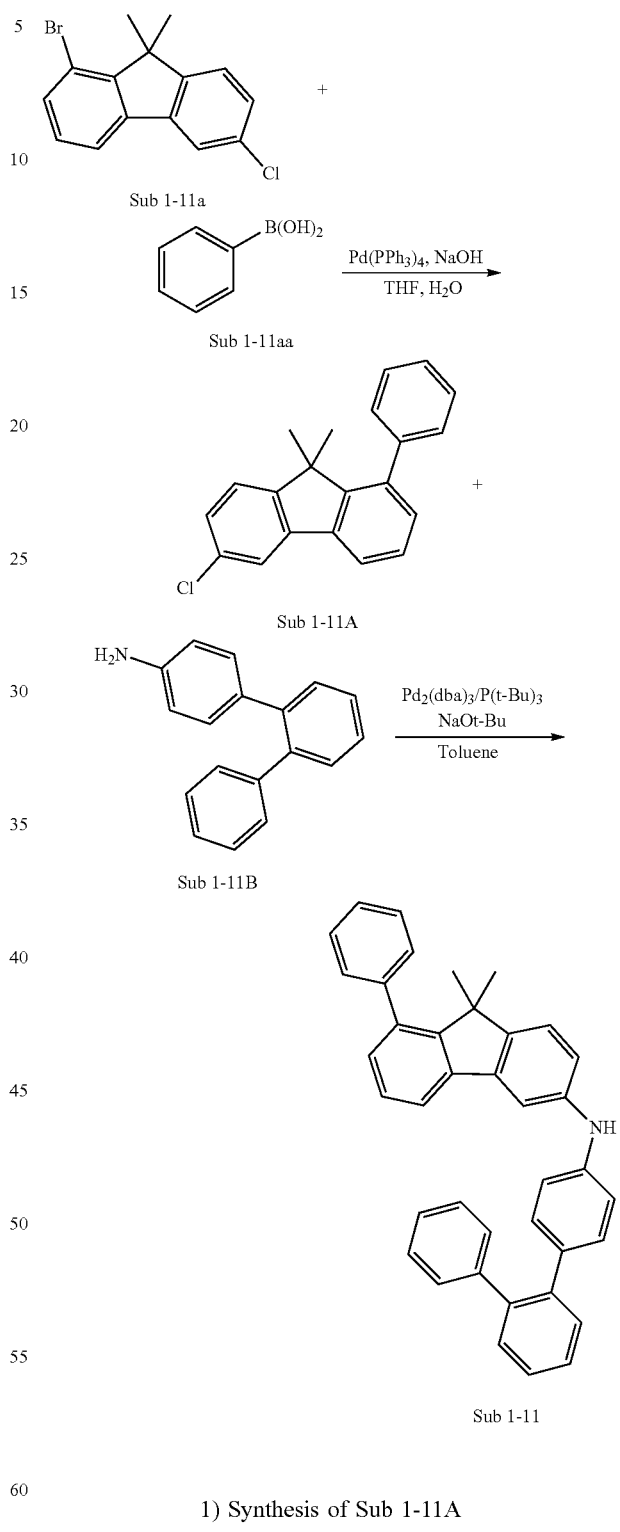

1) Synthesis of Sub 1-11A

After dissolving Sub 1-11a (50.0 g, 162.5 mmol) with THF (813 ml) in a round bottom flask, Sub 1-11aa (19.8 g, 121.93 mmol), Pd(PPh$_3$)$_4$ (11.3 g, 9.8 mmol), NaOH (19.5 g, 487.6 mmol) and water (406 mL) were added and proceeded with the reaction at 80° C. When the reaction was completed, extracted with CH₂Cl₂ and water, the organic layer was dried over MgSO₄ and concentrated, and the resulting compound was recrystallized using a silicagel column to obtain 41.4 g of product (yield: 83.5%).

2) Synthesis of Sub 1-11

After dissolving Sub 1-11A (41.4 g, 135.8 mmol) obtained in the above synthesis with toluene (679 mL) in a round bottom flask, Sub 1-11B (32.2 g, 135.8 mmol), Pd₂(dba)₃ (3.7 g, 4.1 mmol), P(t-Bu)₃ (1.7 g, 8.2 mmol), NaOt-Bu (26.1 g, 271.6 mmol) were added and stirred at 120° C. When the reaction was completed, extracted with CH₂Cl₂ and water, the organic layer was dried over MgSO₄ and concentrated, and the resulting compound was recrystallized using a silicagel column to obtain 50.4 g of product (yield: 72.3%).

2. Synthesis Example of Sub 1-57

1) Synthesis of Sub 1-57A

After dissolving Sub 1-57a (50.0 g, 162.5 mmol) with THF (813 ml) in a round bottom flask, Sub 1-57aa (38.7 g, 162.5 mmol), Pd(PPh₃)₄ (11.3 g, 9.8 mmol), NaOH (19.5 g, 487.6 mmol), Water (406 ml) were added and 55.6 g of product was obtained by performing the same experiment as Sub 1-11A. (Yield: 81.2%)

2) Synthesis of Sub 1-57

In a round bottom flask, Sub 1-57A (55.6 g, 132.1 mmol) obtained in the above synthesis and Sub 1-57B (21.6 g, 132.1 mmol), Pd₂(dba)₃ (3.6 g, 4.0 mmol), P(t-Bu)₃ (1.6 g, 7.9 mmol), NaOt-Bu (25.4 g, 264.1 mmol), toluene (660 mL) were tested in the same manner as for Sub 1-11, and 52.7 g of product was obtained. (Yield: 72.0%)

3. Synthesis Example of Sub 1-69

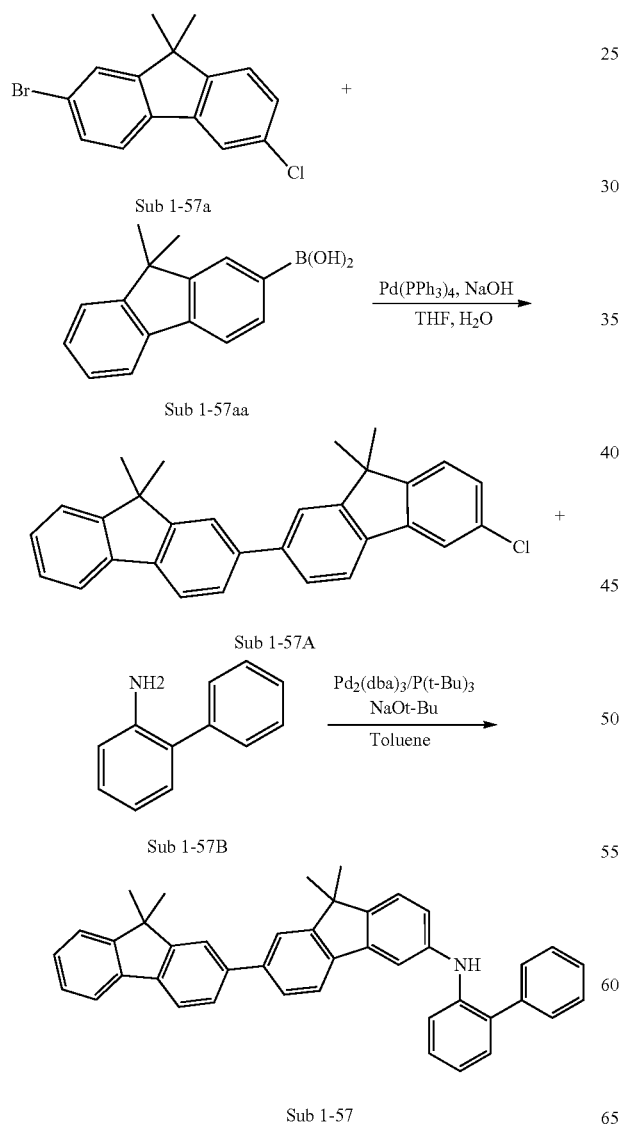

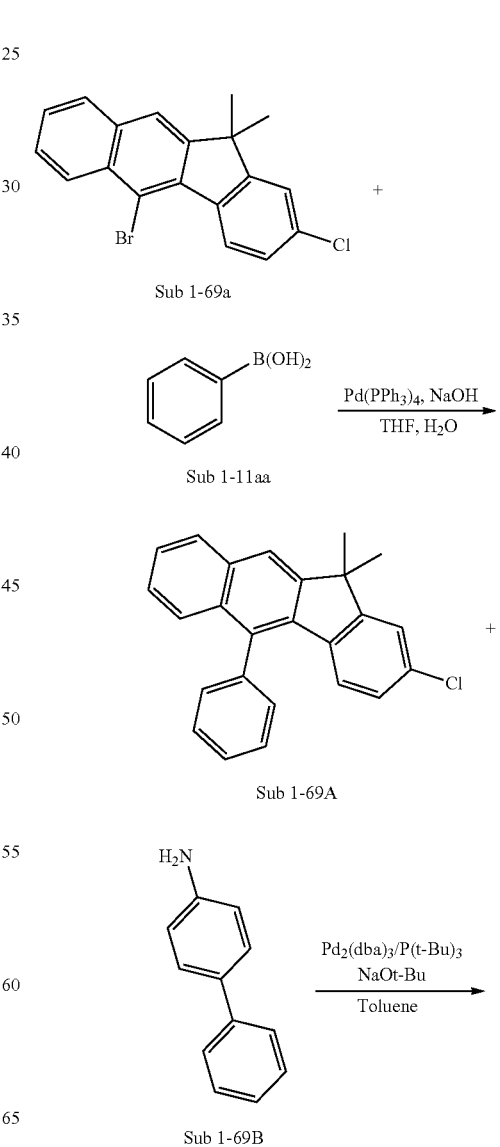

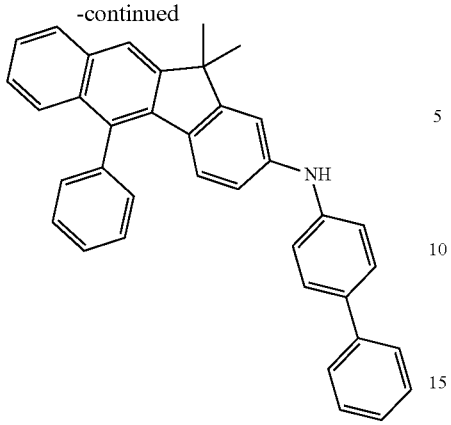

Sub 1-69

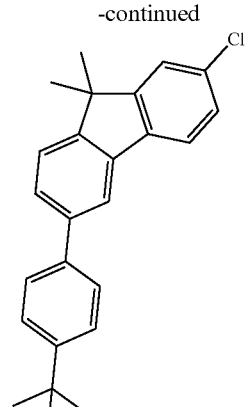

Sub 1-74 int.

1) Synthesis of Sub 1-69A

After dissolving Sub 1-69a (50.0 g, 139.8 mmol) with THF (699 ml) in a round bottom flask, Sub 1-11aa (17.0 g, 139.8 mmol), Pd(PPh$_3$)$_4$ (9.7 g, 8.4 mmol), NaOH (16.8 g, 419.4 mmol) and water (349 mL) were added and 40.0 g of product was obtained by performing the same experiment as Sub 1-11A. (Yield: 80.6%)

2) Synthesis of Sub 1-69

In a round bottom flask, Sub 1-69A (40.0 g, 112.7 mmol) obtained in the above synthesis and Sub 1-69B (18.4 g, 112.7 mmol), Pd$_2$(dba)$_3$ (3.1 g, 3.4 mmol), P(t-Bu)$_3$ (1.4 g, 6.8 mmol), NaOt-Bu (21.7 g, 225.4 mmol), toluene (564 mL) were tested in the same manner as for Sub 1-11, and 39.3 g of product was obtained. (Yield: 71.5%)

4. Synthesis Example of Sub 1-74

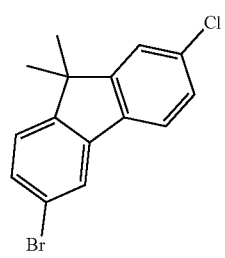

Sub 1-74a

+

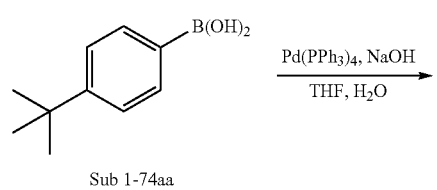

Sub 1-74aa $\xrightarrow{\text{Pd(PPh}_3)_4, \text{NaOH}}_{\text{THF, H}_2\text{O}}$

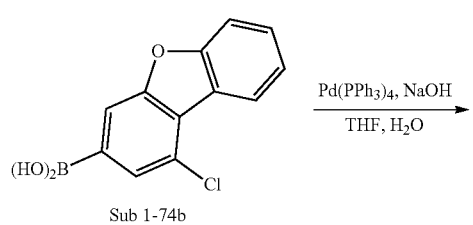

Sub 1-74b $\xrightarrow{\text{Pd(PPh}_3)_4, \text{NaOH}}_{\text{THF, H}_2\text{O}}$

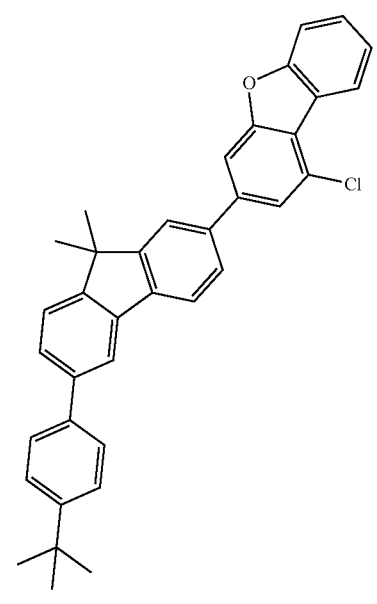

Sub 1-74A

+

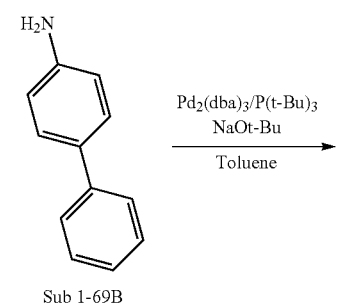

Sub 1-69B $\xrightarrow{\text{Pd}_2(\text{dba})_3/\text{P(t-Bu)}_3 \;\; \text{NaOt-Bu}}_{\text{Toluene}}$ -continued

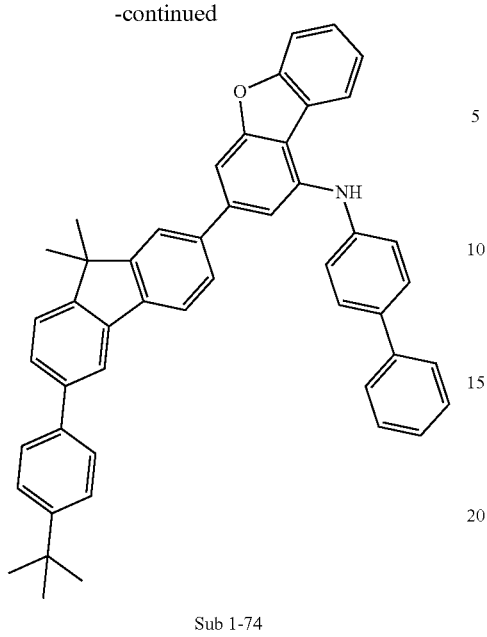

Sub 1-74

1) Synthesis of Sub 1-74 int.

After dissolving Sub 1-74a (50.0 g, 162.5 mmol) with THF (813 ml) in a round bottom flask, Sub 1-74aa (28.9 g, 162.5 mmol), Pd(PPh$_3$)$_4$ (11.3 g, 9.8 mmol), NaOH (19.5 g, 487.6 mmol) and water (406 mL) were added and 48.5 g of product was obtained by performing the same experiment as Sub 1-11A. (Yield: 82.7%)

2) Synthesis of Sub 1-74A

After dissolving Sub 1-74 int. (48.5 g, 134.4 mmol) with THF (672 ml) in a round bottom flask, Sub 1-74ab (33.1 g, 134.4 mmol), Pd(PPh$_3$)$_4$ (9.3 g, 8.1 mmol), NaOH (16.1 g, 403.1 mmol) and water (336 mL) were added and 38.2 g of product was obtained by performing the same experiment as Sub 1-11A. (Yield: 53.9%)

3) Synthesis of Sub 1-74

In a round bottom flask, Sub 1-74A (38.2 g, 72.5 mmol) obtained in the above synthesis and Sub 1-69B (11.8 g, 72.5 mmol), Pd$_2$(dba)$_3$ (2.0 g, 2.2 mmol), P(t-Bu)$_3$ (1.0 g, 4.4 mmol), NaOt-Bu (13.9 g, 144.9 mmol), toluene (362 mL) were tested in the same manner as for Sub 1-11, and 33.7 g of product was obtained. (Yield: 70.5%)

5. Synthesis Example of Sub 1-95

Sub 1-95a

-continued

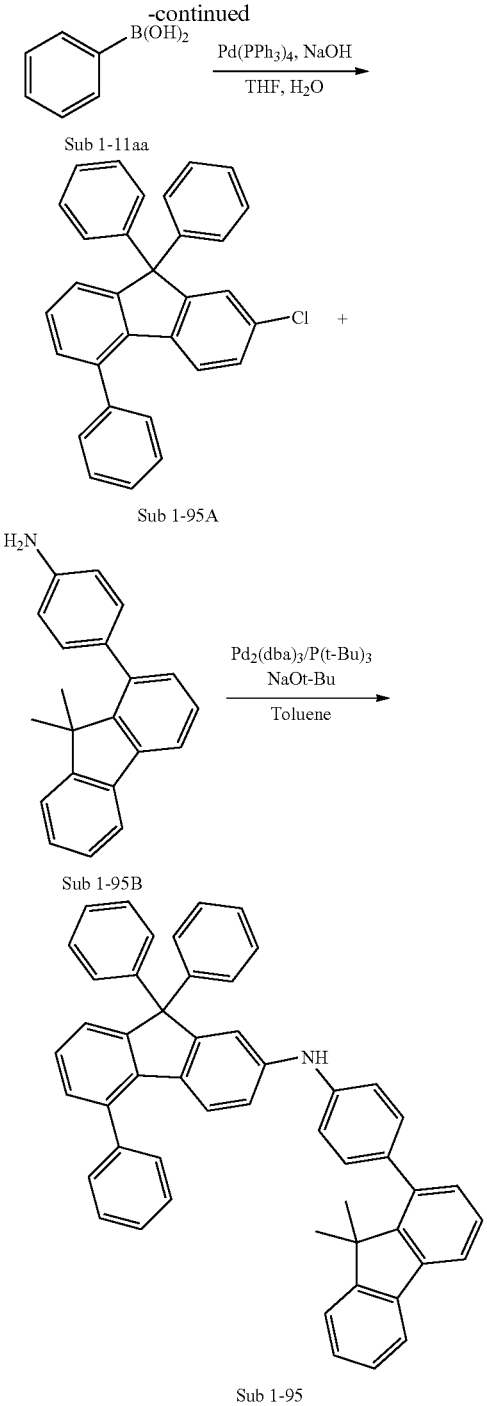

1) Synthesis of Sub 1-95A

After dissolving Sub 1-95a (50.0 g, 115.8 mmol) with THF (579 ml) in a round bottom flask, Sub 1-11aa (17.0 g, 115.8 mmol), Pd(PPh$_3$)$_4$ (8.0 g, 7.0 mmol), NaOH (13.9 g, 347.4 mmol) and water (290 mL) were added and 40.3 g of product was obtained by performing the same experiment as Sub 1-11A. (Yield: 81.1%)

2) Synthesis of Sub 1-95

In a round bottom flask, Sub 1-95A (40.3 g, 93.9 mmol) obtained in the above synthesis and Sub 1-95B (25.9 g, 93.9 mmol), Pd₂(dba)₃ (2.6 g, 2.8 mmol), P(t-Bu)₃ (1.1 g, 5.6 mmol), NaOt-Bu (18.1 g, 187.9 mmol), toluene (470 mL) were tested in the same manner as for Sub 1-11, and 46.0 g of product was obtained. (Yield: 72.3%)
The compounds belonging to Sub 1 may be the following compounds, but are not limited to, and Table 1 shows the FD-MS (Field Desorption-Mass Spectrometry) values of the compounds belonging to Sub 1.
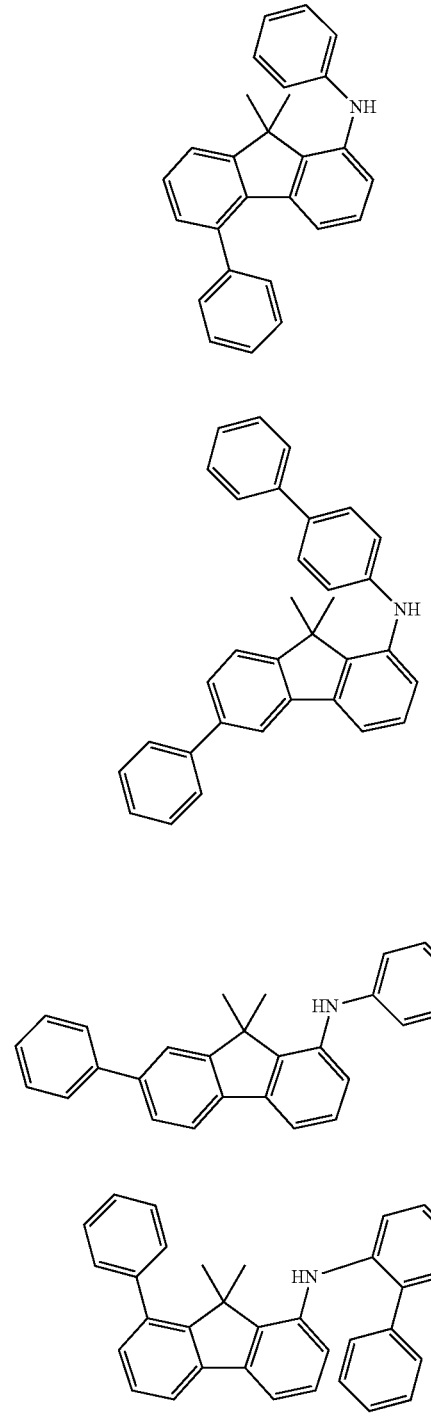
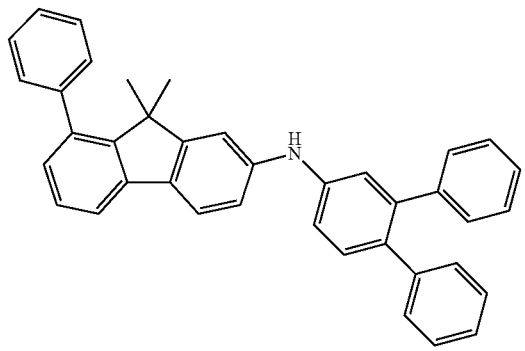

Sub 1-9
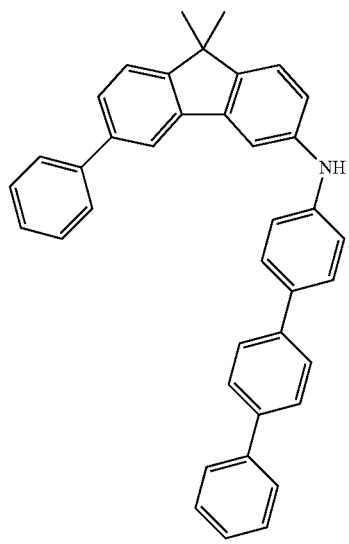
Sub 1-10
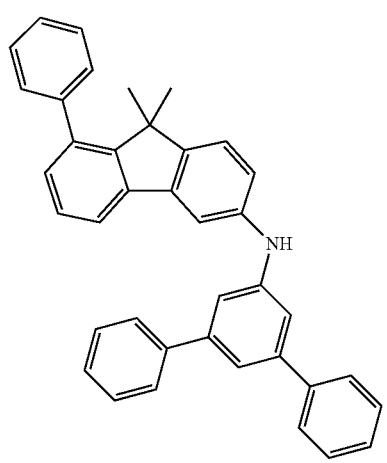
Sub 1-11
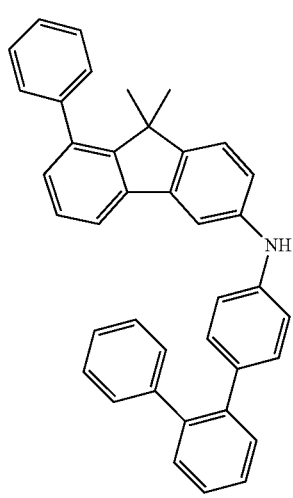
Sub 1-12
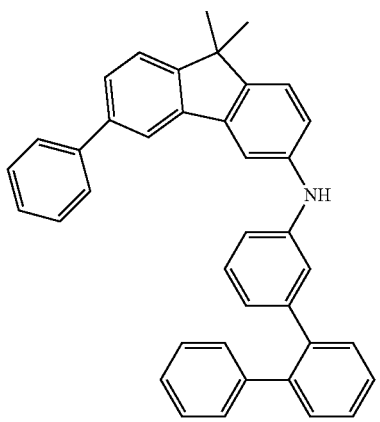
Sub 1-13
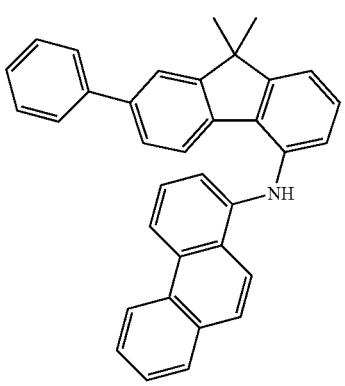
Sub 1-14
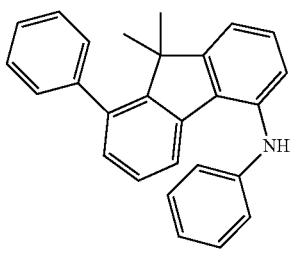
Sub 1-15
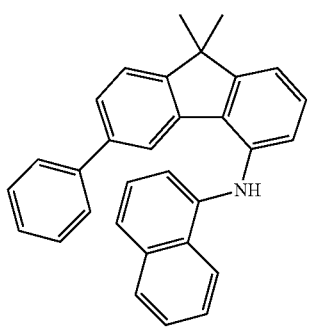

Sub 1-16
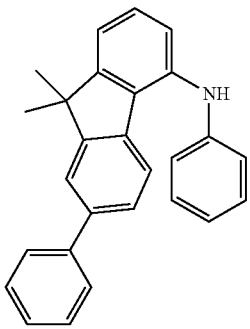
Sub 1-17
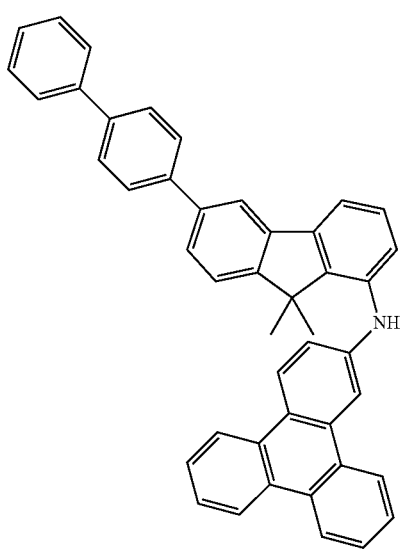
Sub 1-18
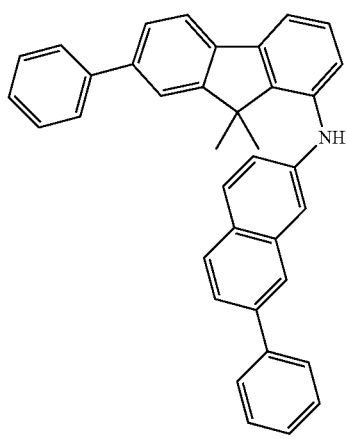
Sub 1-19
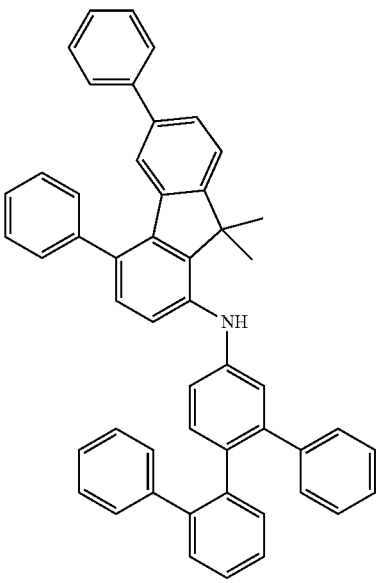
Sub 1-20
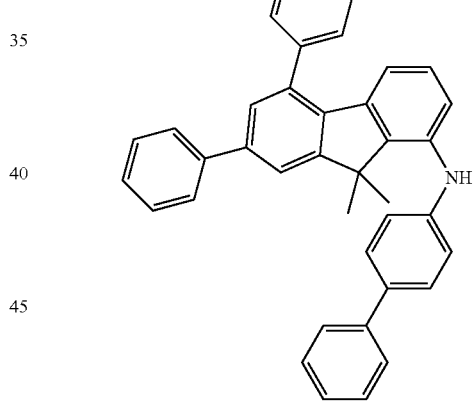
Sub 1-21
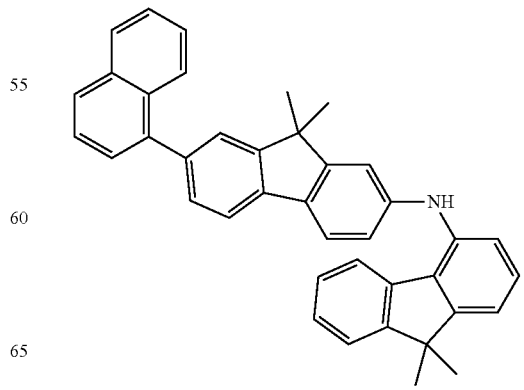

-continued
Sub 1-22
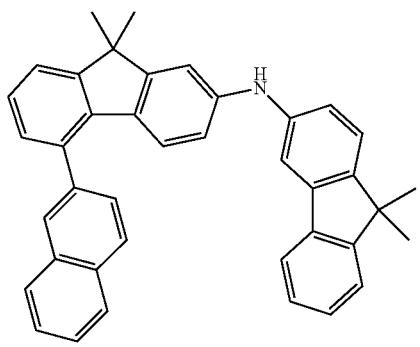
Sub 1-23
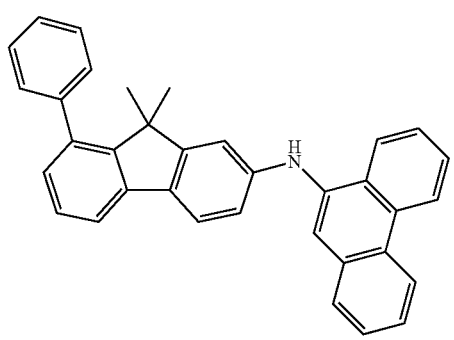
Sub 1-24
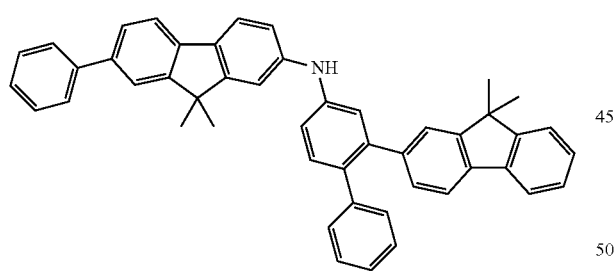
Sub 1-25
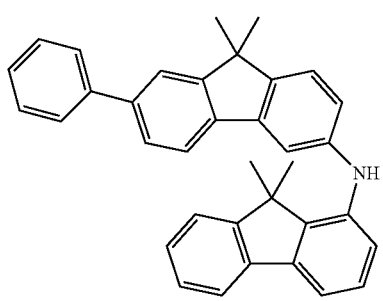
Sub 1-26
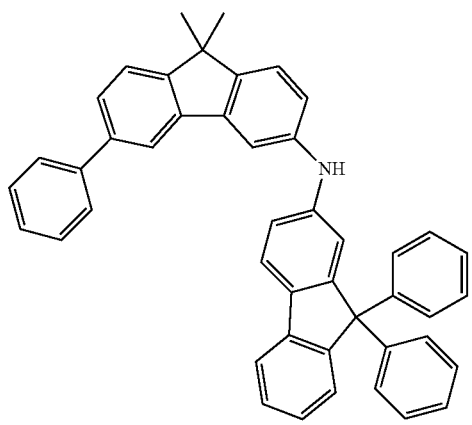
Sub 1-27
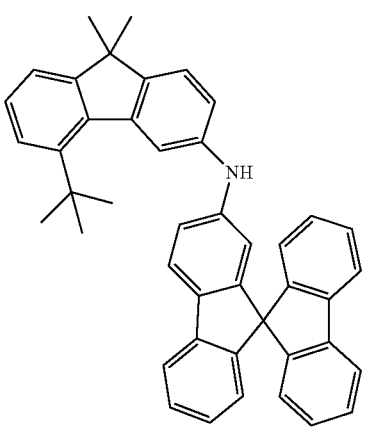
Sub 1-28
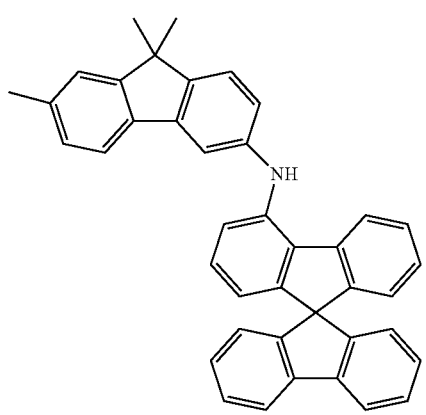

-continued
Sub 1-29
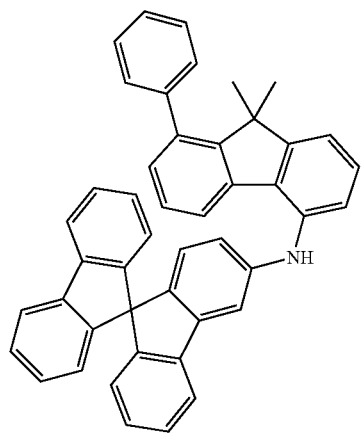
Sub 1-30
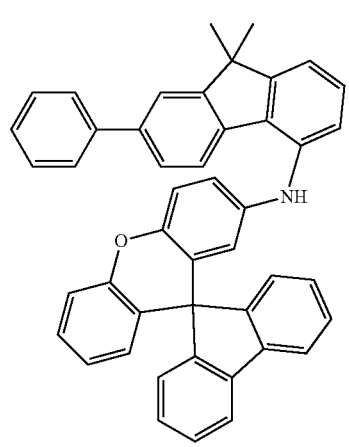
Sub 1-31
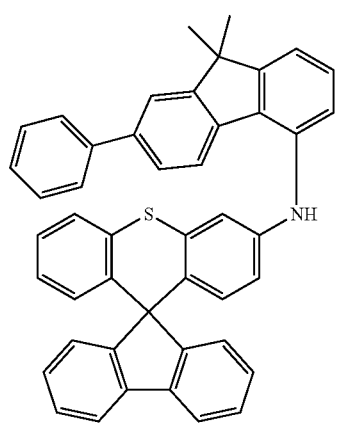
Sub 1-32
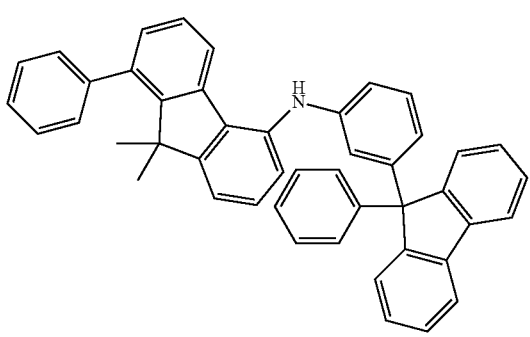
-continued
Sub 1-33
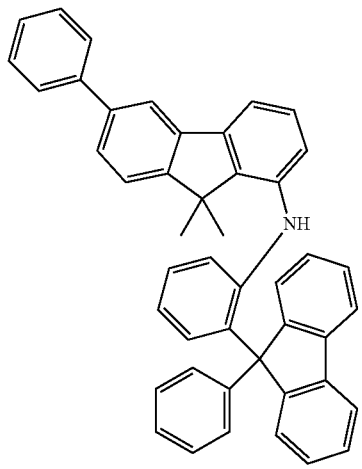
Sub 1-34
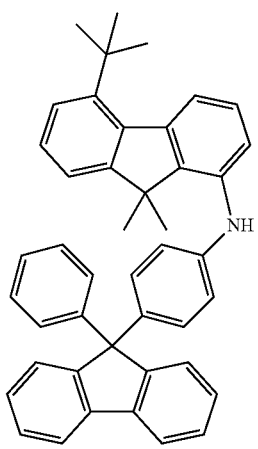
Sub 1-35
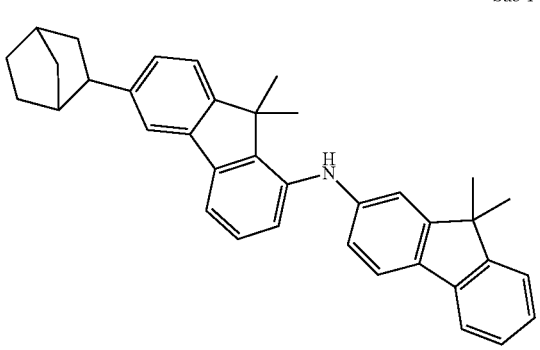
Sub 1-36
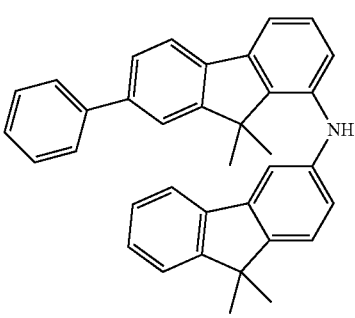

-continued
Sub 1-37
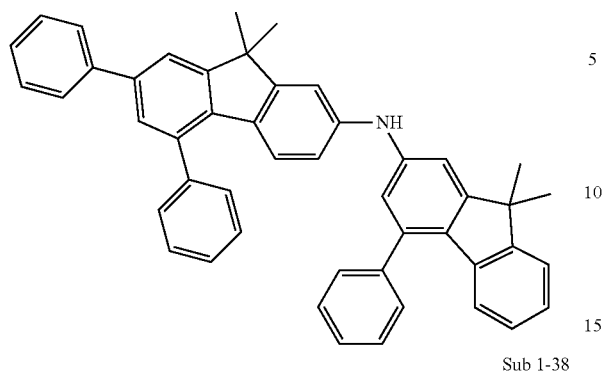
Sub 1-38
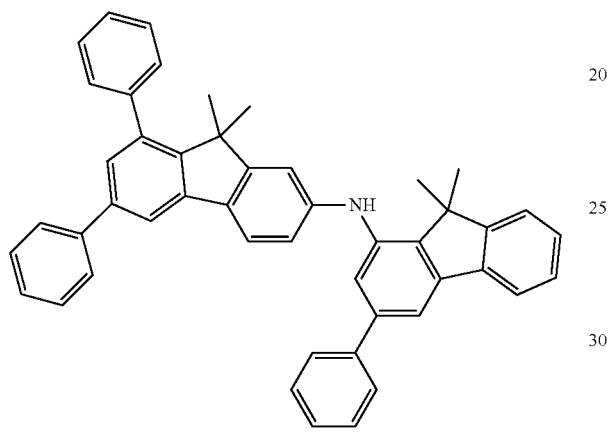
Sub 1-39
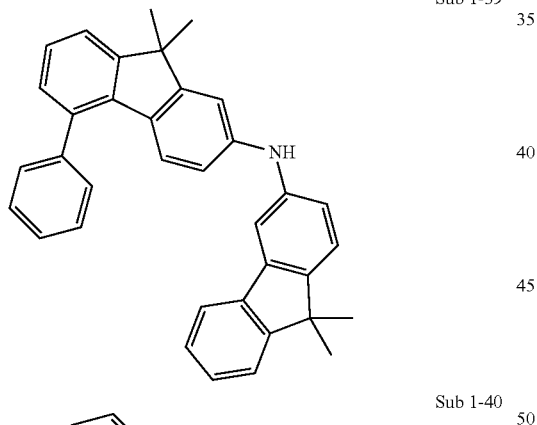
Sub 1-40
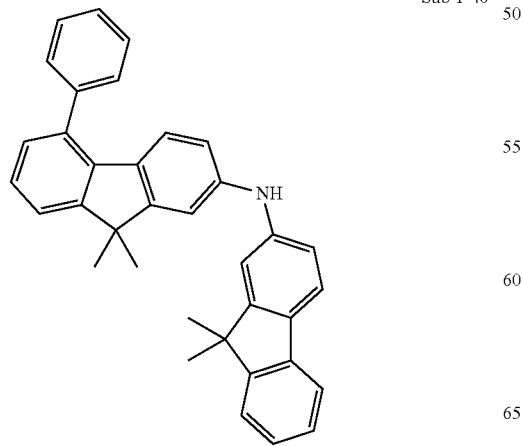
-continued
Sub 1-41
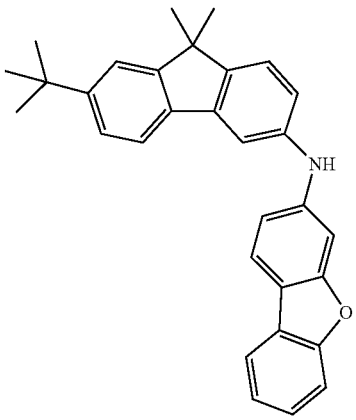
Sub 1-42
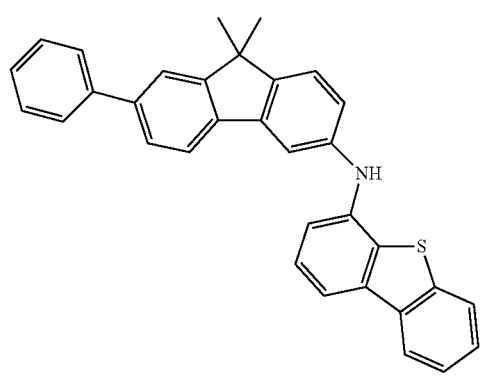
Sub 1-43
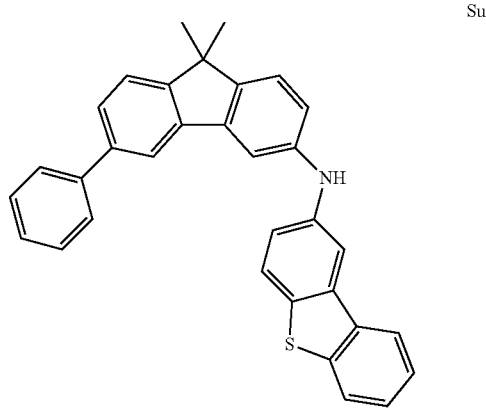
Sub 1-44
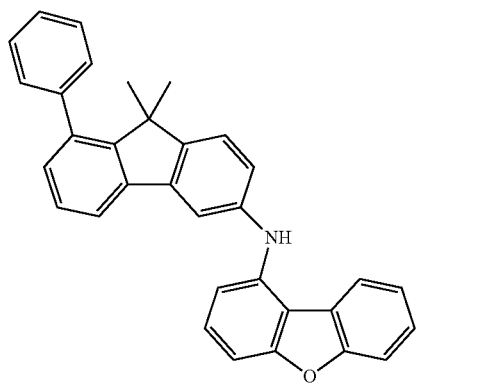

Sub 1-45
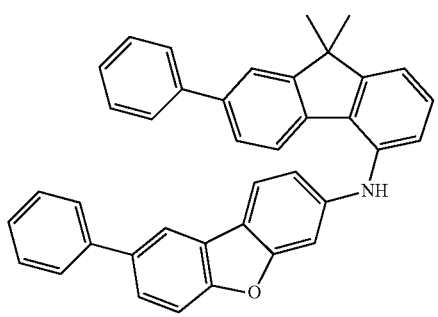
Sub 1-46
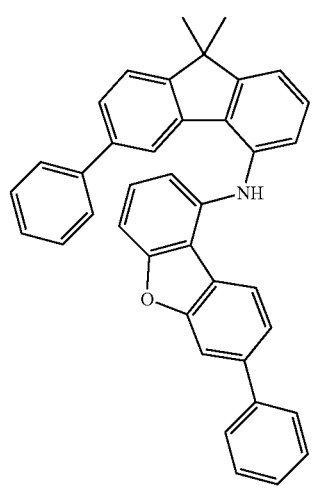
Sub 1-47
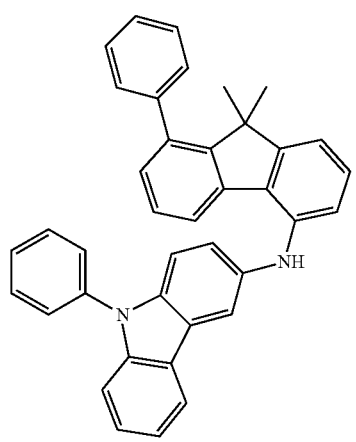
Sub 1-48
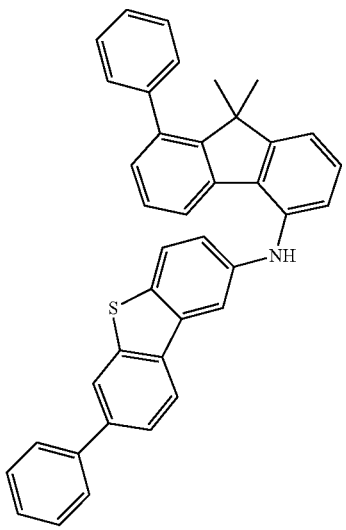
Sub 1-49
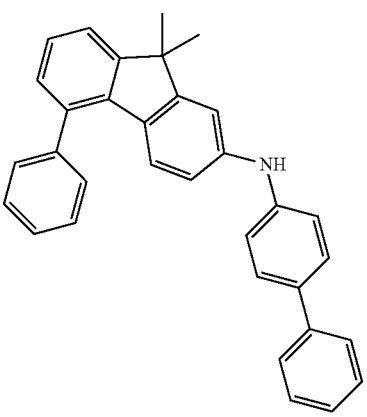
Sub 1-50
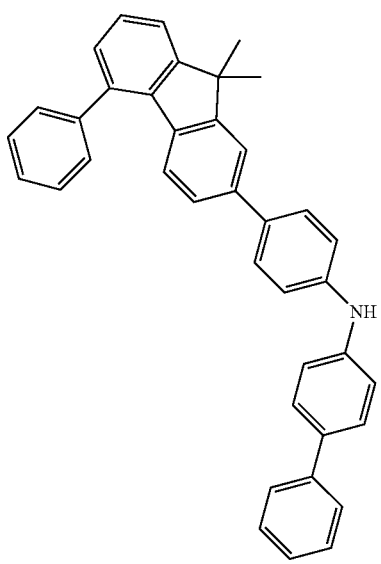

Sub 1-51
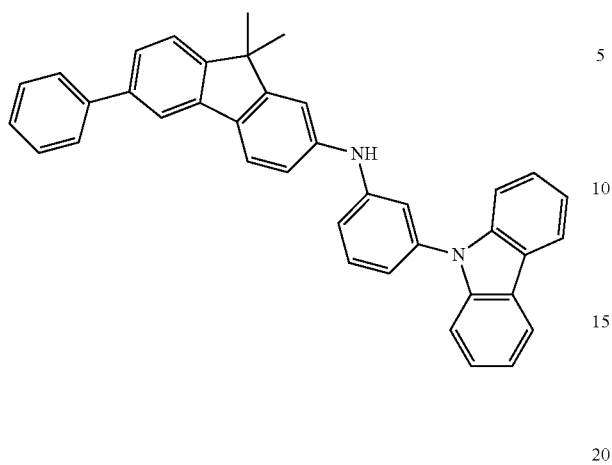
Sub 1-54
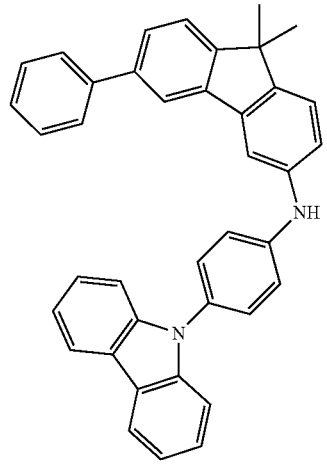
Sub 1-52
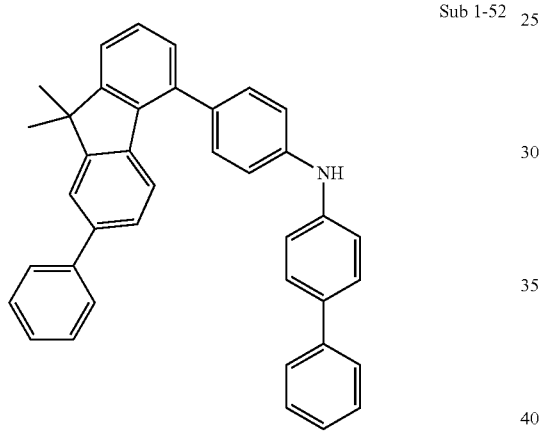
Sub 1-55
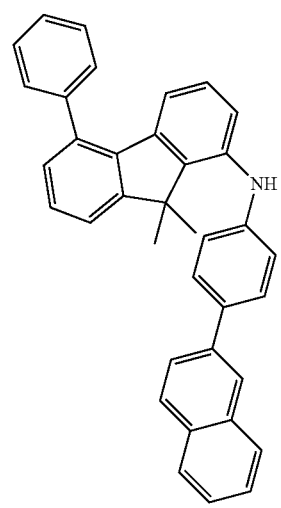
Sub 1-53
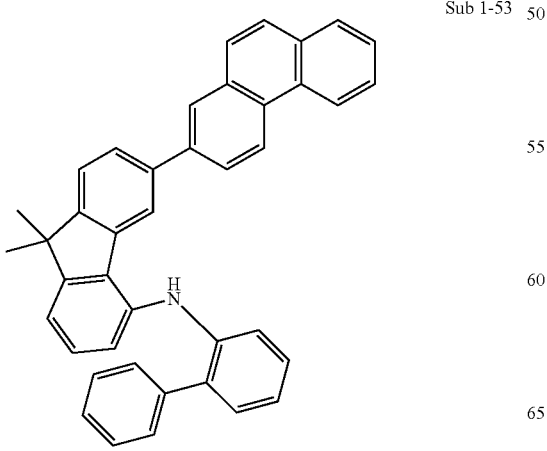
Sub 1-56
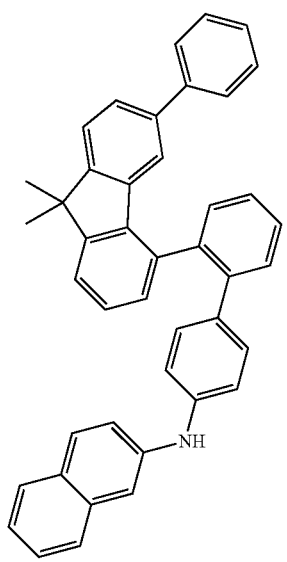

-continued
Sub 1-57
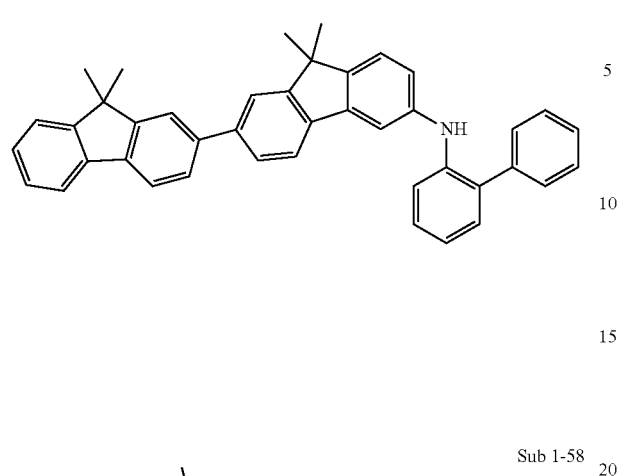
Sub 1-58
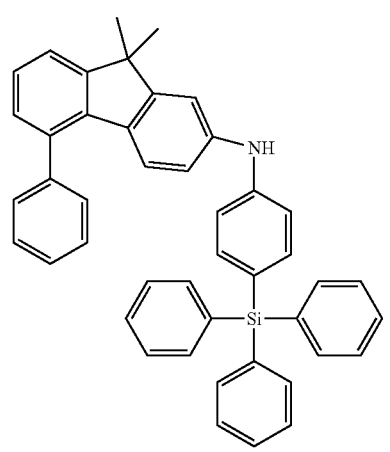
Sub 1-59
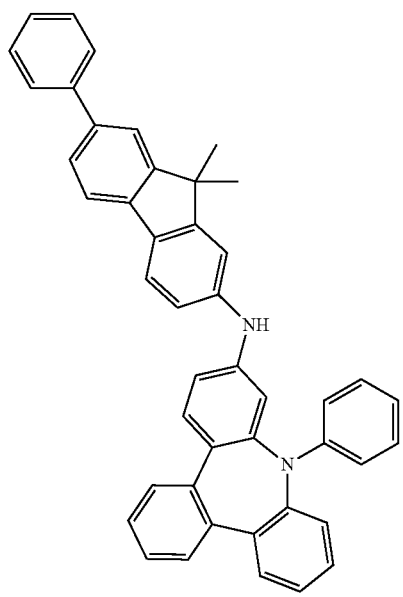
-continued
Sub 1-60
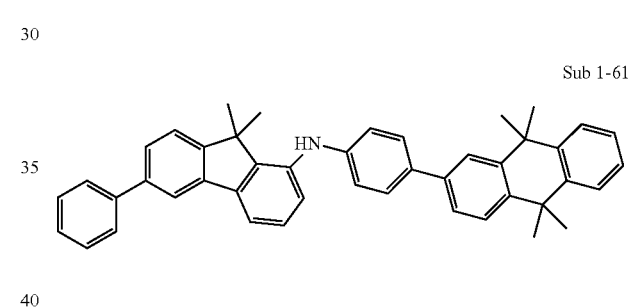
Sub 1-61
Sub 1-62
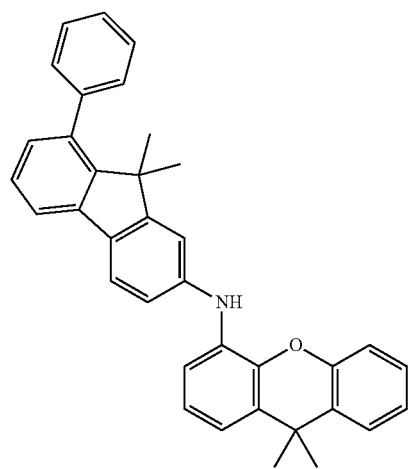

Sub 1-63
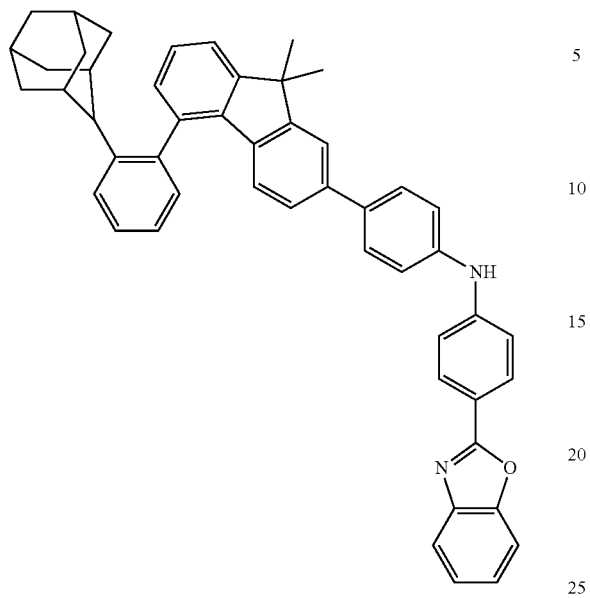
Sub 1-66
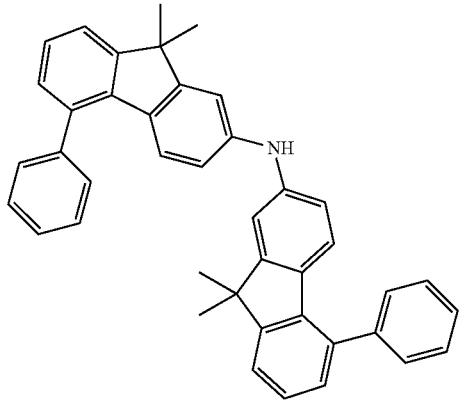
Sub 1-64
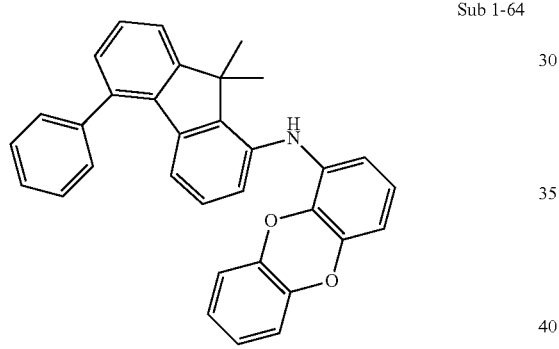
Sub 1-67
Sub 1-65
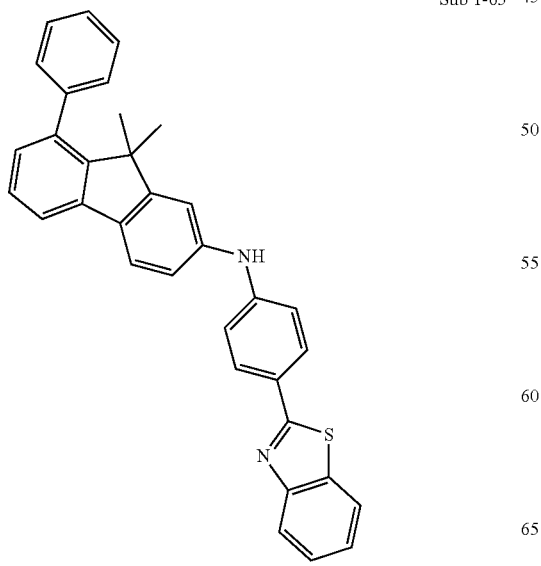
Sub 1-68
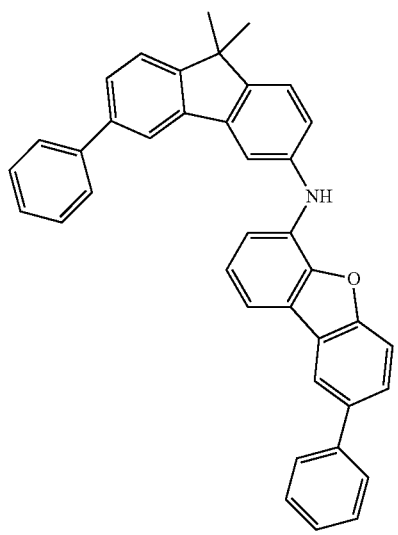

Sub 1-69
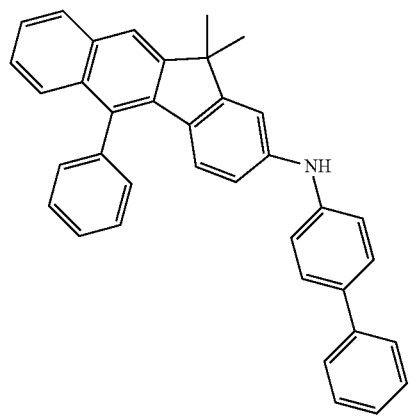
Sub 1-70
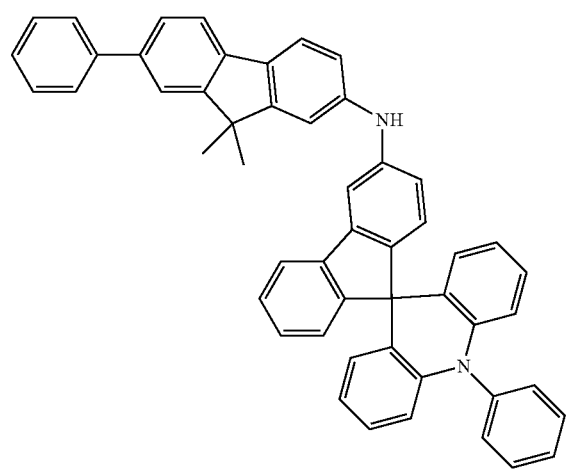
Sub 1-71
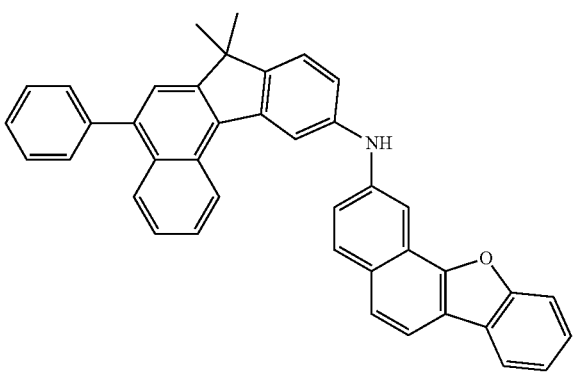
Sub 1-72
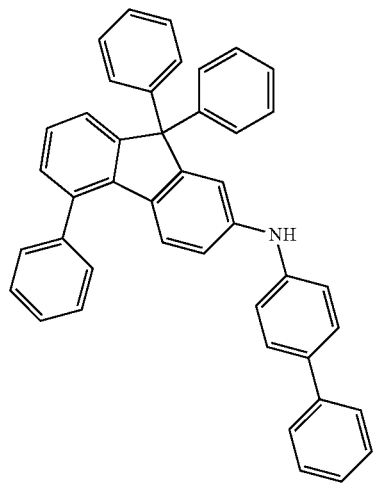
Sub 1-73
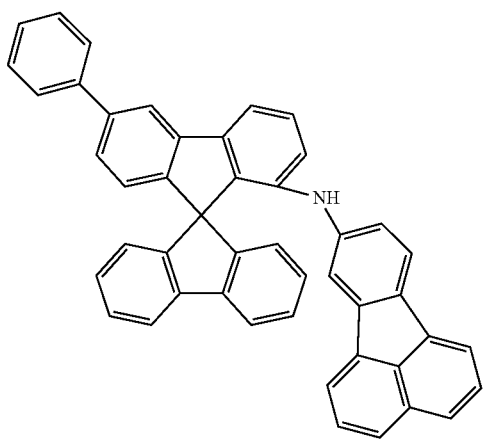
Sub 1-74
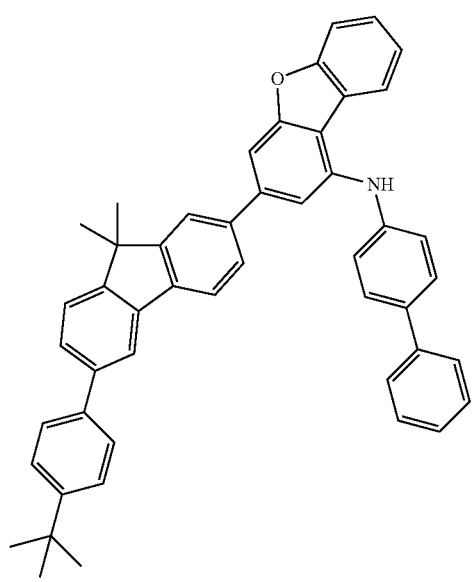

Sub 1-75
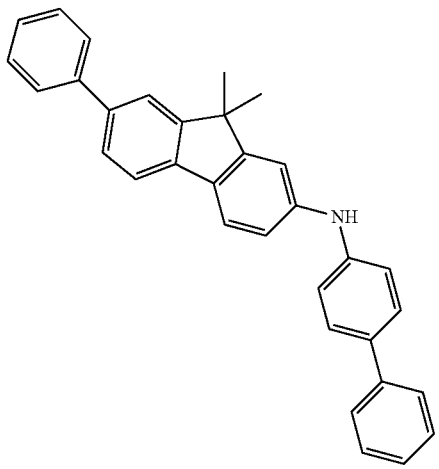
Sub 1-76
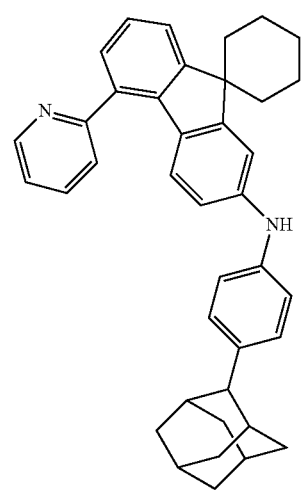
Sub 1-77
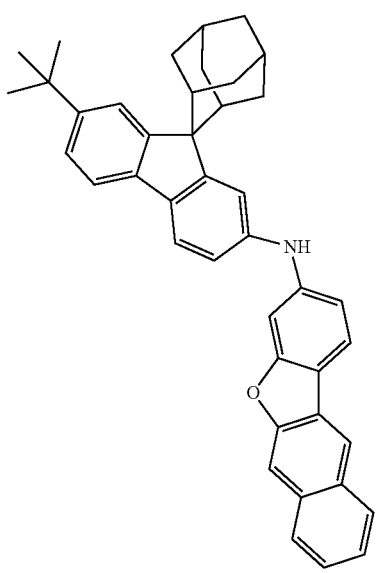
Sub 1-78
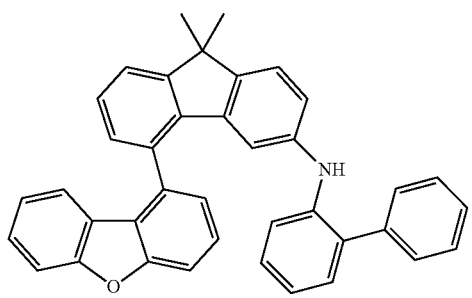
Sub 1-79
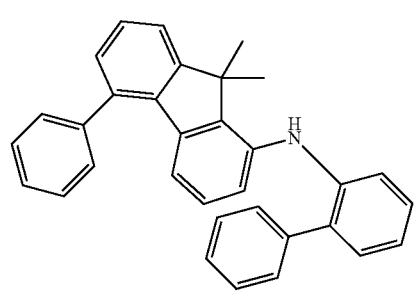
Sub 1-80
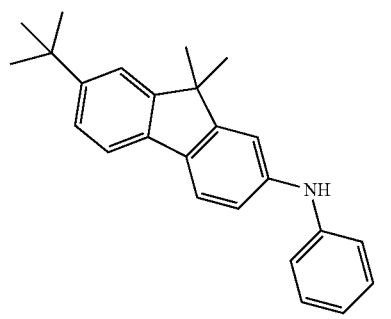
Sub 1-81
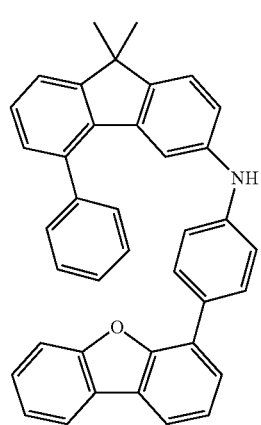

Sub 1-82
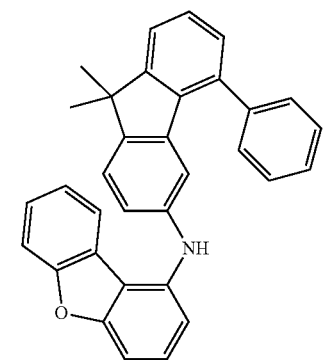
Sub 1-83
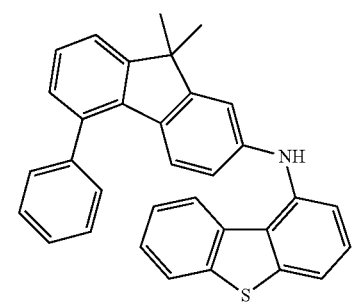
Sub 1-84
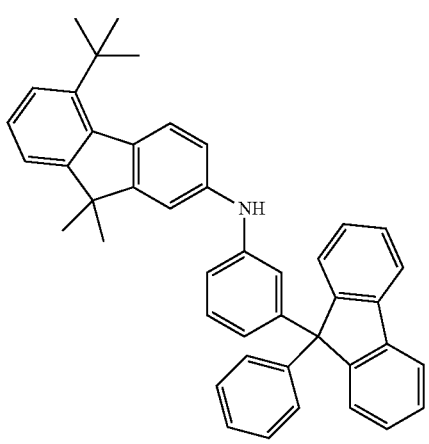
Sub 1-85
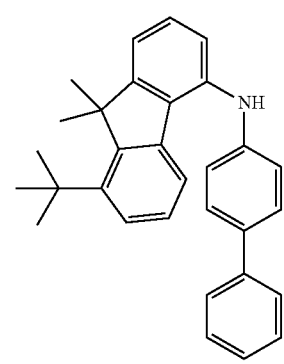
Sub 1-86
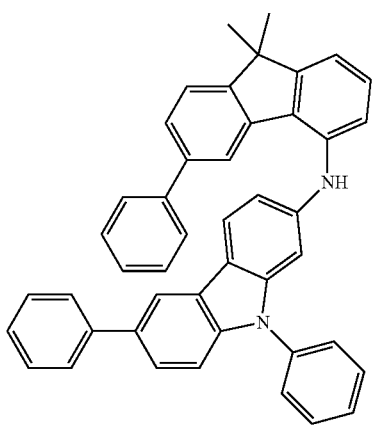
Sub 1-87
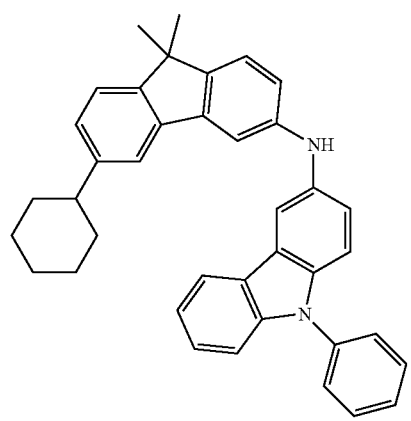
Sub 1-88
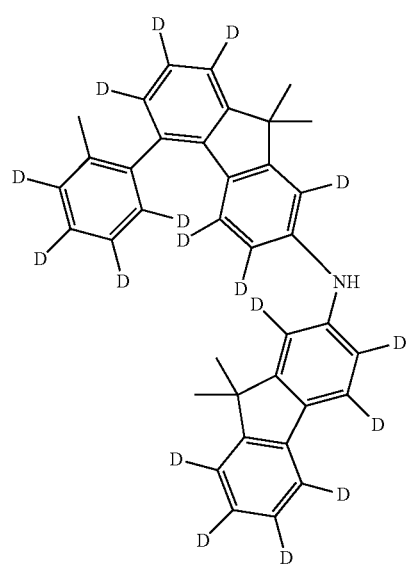

Sub 1-89
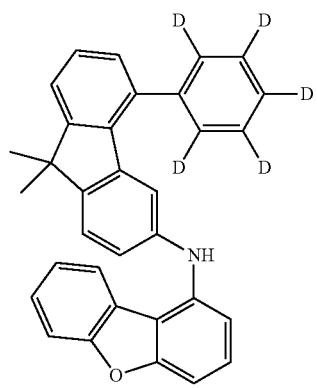
Sub 1-90
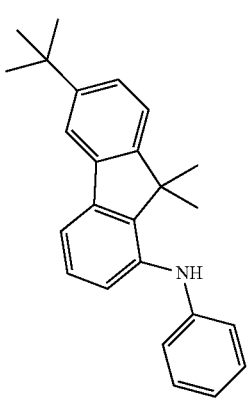
Sub 1-91
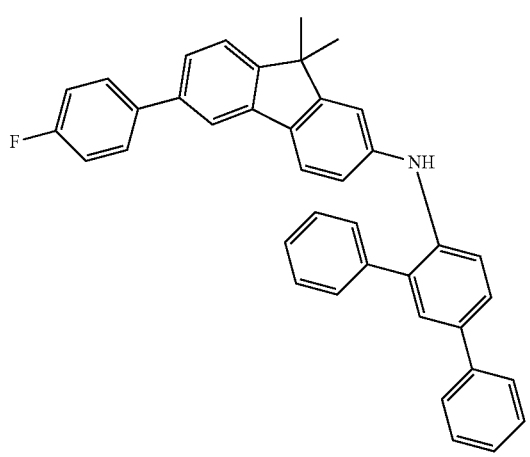
Sub 1-92
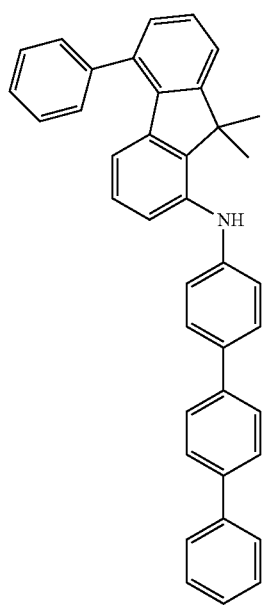
Sub 1-93
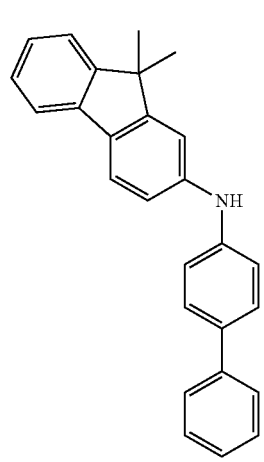
Sub 1-94
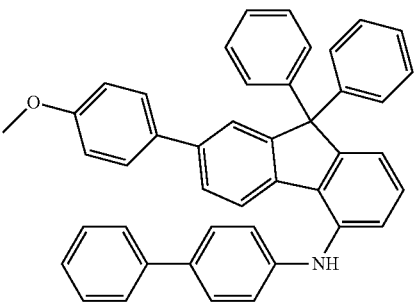

Sub 1-95
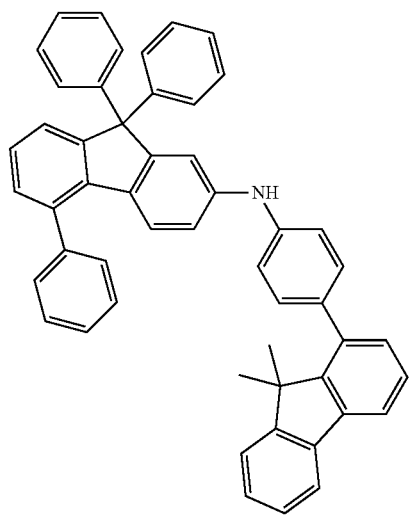
Sub 1-96
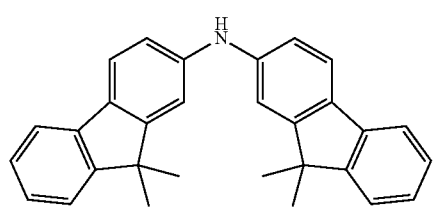
Sub 1-97
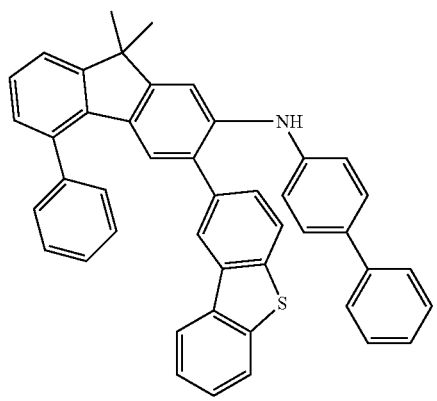
Sub 1-98
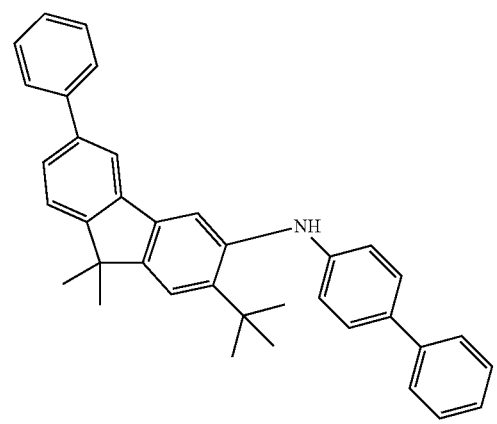
Sub 1-99
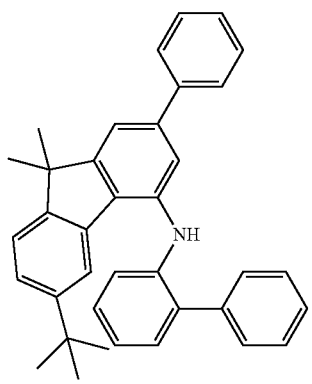
Sub 1-100
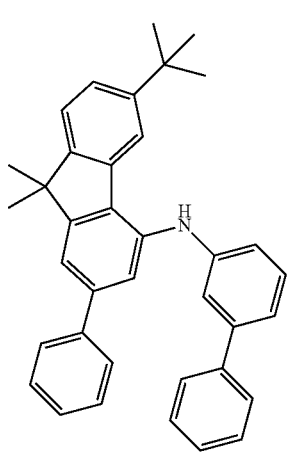
Sub 1-101
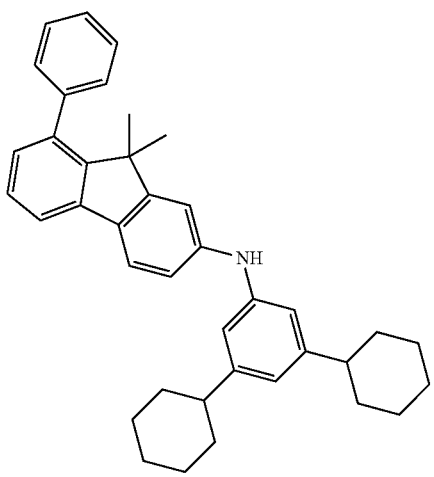

Sub 1-102
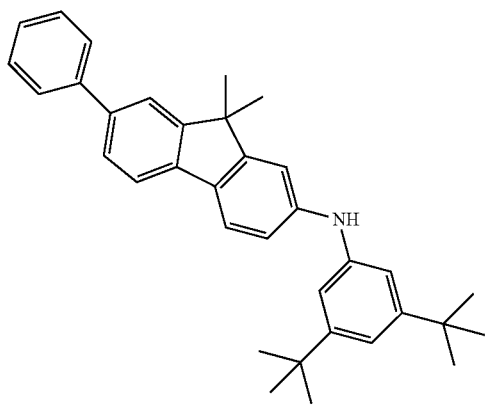
Sub 1-103
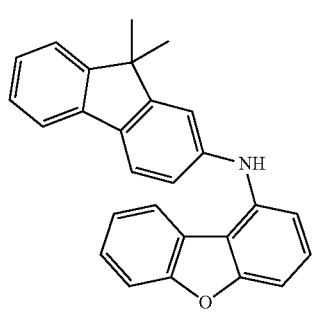
Sub 1-104
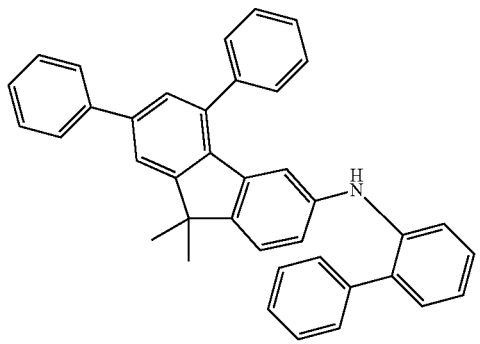
Sub 1-105
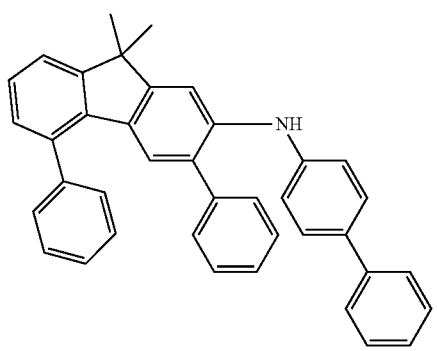
Sub 1-106
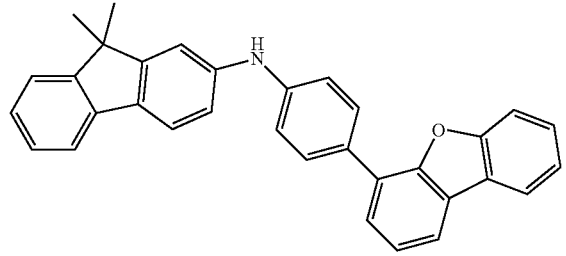
Sub 1-107
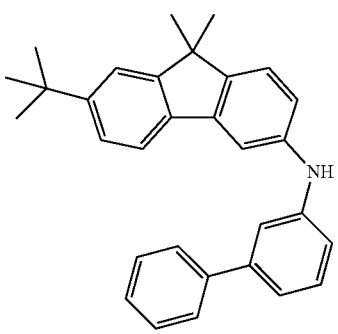
Sub 1-108
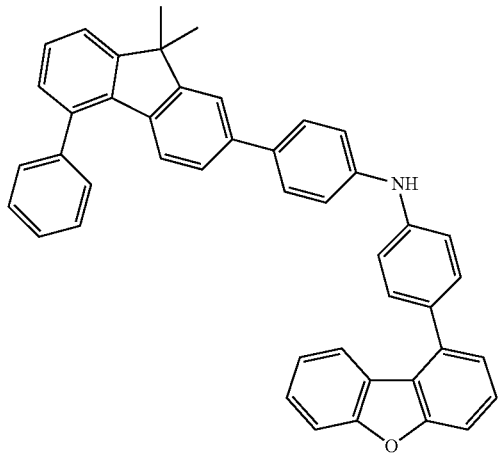
Sub 1-109
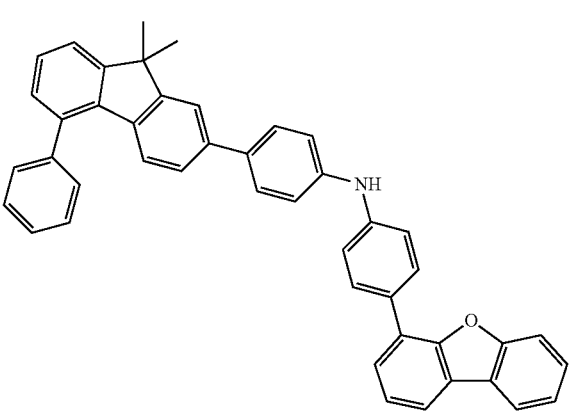

Sub 1-110
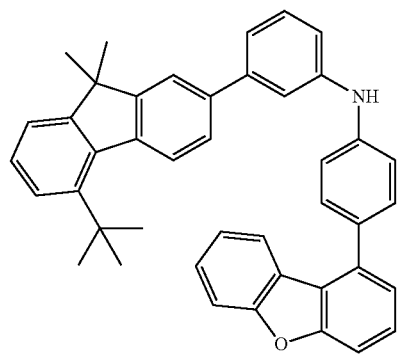
Sub 1-111
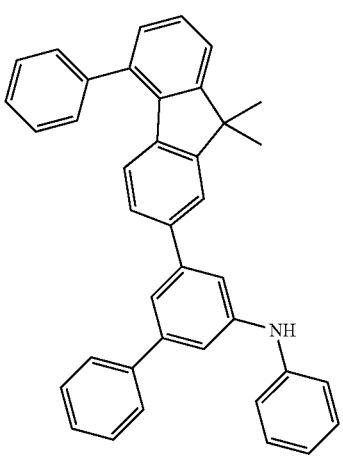
Sub 1-112
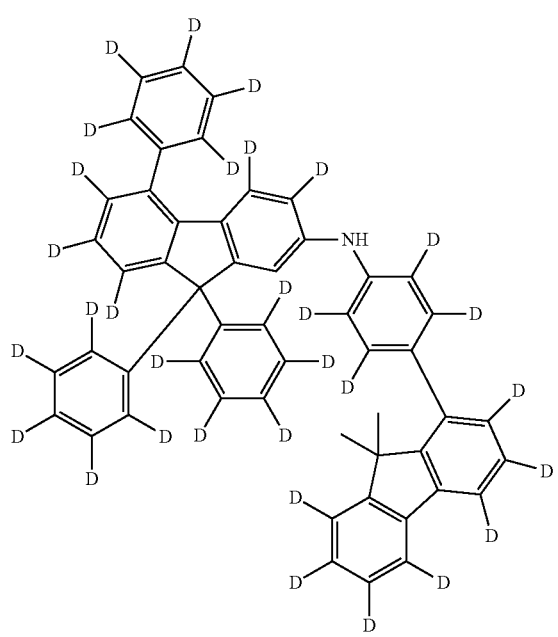
Sub 1-113
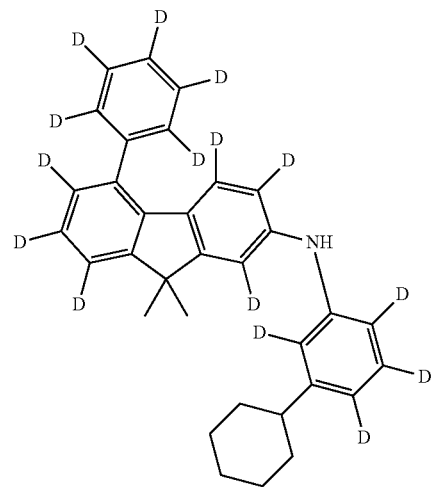
Sub 1-114
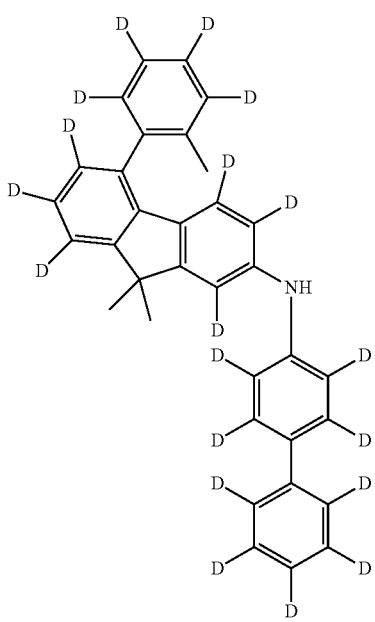
Sub 1-115
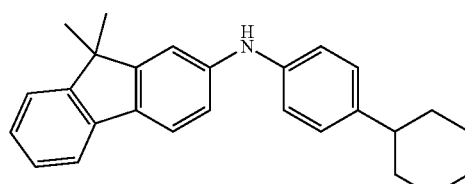
Sub 1-116
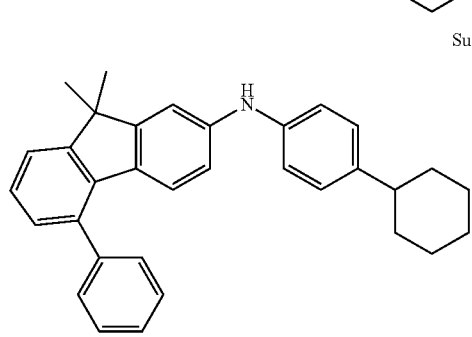

Sub 1-117
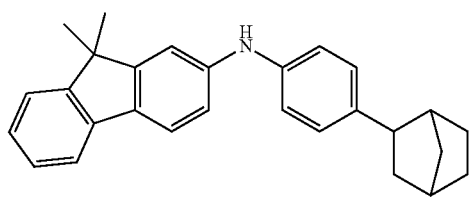
Sub 1-118
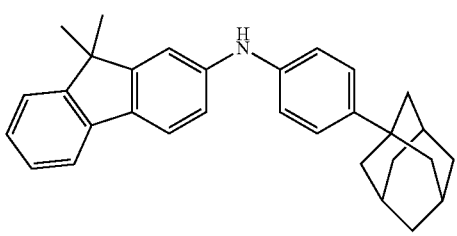
Sub 1-119
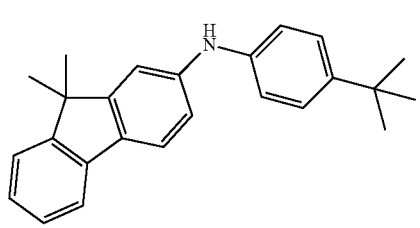
Sub 1-120
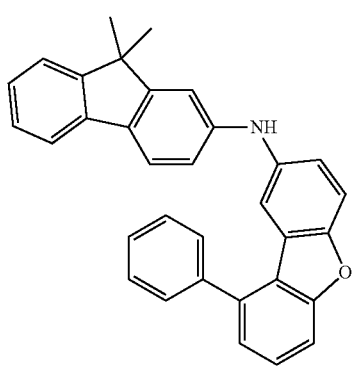
Sub 1-121
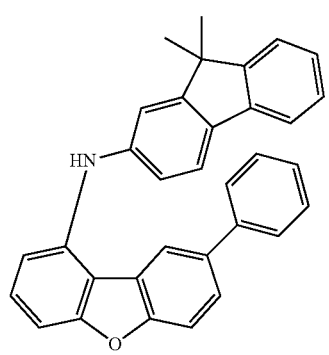
Sub 1-122
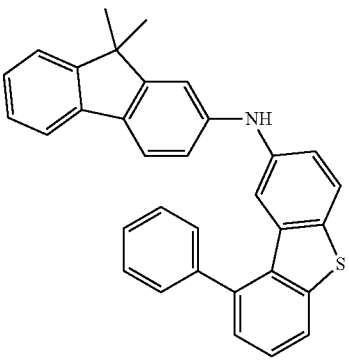
Sub 1-123
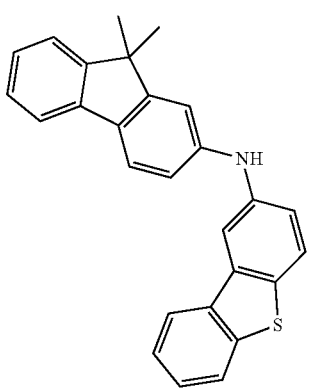
Sub 1-124
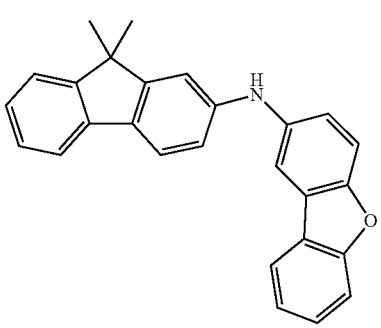
Sub 1-125
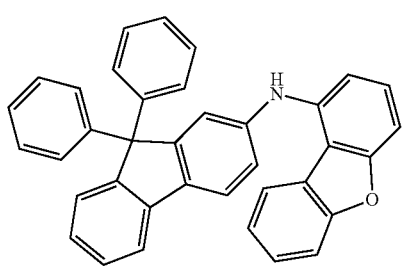

-continued
Sub 1-126
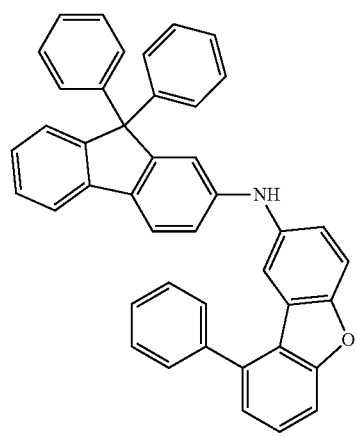
Sub 1-127
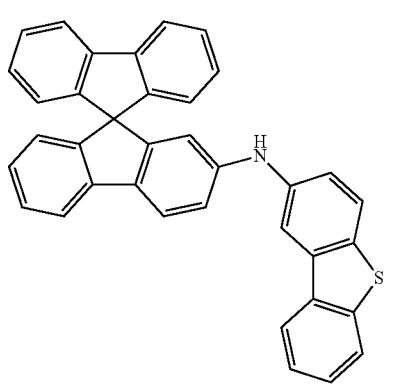
Sub 1-128
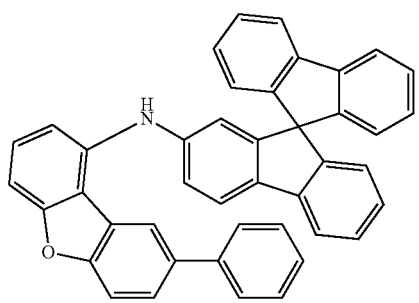
Sub 1-129
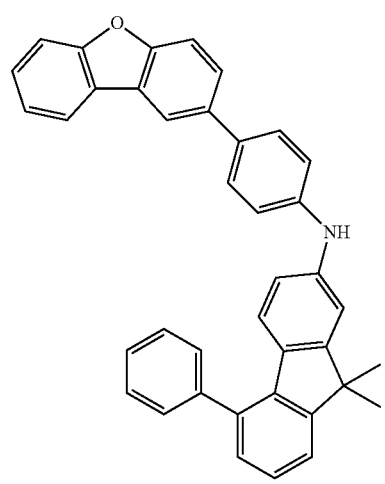
-continued
Sub 1-130
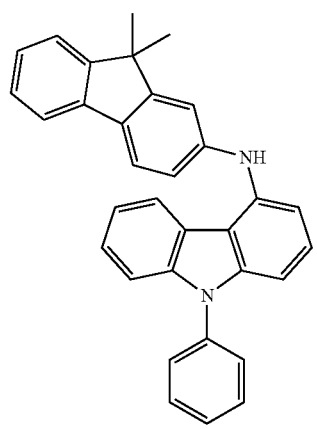
Sub 1-131
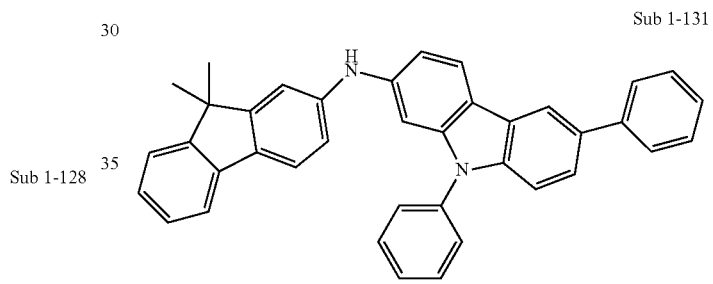
Sub 1-132
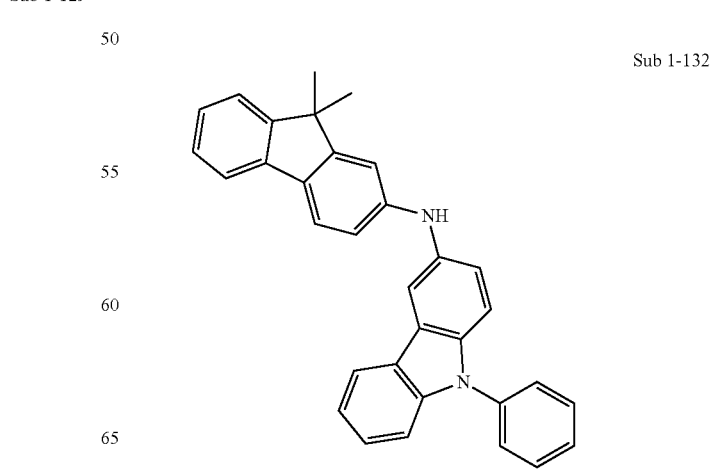

TABLE 1

| compound | FD-MS | compound | FD-MS |
| --- | --- | --- | --- |
| Sub 1-1 | m/z = 361.18($C_{27}H_{23}N$ = 361.49) | Sub 1-2 | m/z = 437.21($C_{33}H_{27}N$ = 437.59) |
| Sub 1-3 | m/z = 437.21($C_{33}H_{27}N$ = 437.59) | Sub 1-4 | m/z = 437.21($C_{33}H_{27}N$ = 437.59) |
| Sub 1-5 | m/z = 513.25($C_{39}H_{31}N$ = 513.68) | Sub 1-6 | m/z = 563.26($C_{43}H_{33}N$ = 563.74) |
| Sub 1-7 | m/z = 487.23($C_{37}H_{29}N$ = 487.65) | Sub 1-8 | m/z = 437.21($C_{33}H_{27}N$ = 437.59) |
| Sub 1-9 | m/z = 513.25($C_{39}H_{31}N$ = 513.68) | Sub 1-10 | m/z = 513.25($C_{39}H_{31}N$ = 513.68) |
| Sub 1-11 | m/z = 513.25($C_{39}H_{31}N$ = 513.68) | Sub 1-12 | m/z = 513.25($C_{39}H_{31}N$ = 513.68) |
| Sub 1-13 | m/z = 461.21($C_{35}H_{27}N$ = 461.61) | Sub 1-14 | m/z = 361.18($C_{27}H_{23}N$ = 361.49) |
| Sub 1-15 | m/z = 411.20($C_{31}H_{25}N$ = 411.55) | Sub 1-16 | m/z = 361.18($C_{27}H_{23}N$ = 361.49) |
| Sub 1-17 | m/z = 587.26($C_{45}H_{33}N$ = 587.77) | Sub 1-18 | m/z = 487.23($C_{37}H_{29}N$ = 487.65) |
| Sub 1-19 | m/z = 665.31($C_{51}H_{39}N$ = 665.88) | Sub 1-20 | m/z = 513.25($C_{39}H_{31}N$ = 513.68) |
| Sub 1-21 | m/z = 527.26($C_{40}H_{33}N$ = 527.71) | Sub 1-22 | m/z = 527.26($C_{40}H_{33}N$ = 527.71) |
| Sub 1-23 | m/z = 461.21($C_{35}H_{27}N$ = 461.61) | Sub 1-24 | m/z = 629.31($C_{48}H_{39}N$ = 629.85) |
| Sub 1-25 | m/z = 477.25($C_{36}H_{31}N$ = 477.65) | Sub 1-26 | m/z = 601.28($C_{46}H_{35}N$ = 601.79) |
| Sub 1-27 | m/z = 579.29($C_{44}H_{37}N$ = 579.79) | Sub 1-28 | m/z = 537.25($C_{41}H_{31}N$ = 537.71) |
| Sub 1-29 | m/z = 599.26($C_{46}H_{33}N$ = 599.78) | Sub 1-30 | m/z = 615.26($C_{46}H_{33}NO$ = 615.78) |
| Sub 1-31 | m/z = 631.23($C_{46}H_{33}NS$ = 631.84) | Sub 1-32 | m/z = 601.28($C_{46}H_{35}N$ = 601.79) |
| Sub 1-33 | m/z = 601.28($C_{46}H_{35}N$ = 601.79) | Sub 1-34 | m/z = 581.31($C_{44}H_{39}N$ = 581.80) |
| Sub 1-35 | m/z = 495.29($C_{37}H_{37}N$ = 495.71) | Sub 1-36 | m/z = 477.25($C_{36}H_{31}N$ = 477.65) |
| Sub 1-37 | m/z = 629.31($C_{48}H_{39}N$ = 629.85) | Sub 1-38 | m/z = 629.31($C_{48}H_{39}N$ = 629.85) |
| Sub 1-39 | m/z = 477.25($C_{36}H_{31}N$ = 477.65) | Sub 1-40 | m/z = 477.25($C_{36}H_{31}N$ = 477.65) |
| Sub 1-41 | m/z = 431.22($C_{31}H_{29}NO$ = 431.58) | Sub 1-42 | m/z = 467.17($C_{33}H_{25}NS$ = 467.63) |
| Sub 1-43 | m/z = 467.17($C_{33}H_{25}NS$ = 467.63) | Sub 1-44 | m/z = 451.19($C_{33}H_{25}NO$ = 451.57) |
| Sub 1-45 | m/z = 527.22($C_{39}H_{29}NO$ = 527.67) | Sub 1-46 | m/z = 527.20($C_{39}H_{29}NO$ = 527.67) |
| Sub 1-47 | m/z = 526.24($C_{39}H_{30}N_2$ = 526.68) | Sub 1-48 | m/z = 543.22($C_{39}H_{29}NS$ = 543.73) |
| Sub 1-49 | m/z = 437.21($C_{33}H_{27}N$ = 437.59) | Sub 1-50 | m/z = 513.25($C_{39}H_{31}N$ = 513.68) |
| Sub 1-51 | m/z = 526.24($C_{39}H_{30}N_2$ = 526.68) | Sub 1-52 | m/z = 513.25($C_{39}H_{31}N$ = 513.68) |
| Sub 1-53 | m/z = 537.25($C_{41}H_{31}N$ = 537.71) | Sub 1-54 | m/z = 526.24($C_{39}H_{30}N_2$ = 526.68) |
| Sub 1-55 | m/z = 487.23($C_{37}H_{29}N$ = 487.65) | Sub 1-56 | m/z = 563.26($C_{43}H_{33}N$ = 563.74) |
| Sub 1-57 | m/z = 553.28($C_{42}H_{35}N$ = 553.75) | Sub 1-58 | m/z = 619.27($C_{45}H_{37}NSi$ = 619.88) |
| Sub 1-59 | m/z = 602.27($C_{45}H_{34}N_2$ = 602.78) | Sub 1-60 | m/z = 527.22($C_{39}H_{29}NO$ = 527.67) |
| Sub 1-61 | m/z = 595.32($C_{45}H_{41}N$ = 595.83) | Sub 1-62 | m/z = 493.24($C_{36}H_{31}NO$ = 493.65) |
| Sub 1-63 | m/z = 688.35($C_{50}H_{44}N_2O$ = 688.92) | Sub 1-64 | m/z = 467.19($C_{33}H_{25}NO_2$ = 467.57) |
| Sub 1-65 | m/z = 494.18($C_{34}H_{26}N_2S$ = 494.66) | Sub 1-66 | m/z = 553.28($C_{42}H_{35}N$ = 553.75) |
| Sub 1-67 | m/z = 543.20($C_{39}H_{29}NS$ = 543.73) | Sub 1-68 | m/z = 527.22($C_{39}H_{29}NO$ = 527.67) |
| Sub 1-69 | m/z = 487.23($C_{37}H_{29}N$ = 487.65) | Sub 1-70 | m/z = 690.30($C_{52}H_{38}N_2$ = 690.89) |
| Sub 1-71 | m/z = 551.22($C_{41}H_{29}NO$ = 551.69) | Sub 1-72 | m/z = 561.25($C_{43}H_{31}N$ = 561.73) |
| Sub 1-73 | m/z = 607.23($C_{47}H_{29}N$ = 607.76) | Sub 1-74 | m/z = 659.32($C_{49}H_{41}NO$ = 659.87) |
| Sub 1-75 | m/z = 437.21($C_{33}H_{27}N$ = 437.59) | Sub 1-76 | m/z = 536.32($C_{39}H_{40}N_2$ = 536.76) |
| Sub 1-77 | m/z = 573.30($C_{42}H_{39}NO$ = 573.78) | Sub 1-78 | m/z = 527.22($C_{39}H_{29}NO$ = 527.67) |
| Sub 1-79 | m/z = 437.21($C_{33}H_{27}N$ = 437.59) | Sub 1-80 | m/z = 341.21($C_{25}H_{27}N$ = 341.50) |
| Sub 1-81 | m/z = 527.22($C_{39}H_{29}NO$ = 527.67) | Sub 1-82 | m/z = 451.19($C_{33}H_{25}NO$ = 451.57) |
| Sub 1-83 | m/z = 467.17($C_{33}H_{25}NS$ = 467.63) | Sub 1-84 | m/z = 581.31($C_{44}H_{39}N$ = 581.80) |
| Sub 1-85 | m/z = 417.25($C_{31}H_{31}N$ = 417.60) | Sub 1-86 | m/z = 602.27($C_{45}H_{34}N_2$ = 602.78) |
| Sub 1-87 | m/z = 532.29($C_{39}H_{36}N_2$ = 532.73) | Sub 1-88 | m/z = 508.37($C_{37}H_{16}D_{17}N$ = 508.78) |
| Sub 1-89 | m/z = 456.22($C_{33}H_{20}D_5NO$ = 456.60) | Sub 1-90 | m/z = 341.21($C_{25}H_{27}N$ = 341.50) |
| Sub 1-91 | m/z = 531.24($C_{39}H_{30}FN$ = 531.67) | Sub 1-92 | m/z = 513.25($C_{39}H_{31}N$ = 513.68) |
| Sub 1-93 | m/z = 361.18($C_{27}H_{23}N$ = 361.49) | Sub 1-94 | m/z = 591.26($C_{44}H_{33}NO$ = 591.75) |
| Sub 1-95 | m/z = 677.31($C_{52}H_{39}N$ = 677.89) | Sub 1-96 | m/z = 401.21($C_{30}H_{27}N$ = 401.55) |
| Sub 1-97 | m/z = 619.23($C_{45}H_{33}NS$ = 619.83) | Sub 1-98 | m/z = 493.28($C_{37}H_{35}N$ = 493.69) |
| Sub 1-99 | m/z = 493.28($C_{37}H_{35}N$ = 493.69) | Sub 1-100 | m/z = 493.28($C_{37}H_{35}N$ = 493.69) |
| Sub 1-101 | m/z = 525.34($C_{39}H_{43}N$ = 525.78) | Sub 1-102 | m/z = 473.31($C_{35}H_{39}N$ = 473.70) |
| Sub 1-103 | m/z = 375.16($C_{27}H_{21}NO$ = 375.47) | Sub 1-104 | m/z = 513.25($C_{39}H_{31}N$ = 513.68) |
| Sub 1-105 | m/z = 513.25($C_{39}H_{31}N$ = 513.68) | Sub 1-106 | m/z = 451.19($C_{33}H_{25}NO$ = 451.57) |
| Sub 1-107 | m/z = 417.25($C_{31}H_{31}N$ = 417.60) | Sub 1-108 | m/z = 603.26($C_{45}H_{33}NO$ = 603.77) |
| Sub 1-109 | m/z = 603.26($C_{45}H_{33}NO$ = 603.77) | Sub 1-110 | m/z = 583.29($C_{43}H_{37}NO$ = 583.78) |
| Sub 1-111 | m/z = 513.25($C_{39}H_{31}N$ = 513.68) | Sub 1-112 | m/z = 708.50($C_{52}H_8D_{31}N$ = 709.08) |
| Sub 1-113 | m/z = 458.36($C_{33}H_{18}D_{15}N$ = 458.73) | Sub 1-114 | m/z = 470.35($C_{34}H_{10}D_{19}N$ = 470.73) |
| Sub 1-115 | m/z = 367.23($C_{27}H_{29}N$ = 367.54) | Sub 1-116 | m/z = 443.26($C_{33}H_{33}N$ = 443.63) |
| Sub 1-117 | m/z = 379.23($C_{28}H_{29}N$ = 379.55) | Sub 1-118 | m/z = 419.26($C_{31}H_{33}N$ = 419.61) |
| Sub 1-119 | m/z = 341.21($C_{25}H_{27}N$ = 341.5) | Sub 1-120 | m/z = 451.19($C_{33}H_{25}NO$ = 451.57) |
| Sub 1-121 | m/z = 451.19($C_{33}H_{25}NO$ = 451.57) | Sub 1-122 | m/z = 467.17($C_{33}H_{25}NS$ = 467.63) |
| Sub 1-123 | m/z = 391.14($C_{27}H_{21}NS$ = 391.53) | Sub 1-124 | m/z = 375.16($C_{27}H_{21}NO$ = 375.47) |
| Sub 1-125 | m/z = 499.19($C_{37}H_{25}NO$ = 499.61) | Sub 1-126 | m/z = 575.22($C_{43}H_{29}NO$ = 575.71) |
| Sub 1-127 | m/z = 513.16($C_{37}H_{23}NS$ = 513.66) | Sub 1-128 | m/z = 573.21($C_{43}H_{27}NO$ = 573.7) |
| Sub 1-129 | m/z = 527.22($C_{39}H_{29}NO$ = 527.67) | Sub 1-130 | m/z = 450.21($C_{33}H_{26}N_2$ = 450.59) |
| Sub 1-131 | m/z = 526.24($C_{39}H_{30}N_2$ = 526.68) | Sub 1-132 | m/z = 450.21($C_{33}H_{26}N_2$ = 450.59) |
| Sub1-133 | m/z = 451.19(C33H25NO = 451.57) | Sub1-134 | m/z = 451.19(C33H25NO = 451.57) |
| Sub1-135 | m/z = 381.2(C27H15D6NO = 381.51) | Sub1-136 | m/z = 388.24(C27H8D13NO = 388.55) |
| Sub1-137 | m/z = 382.21(C27H14D7NO = 382.51) | Sub1-138 | m/z = 451.19(C33H25NO = 451.57) |
| Sub1-139 | m/z = 456.22(C33H20D5NO = 456.6) | Sub1-140 | m/z = 451.19(C33H25NO = 451.57) |

II. Synthesis of Sub 2

Sub 2 of Reaction Scheme 1 is synthesized through the reaction route of Reaction Scheme 3, but is not limited thereto.

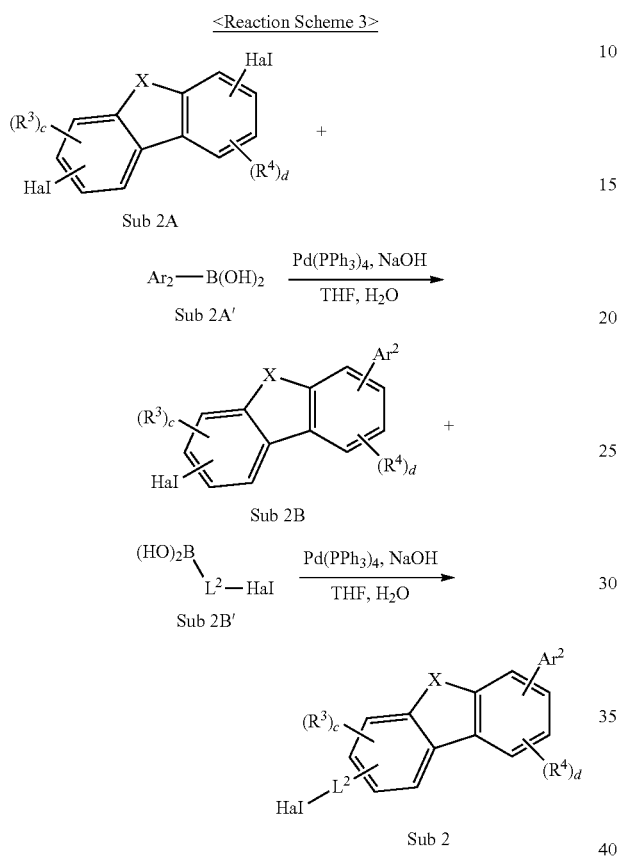

In Reaction Scheme 3, if $L^2$ of Sub 2 is absent, the step of reacting with $L^2$ can be omitted.

The compounds belonging to Sub 2 may be the following compounds, but are not limited to, and Table 2 shows the FD-MS (Field Desorption-Mass Spectrometry) values of the compounds belonging to Sub 2.

Sub 2-1

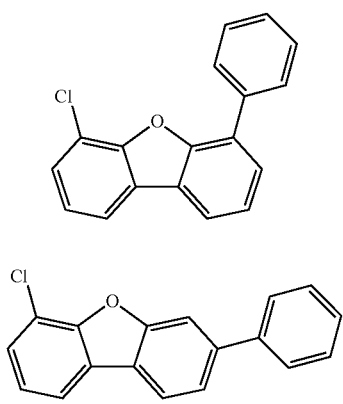

Sub 2-2

Sub 2-3

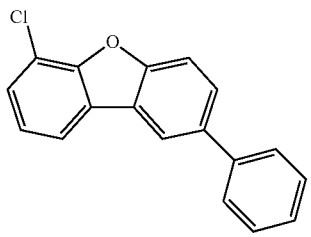

Sub 2-4

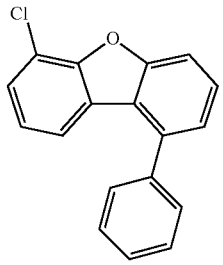

Sub 2-5

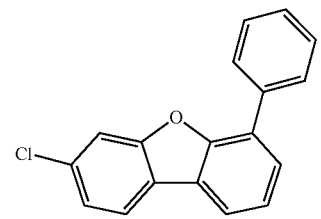

Sub 2-6

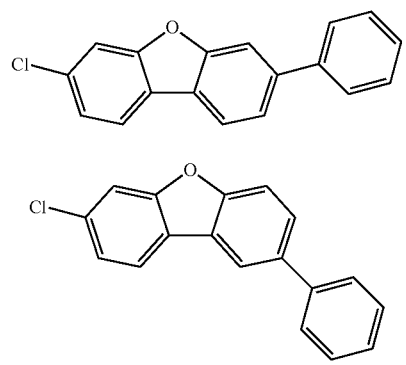

Sub 2-7

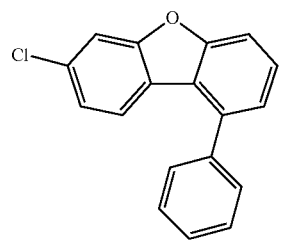

Sub 2-8

Sub 2-9

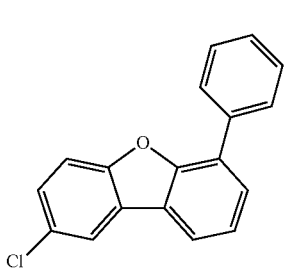

Sub 2-10
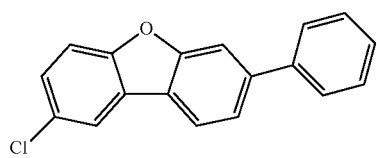
Sub 2-11
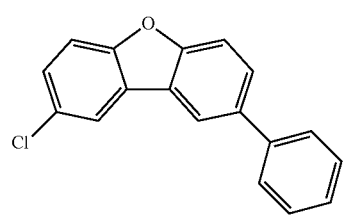
Sub 2-12
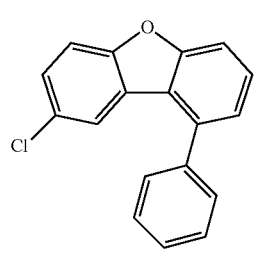
Sub 2-13
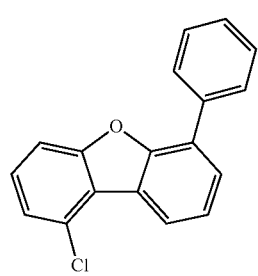
Sub 2-14
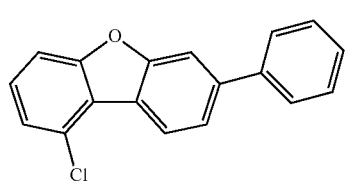
Sub 2-15
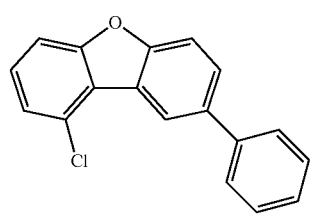
Sub 2-16
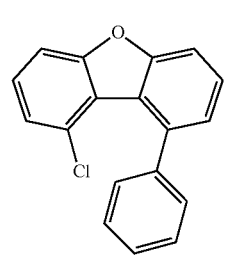
Sub 2-17
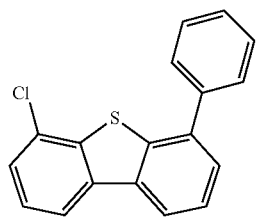
Sub 2-18
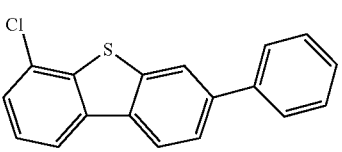
Sub 2-19
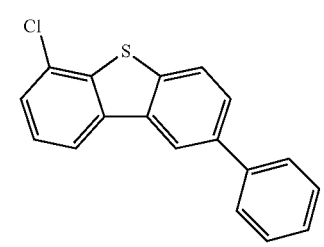
Sub 2-20
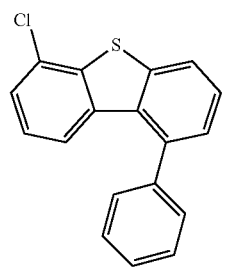
Sub 2-21
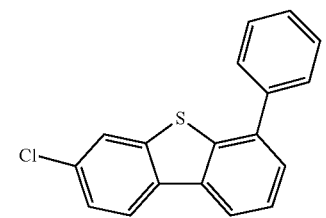
Sub 2-22
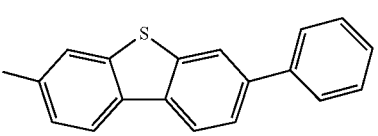
Sub 2-23
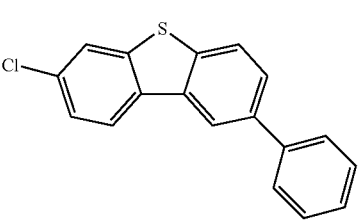

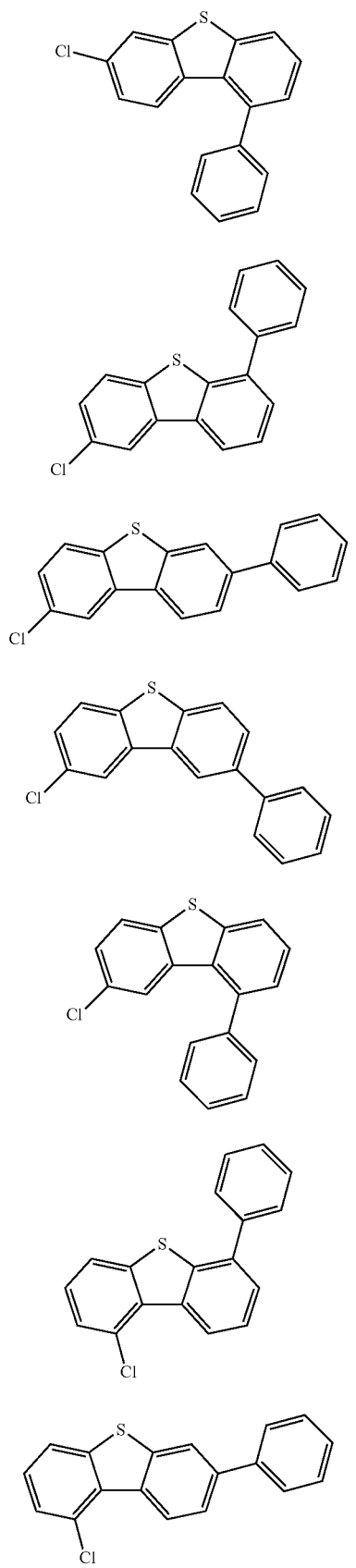
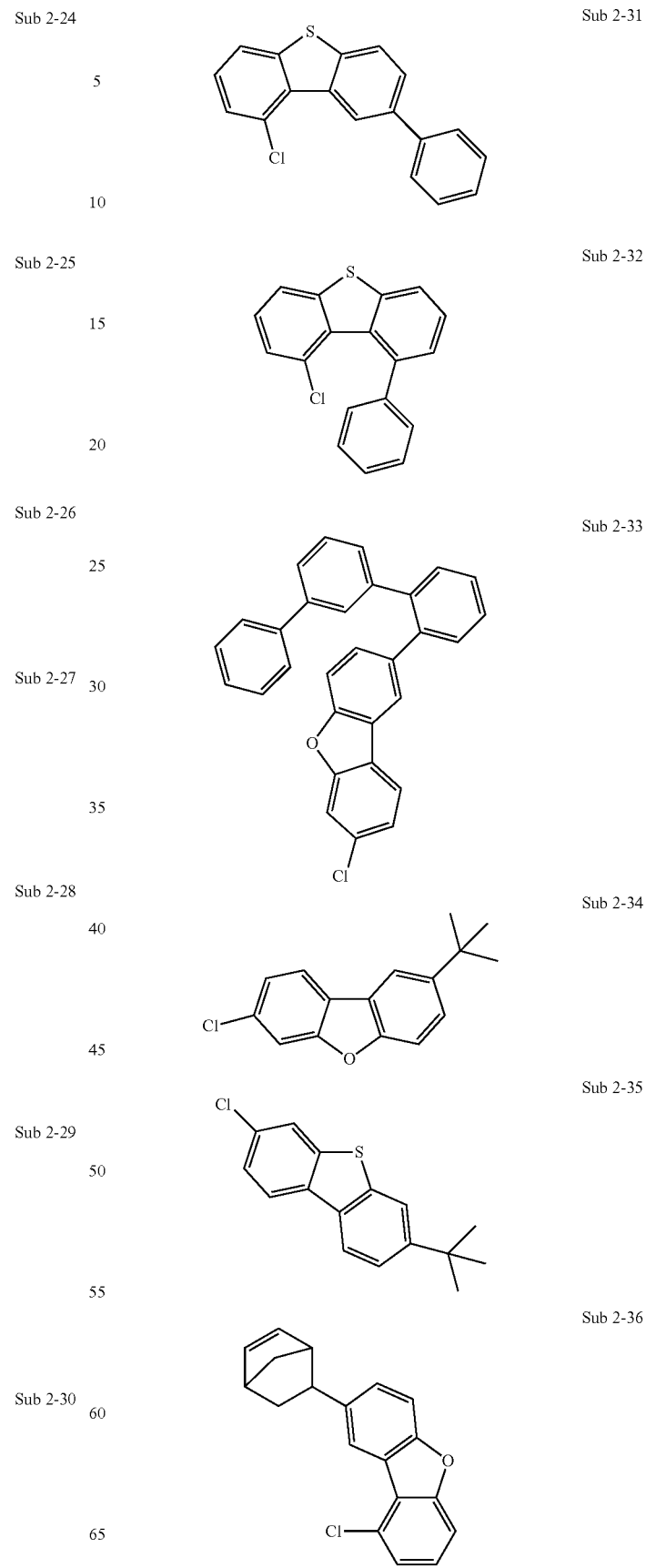
Sub 2-24
Sub 2-25
Sub 2-26
Sub 2-27
Sub 2-28
Sub 2-29
Sub 2-30
Sub 2-31
Sub 2-32
Sub 2-33
Sub 2-34
Sub 2-35
Sub 2-36

Sub 2-37
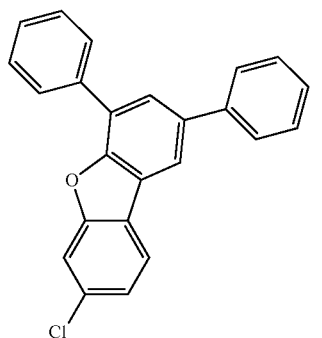
Sub 2-38
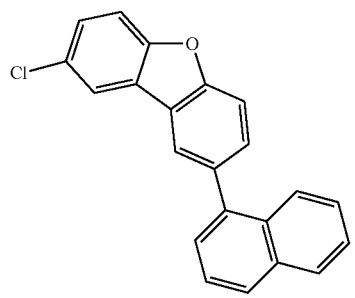
Sub 2-39
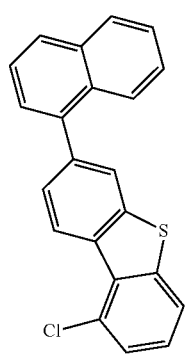
Sub 2-40
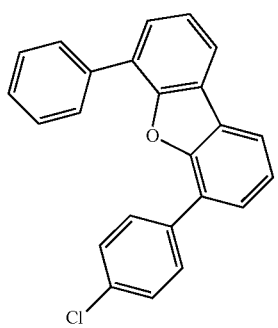
Sub 2-41
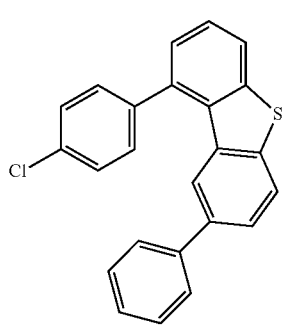
Sub 2-42
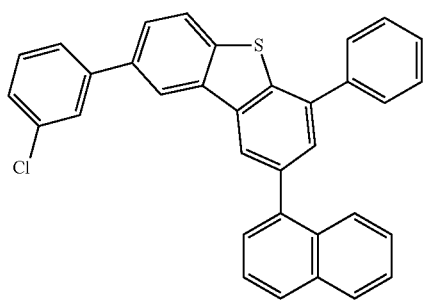
Sub 2-43
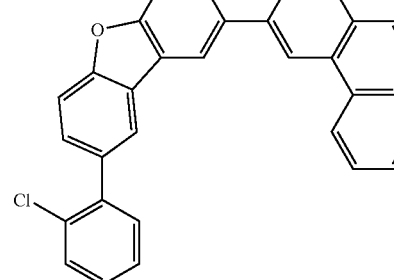
Sub 2-44
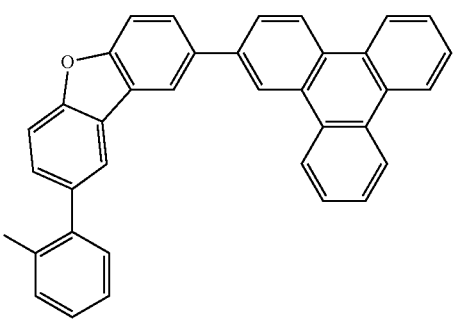
Sub 2-45
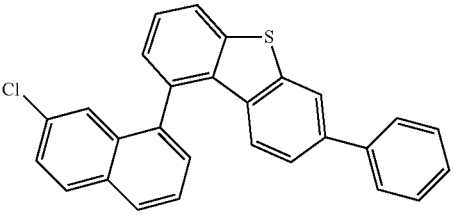
Sub 2-46
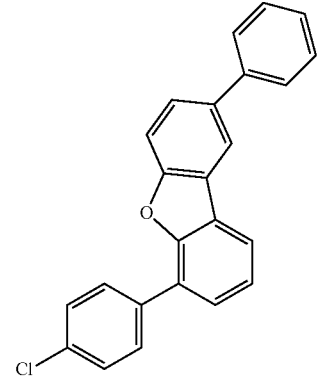

Sub 2-47
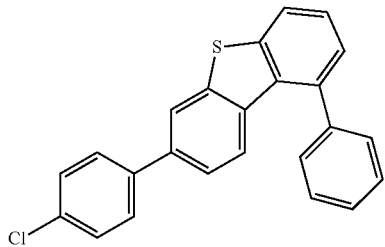
Sub 2-48
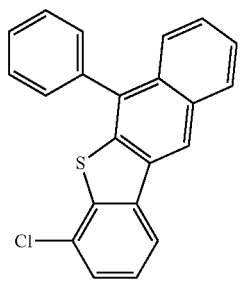
Sub 2-49
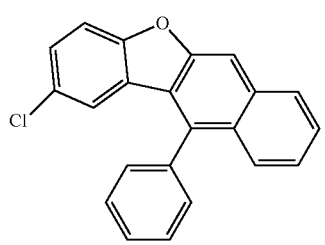
Sub 2-50
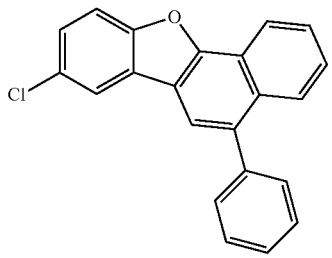
Sub 2-51
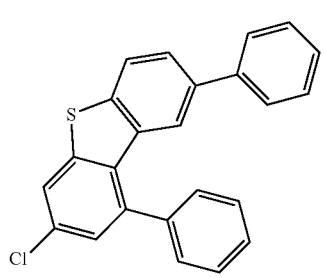
Sub 2-52
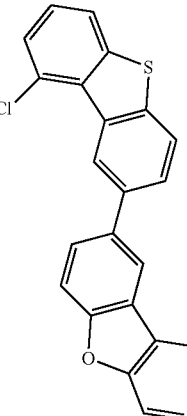
Sub 2-53
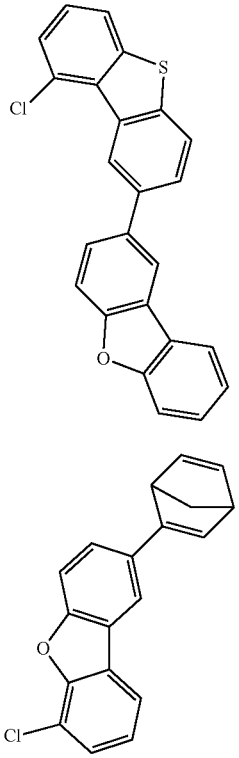
Sub 2-54
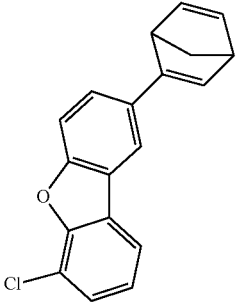
Sub 2-55
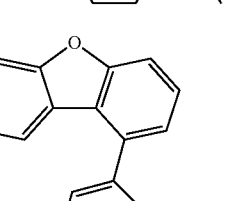
Sub 2-56
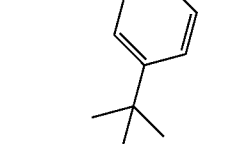

Sub 2-57
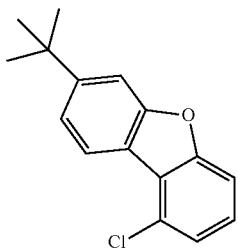
Sub 2-58
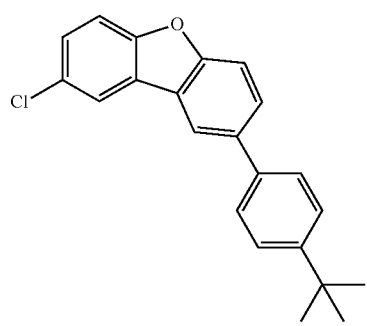
Sub 2-59
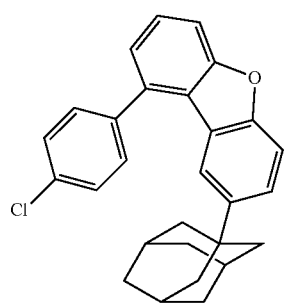
Sub 2-60
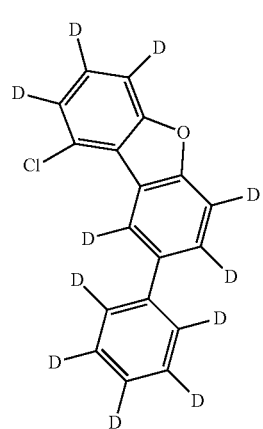
Sub 2-61
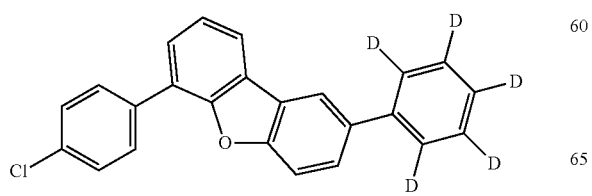
Sub 2-62
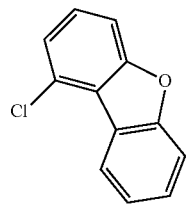
Sub 2-63
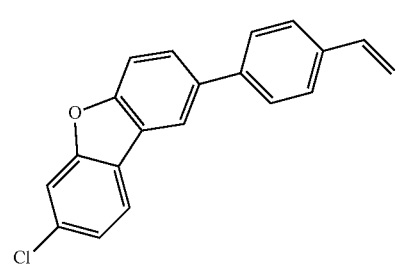
Sub 2-64
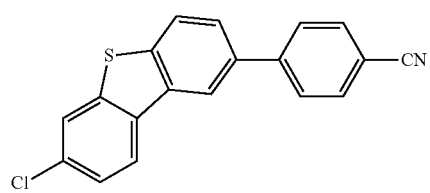
Sub 2-65
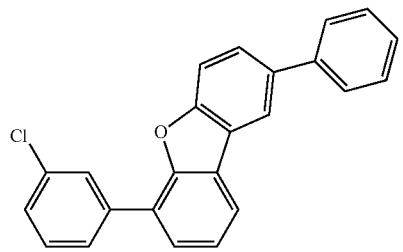
Sub 2-66
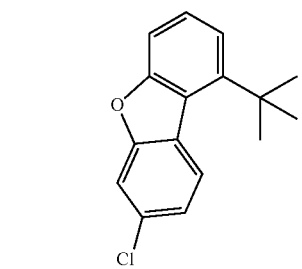
Sub 2-67
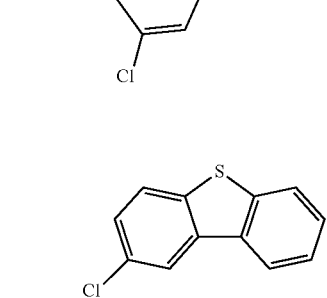

Sub 2-68
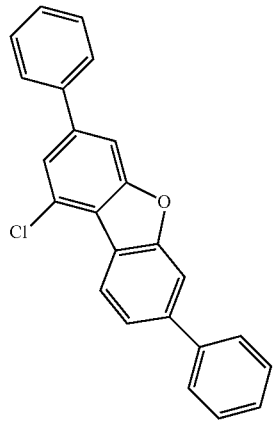
Sub 2-69
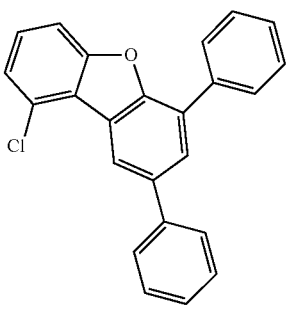
Sub 2-70
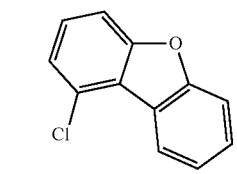
Sub 2-71
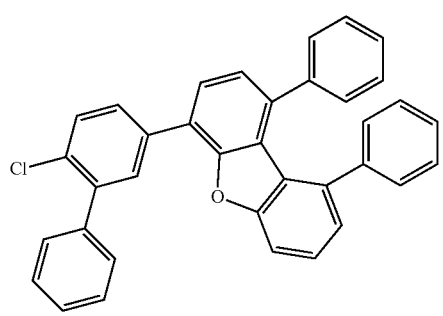
Sub 2-72
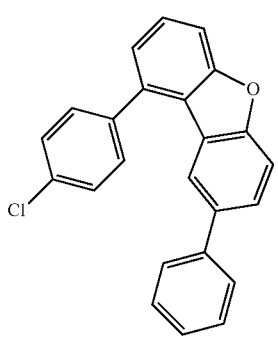
Sub 2-73
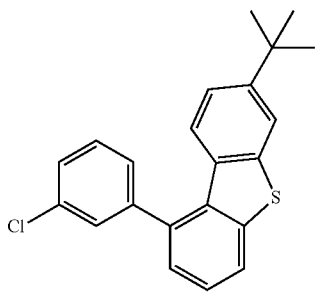
Sub 2-74
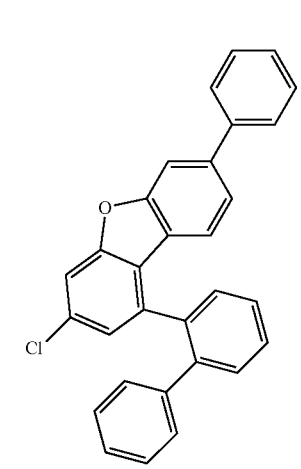
Sub 2-75
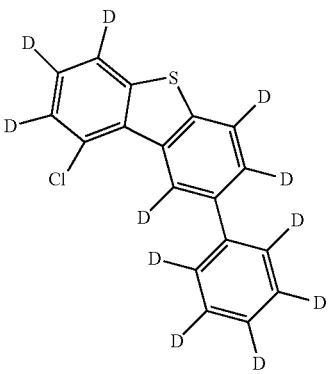
Sub 2-76
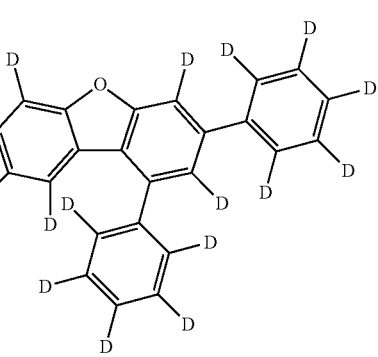

Sub 2-77
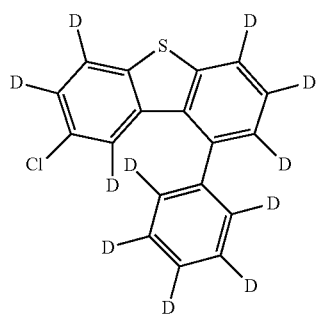
Sub 2-78
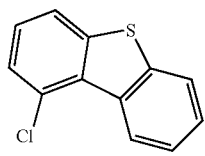
Sub 2-79
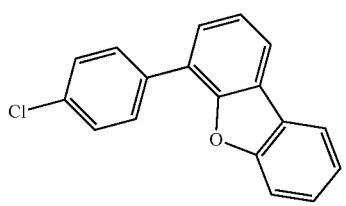
Sub 2-80
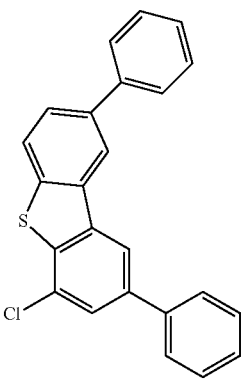
Sub 2-81
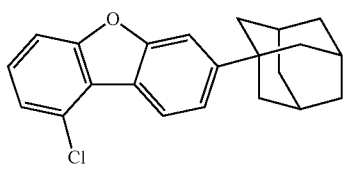
Sub 2-82
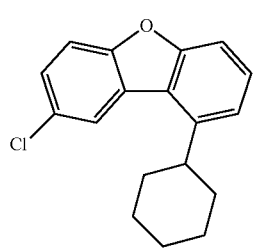
Sub 2-83
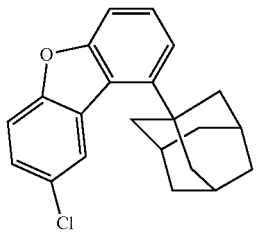
Sub 2-84
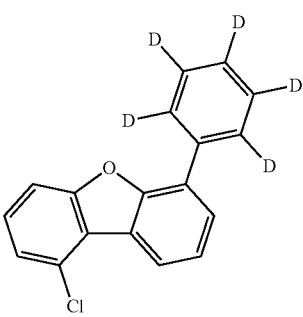
Sub 2-85
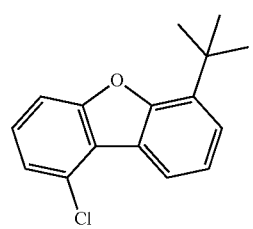
Sub 2-86
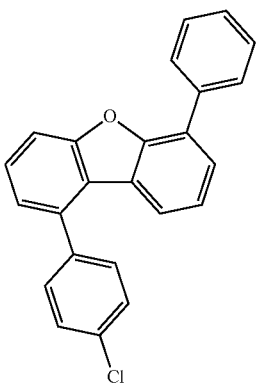
Sub 2-87
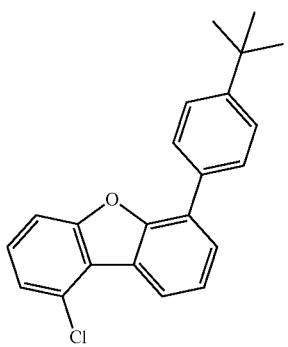

-continued

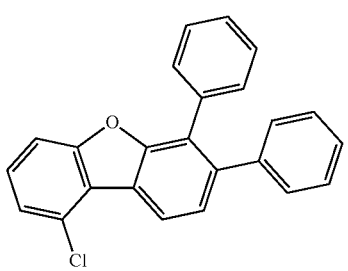

Sub 2-88

TABLE 2

| Compound | FD-MS | Compound | FD-MS |
|---|---|---|---|
| Sub 2-1 | m/z = 278.05($C_{18}H_{11}ClO$ = 278.74) | Sub 2-2 | m/z = 278.05($C_{18}H_{11}ClO$ = 278.74) |
| Sub 2-3 | m/z = 278.05($C_{18}H_{11}ClO$ = 278.74) | Sub 2-4 | m/z = 278.05($C_{18}H_{11}ClO$ = 278.74) |
| Sub 2-5 | m/z = 278.05($C_{18}H_{11}ClO$ = 278.74) | Sub 2-6 | m/z = 278.05($C_{18}H_{11}ClO$ = 278.74) |
| Sub 2-7 | m/z = 278.05($C_{18}H_{11}ClO$ = 278.74) | Sub 2-8 | m/z = 278.05($C_{18}H_{11}ClO$ = 278.74) |
| Sub 2-9 | m/z = 278.05($C_{18}H_{11}ClO$ = 278.74) | Sub 2-10 | m/z = 278.05($C_{18}H_{11}ClO$ = 278.74) |
| Sub 2-11 | m/z = 278.05($C_{18}H_{11}ClO$ = 278.74) | Sub 2-12 | m/z = 278.05($C_{18}H_{11}ClO$ = 278.74) |
| Sub 2-13 | m/z = 278.05($C_{18}H_{11}ClO$ = 278.74) | Sub 2-14 | m/z = 278.05($C_{18}H_{11}ClO$ = 278.74) |
| Sub 2-15 | m/z = 278.05($C_{18}H_{11}ClO$ = 278.74) | Sub 2-16 | m/z = 278.05($C_{18}H_{11}ClO$ = 278.74) |
| Sub 2-17 | m/z = 294.03($C_{18}H_{11}ClS$ = 294.80) | Sub 2-18 | m/z = 294.03($C_{18}H_{11}ClS$ = 294.80) |
| Sub 2-19 | m/z = 294.03($C_{18}H_{11}ClS$ = 294.80) | Sub 2-20 | m/z = 294.03($C_{18}H_{11}ClS$ = 294.80) |
| Sub 2-21 | m/z = 294.03($C_{18}H_{11}ClS$ = 294.80) | Sub 2-22 | m/z = 294.03($C_{18}H_{11}ClS$ = 294.80) |
| Sub 2-23 | m/z = 294.03($C_{18}H_{11}ClS$ = 294.80) | Sub 2-24 | m/z = 294.03($C_{18}H_{11}ClS$ = 294.80) |
| Sub 2-25 | m/z = 294.03($C_{18}H_{11}ClS$ = 294.80) | Sub 2-26 | m/z = 294.03($C_{18}H_{11}ClS$ = 294.80) |
| Sub 2-27 | m/z = 294.03($C_{18}H_{11}ClS$ = 294.80) | Sub 2-28 | m/z = 294.03($C_{18}H_{11}ClS$ = 294.80) |
| Sub 2-29 | m/z = 294.03($C_{18}H_{11}ClS$ = 294.80) | Sub 2-30 | m/z = 294.03($C_{18}H_{11}ClS$ = 294.80) |
| Sub 2-31 | m/z = 294.03($C_{18}H_{11}ClS$ = 294.80) | Sub 2-32 | m/z = 294.03($C_{18}H_{11}ClS$ = 294.80) |
| Sub 2-33 | m/z = 430.11($C_{30}H_{19}ClO$ = 430.93) | Sub 2-34 | m/z = 258.08($C_{16}H_{15}ClO$ = 258.75) |
| Sub 2-35 | m/z = 274.06($C_{16}H_{15}ClS$ = 274.81) | Sub 2-36 | m/z = 294.08($C_{19}H_{15}ClO$ = 294.78) |
| Sub 2-37 | m/z = 354.08($C_{24}H_{15}ClO$ = 354.83) | Sub 2-38 | m/z = 328.07($C_{22}H_{13}ClO$ = 328.80) |
| Sub 2-39 | m/z = 344.04($C_{22}H_{13}ClS$ = 344.86) | Sub 2-40 | m/z = 354.08($C_{24}H_{15}ClO$ = 354.83) |
| Sub 2-41 | m/z = 370.06($C_{24}H_{15}ClS$ = 370.89) | Sub 2-42 | m/z = 496.11($C_{34}H_{21}ClS$ = 497.05) |
| Sub 2-43 | m/z = 504.13($C_{36}H_{21}ClO$ = 505.01) | Sub 2-44 | m/z = 420.07($C_{28}H_{17}ClS$ = 420.95) |
| Sub 2-45 | m/z = 350.09($C_{22}H_{19}ClS$ = 350.90) | Sub 2-46 | m/z = 354.08($C_{24}H_{15}ClO$ = 354.83) |
| Sub 2-47 | m/z = 370.06($C_{24}H_{15}ClS$ = 370.89) | Sub 2-48 | m/z = 344.04($C_{22}H_{13}ClS$ = 344.86) |
| Sub 2-49 | m/z = 328.07($C_{22}H_{13}ClO$ = 328.80) | Sub 2-50 | m/z = 328.07($C_{22}H_{13}ClO$ = 328.80) |
| Sub 2-51 | m/z = 370.06($C_{24}H_{15}ClS$ = 370.89) | Sub 2-52 | m/z = 384.04($C_{24}H_{13}ClOS$ = 384.88) |
| Sub 2-53 | m/z = 292.07($C_{19}H_{13}ClO$ = 292.76) | Sub 2-54 | m/z = 258.08($C_{16}H_{15}ClO$ = 258.75) |
| Sub 2-55 | m/z = 460.07($C_{30}H_{17}ClOS$ = 460.98) | Sub 2-56 | m/z = 334.11($C_{22}H_{19}ClO$ = 334.84) |
| Sub 2-57 | m/z = 258.08($C_{16}H_{15}ClO$ = 258.75) | Sub 2-58 | m/z = 334.11($C_{22}H_{19}ClO$ = 334.84) |
| Sub 2-59 | m/z = 412.16($C_{28}H_{25}ClO$ = 412.96) | Sub 2-60 | m/z = 289.12($C_{18}D_{11}ClO$ = 289.80) |
| Sub 2-61 | m/z = 359.11($C_{24}H_{10}D_5ClO$ = 359.86) | Sub 2-62 | m/z = 202.02($C_{12}H_7ClO$ = 202.64) |
| Sub 2-63 | m/z = 304.07($C_{20}H_{13}ClO$ = 304.77) | Sub 2-64 | m/z = 319.02($C_{19}H_{10}ClNS$ = 319.81) |
| Sub 2-65 | m/z = 354.08($C_{24}H_{15}ClO$ = 354.83) | Sub 2-66 | m/z = 258.08($C_{16}H_{15}ClO$ = 258.75) |
| Sub 2-67 | m/z = 218.00($C_{12}H_7ClS$ = 218.70) | Sub 2-68 | m/z = 354.08($C_{24}H_{15}ClO$ = 354.83) |
| Sub 2-69 | m/z = 354.08($C_{24}H_{15}ClO$ = 354.83) | Sub 2-70 | m/z = 202.02($C_{12}H_7ClO$ = 202.64) |
| Sub 2-71 | m/z = 506.14($C_{36}H_{23}ClO$ = 507.03) | Sub 2-72 | m/z = 354.08($C_{24}H_{15}ClO$ = 354.83) |
| Sub 2-73 | m/z = 350.09($C_{22}H_{19}ClS$ = 350.9) | Sub 2-74 | m/z = 430.11($C_{30}H_{19}ClO$ = 430.93) |
| Sub 2-75 | m/z = 305.10($C_{18}D_{11}ClS$ = 305.86) | Sub 2-76 | m/z = 369.18($C_{24}D_{15}ClO$ = 369.92) |
| Sub 2-77 | m/z = 305.10($C_{18}D_{11}ClS$ = 305.86) | Sub 2-78 | m/z = 218.00($C_{12}H_7ClS$ = 218.70) |
| Sub 2-79 | m/z = 278.05($C_{18}H_{11}ClO$ = 278.74) | Sub 2-80 | m/z = 370.06($C_{24}H_{15}ClS$ = 370.89) |
| Sub 2-81 | m/z = 336.13($C_{22}H_{21}ClO$ = 336.86) | Sub 2-82 | m/z = 284.10($C_{18}H_{17}ClO$ = 284.78) |
| Sub 2-83 | m/z = 336.13($C_{22}H_{21}ClO$ = 336.86) | Sub 2-84 | m/z = 283.08($C18H6D5ClO$ = 283.77) |
| Sub 2-85 | m/z = 258.08($C16H15ClO$ = 258.75) | Sub 2-86 | m/z = 354.08($C24H15ClO$ = 354.83) |
| Sub 2-87 | m/z = 334.11($C22H19ClO$ = 334.84) | Sub 2-88 | m/z = 354.08($C24H15ClO$ = 354.83) |

III. Synthesis of Final Product

1. Synthesis Example of P-11

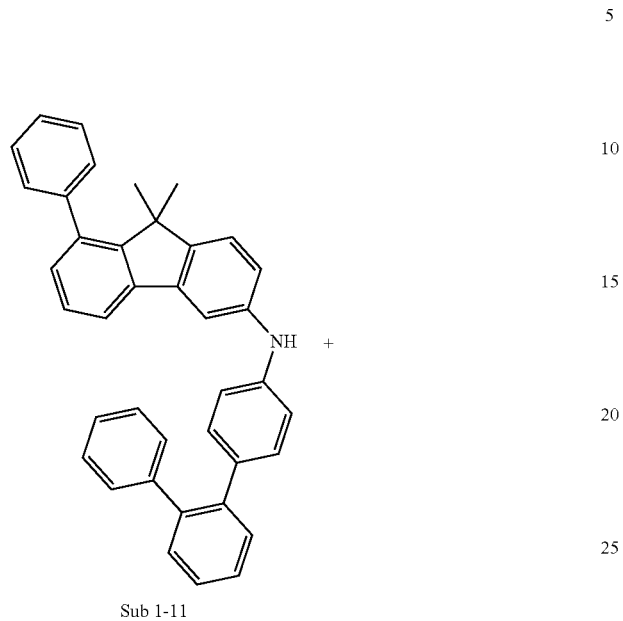

Sub 1-11

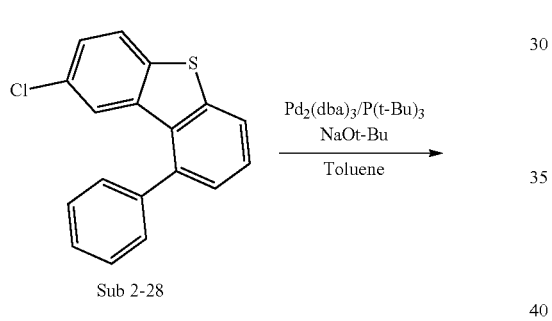

Sub 2-28

P-11

2. Synthesis Example of P-40

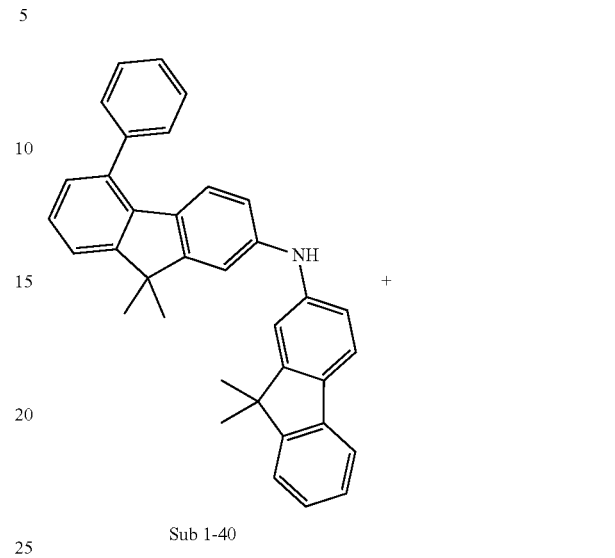

Sub 1-40

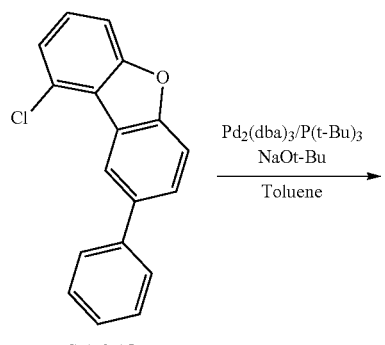

Sub 2-15

P-40

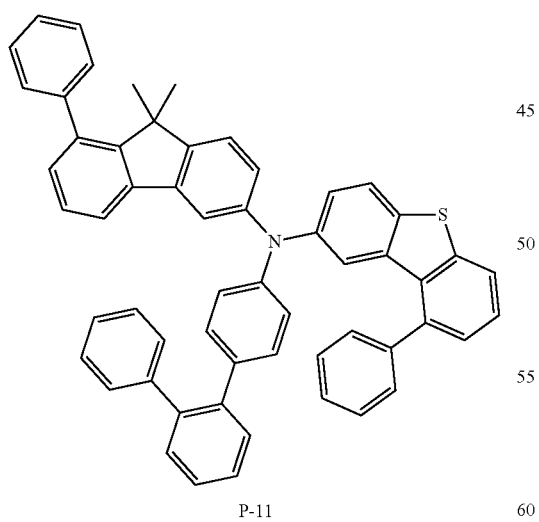

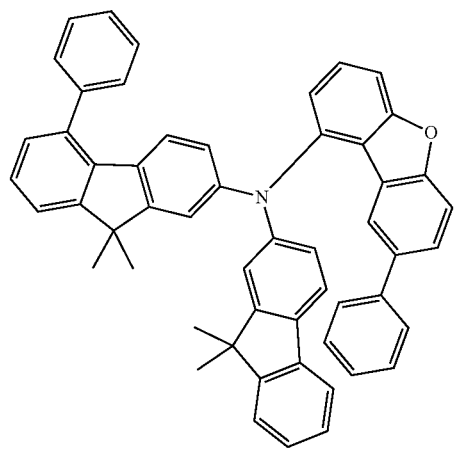

Sub 1-11 (20.0 g, 38.9 mmol) and Sub 2-28 (11.1 g, 38.9 mmol), Pd$_2$(dba)$_3$ (1.1 g, 1.2 mmol), P(t-Bu)$_3$ (0.5 g, 2.3 mmol), NaOt-Bu (7.5 g, 77.9 mmol), toluene (195 mL) were added to a round bottom flask in the same manner as Sub 1-11 to obtain 21.5 g of product. (Yield: 71.4%).

Sub 1-40 (20.0 g, 41.9 mmol) and Sub 2-15 (11.3 g, 41.9 mmol), Pd$_2$(dba)$_3$ (1.2 g, 1.3 mmol), P(t-Bu)$_3$ (0.5 g, 2.5 mmol), NaOt-Bu (8.0 g, 83.7 mmol), toluene (209 mL) were added to a round bottom flask in the same manner as Sub 1-11 to obtain 21.9 g of product. (Yield: 72.5%).

3. Synthesis Example of P-49

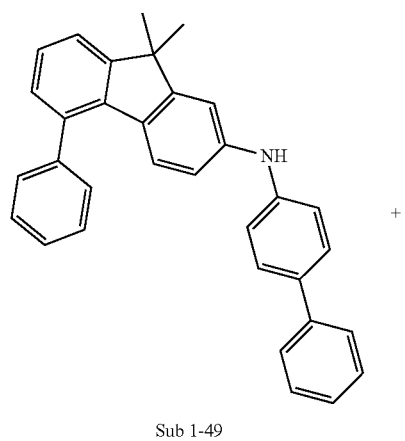

Sub 1-49

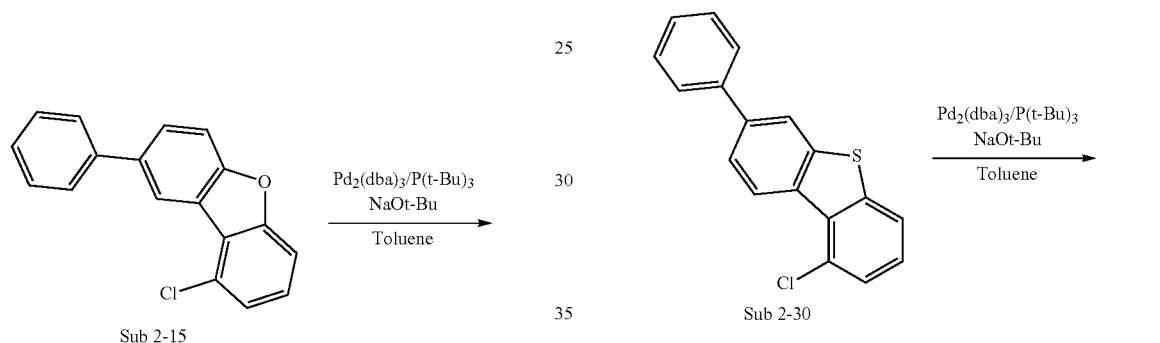

P-49

Sub 1-49 (20.0 g, 45.7 mmol) and Sub 2-15 (12.3 g, 45.7 mmol), Pd$_2$(dba)$_3$ (1.3 g, 1.4 mmol), P(t-Bu)$_3$ (0.6 g, 2.7 mmol), NaOt-Bu (8.8 g, 91.4 mmol), toluene (229 mL) were added to a round bottom flask in the same manner as Sub 1-11 to obtain 22.5 g of product. (Yield: 72.3%).

4. Synthesis Example of P-57

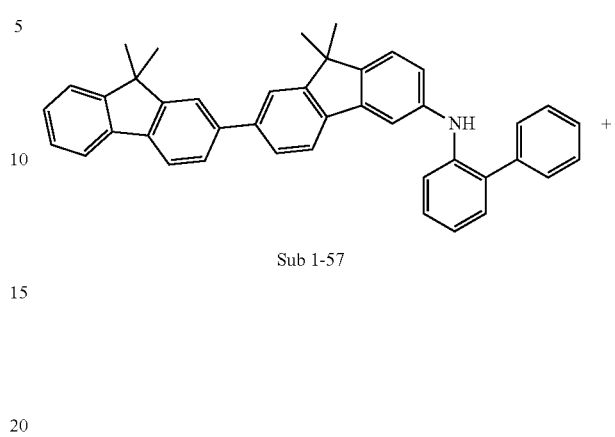

Sub 1-57

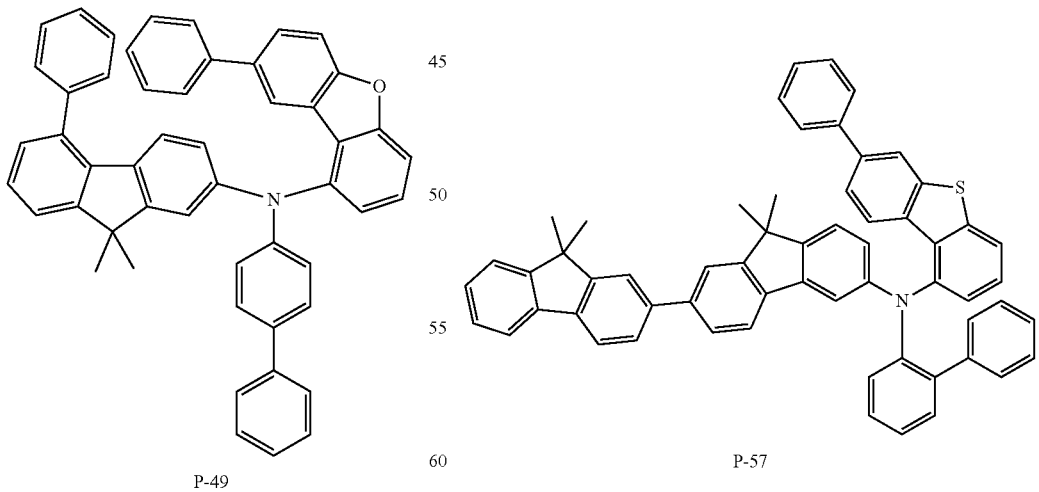

P-57

Sub 1-57 (20.0 g, 36.1 mmol) and Sub 2-30 (10.3 g, 36.1 mmol), Pd$_2$(dba)$_3$ (1.0 g, 1.1 mmol), P(t-Bu)$_3$ (0.4 g, 2.2 mmol), NaOt-Bu (6.9 g, 72.2 mmol), toluene (181 mL) were added to a round bottom flask in the same manner as Sub 1-11 to obtain 20.8 g of product. (Yield: 70.8%).

5. Synthesis Example of P-69

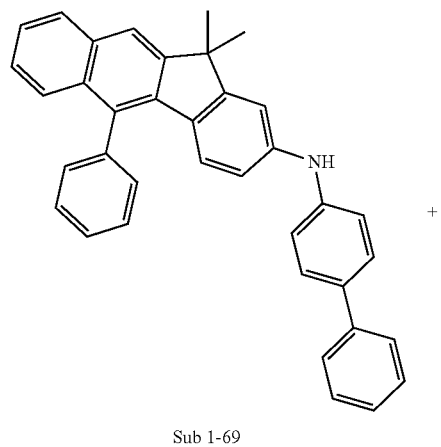
Sub 1-69

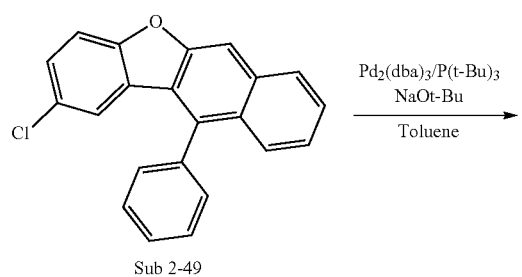
Sub 2-49

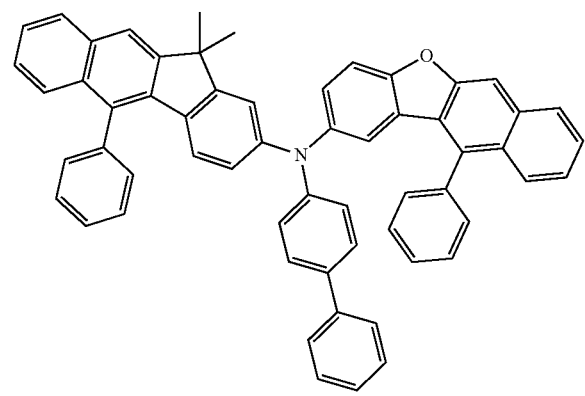
P-69

Sub 1-69 (20.0 g, 41.0 mmol) and Sub 2-49 (13.0 g, 41.0 mmol), Pd$_2$(dba)$_3$ (1.1 g, 1.2 mmol), P(t-Bu)$_3$ (0.5 g, 2.5 mmol), NaOt-Bu (7.9 g, 82.0 mmol), toluene (205 mL) were added to a round bottom flask in the same manner as Sub 1-11 to obtain 22.7 g of product. (Yield: 71.0%).

6. Synthesis Example of P-74

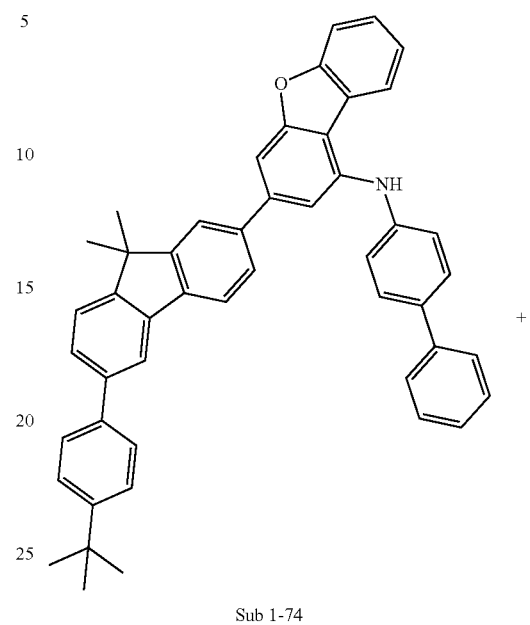
Sub 1-74

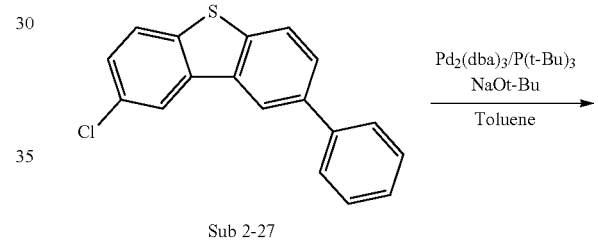
Sub 2-27

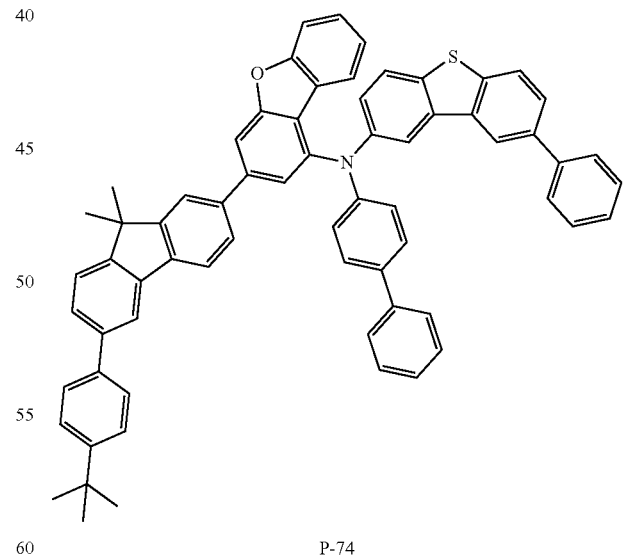
P-74

Sub 1-74 (20.0 g, 30.3 mmol) and Sub 2-27 (8.6 g, 30.3 mmol), Pd$_2$(dba)$_3$ (0.8 g, 0.9 mmol), P(t-Bu)$_3$ (0.4 g, 1.8 mmol), NaOt-Bu (5.8 g, 60.6 mmol), toluene (152 mL) were added to a round bottom flask in the same manner as Sub 1-11 to obtain 19.7 g of product. (Yield: 70.7%).

7. Synthesis Example of P-80

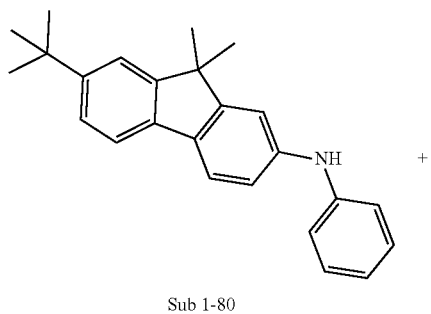

8. Synthesis Example of P-86

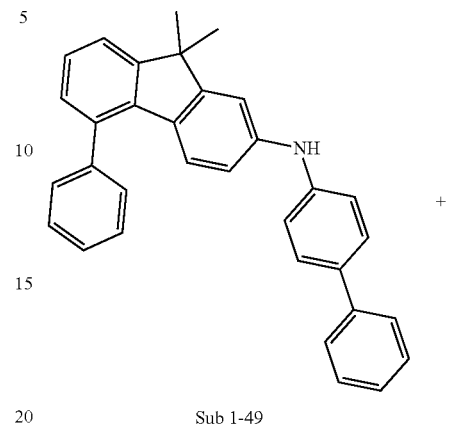

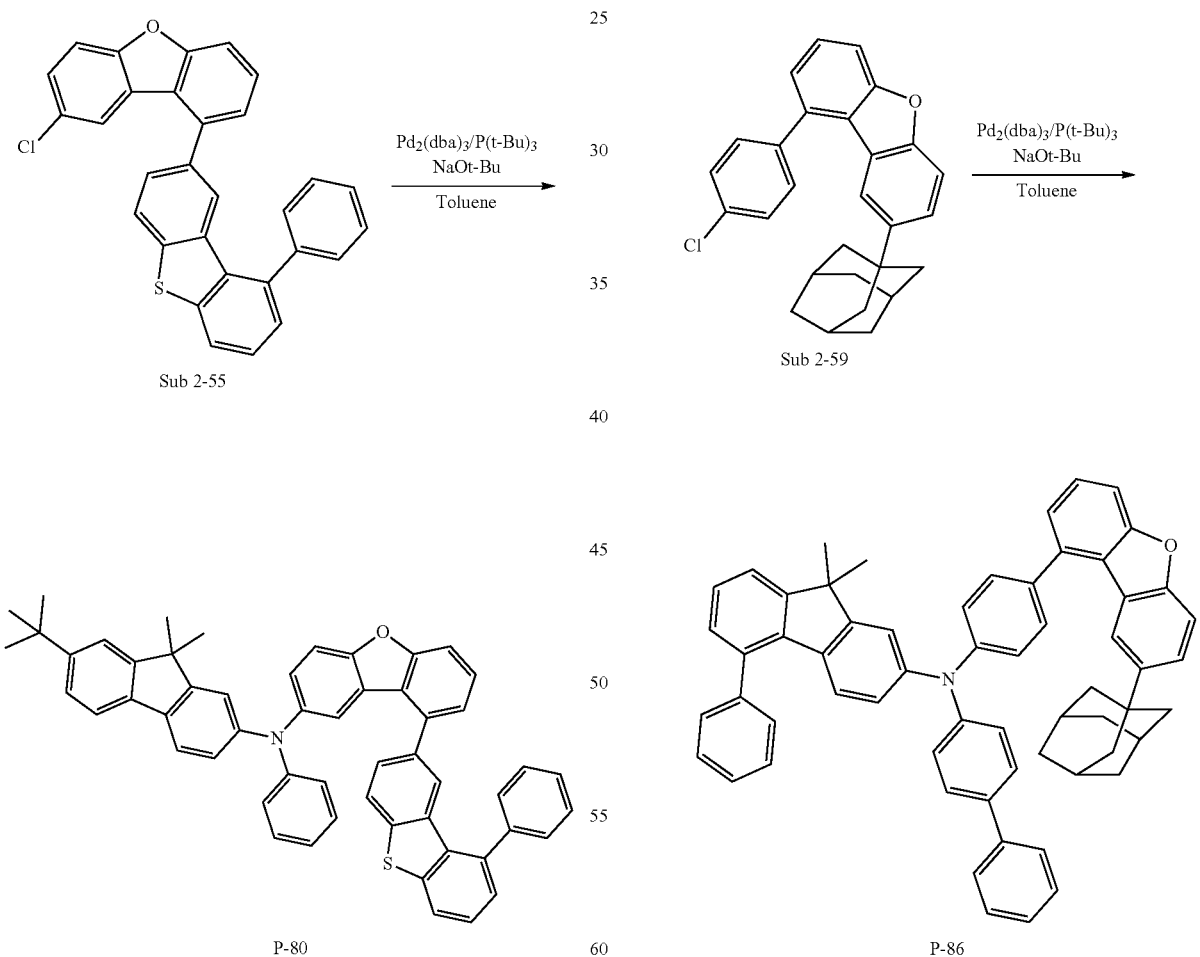

Sub 1-80 (20.0 g, 58.6 mmol) and Sub 2-55 (26.1 g, 58.6 mmol), Pd$_2$(dba)$_3$ (1.6 g, 1.8 mmol), P(t-Bu)$_3$ (0.7 g, 3.5 mmol), NaOt-Bu (11.3 g, 117.1 mmol), toluene (293 mL) were added to a round bottom flask in the same manner as Sub 1-11 to obtain 32.4 g of product. (Yield: 72.2%).

Sub 1-49 (20.0 g, 45.7 mmol) and Sub 2-59 (18.2 g, 45.7 mmol), Pd$_2$(dba)$_3$ (1.3 g, 1.4 mmol), P(t-Bu)$_3$ (0.6 g, 2.7 mmol), NaOt-Bu (8.8 g, 91.4 mmol), toluene (229 mL) were added to a round bottom flask in the same manner as Sub 1-11 to obtain 26.6 g of product. (Yield: 71.4%).

9. Synthesis Example of P-95

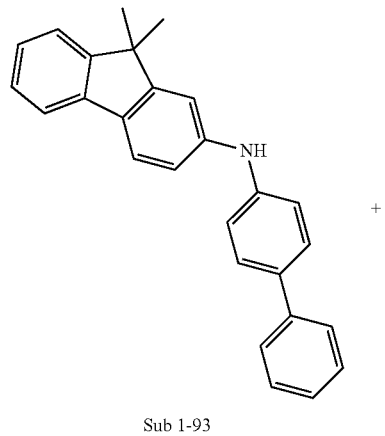

10. Synthesis Example of P-98

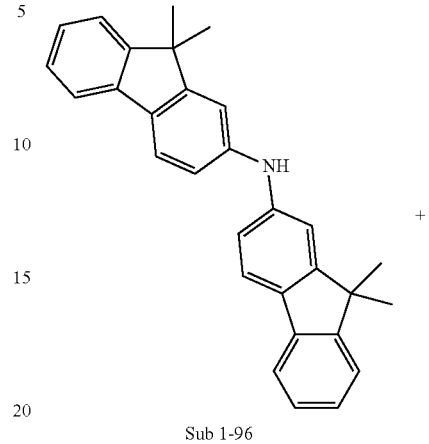

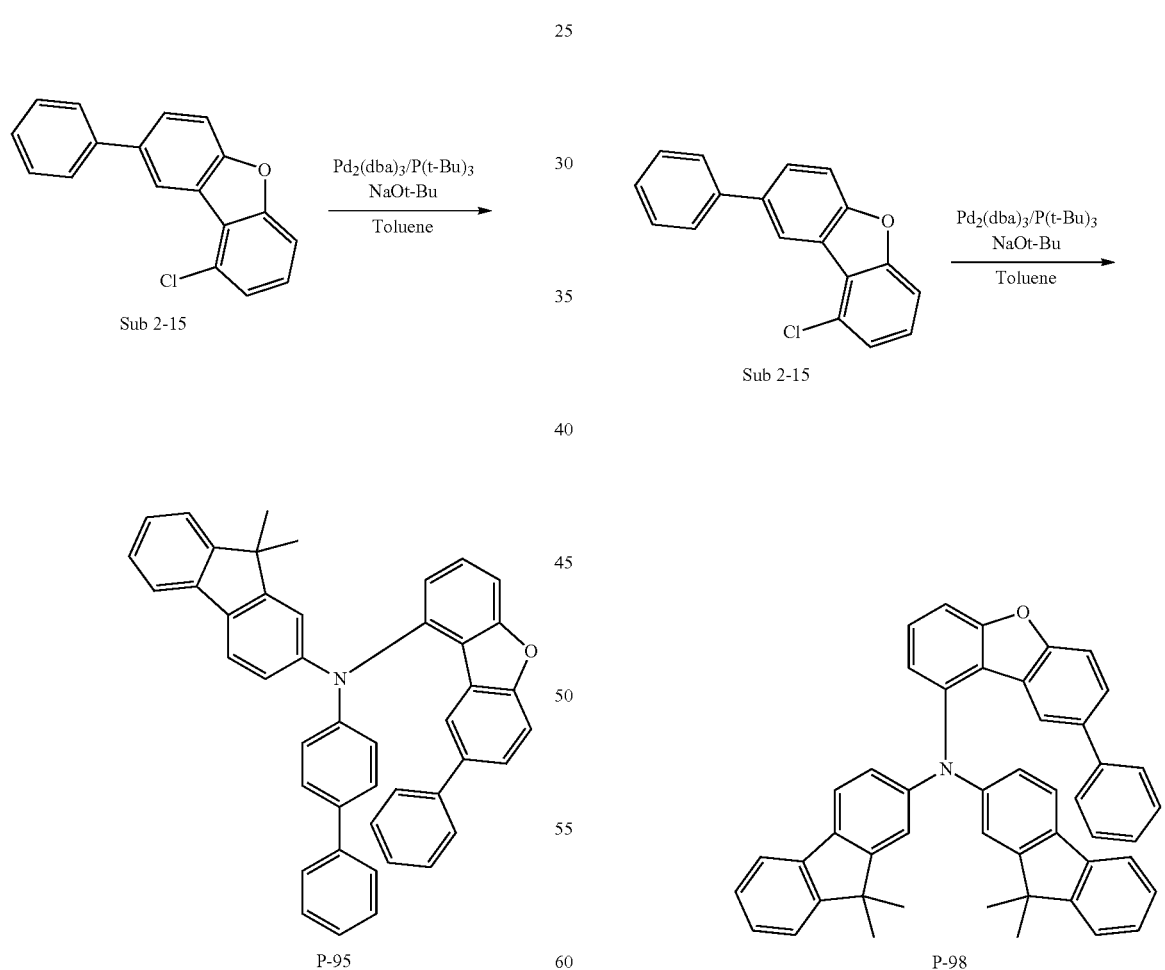

Sub 1-93 (20.0 g, 55.3 mmol) and Sub 2-15 (14.9 g, 55.3 mmol), Pd$_2$(dba)$_3$ (1.5 g, 1.7 mmol), P(t-Bu)$_3$ (0.7 g, 3.3 mmol), NaOt-Bu (10.6 g, 110.7 mmol), toluene (277 mL) were added to a round bottom flask in the same manner as Sub 1-11 to obtain 23.9 g of product. (Yield: 71.4%).

Sub 1-96 (20.0 g, 49.8 mmol) and Sub 2-15 (13.4 g, 49.8 mmol), Pd$_2$(dba)$_3$ (1.4 g, 1.5 mmol), P(t-Bu)$_3$ (0.6 g, 3.0 mmol), NaOt-Bu (9.6 g, 99.6 mmol), toluene (249 mL) were added to a round bottom flask in the same manner as Sub 1-11 to obtain 22.7 g of product. (Yield: 70.8%).

11. Synthesis Example of P-97

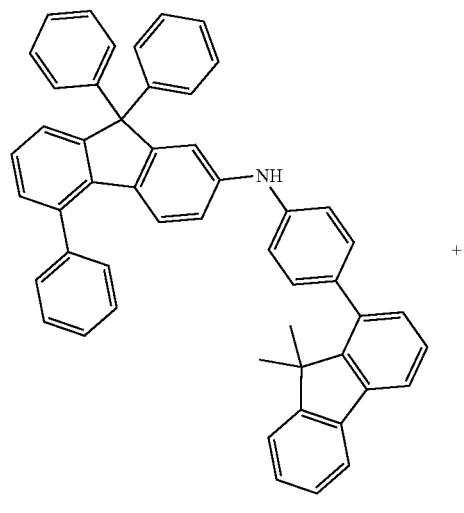

Sub 1-95

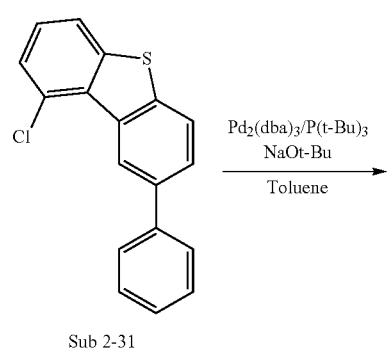

Sub 2-31

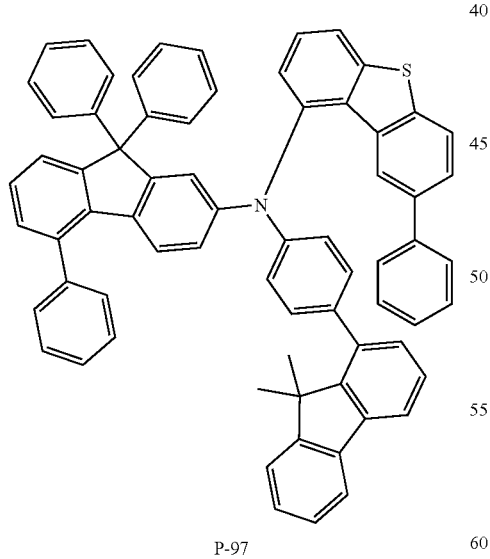

P-97

Sub 1-95 (20.0 g, 29.5 mmol) and Sub 2-31 (8.4 g, 29.5 mmol), Pd$_2$(dba)$_3$ (0.8 g, 0.9 mmol), P(t-Bu)$_3$ (0.4 g, 1.8 mmol), NaOt-Bu (5.7 g, 59.0 mmol), toluene (148 mL) were added to a round bottom flask in the same manner as Sub 1-11 to obtain 19.6 g of product. (Yield: 70.9%).

12. Synthesis Example of P-100

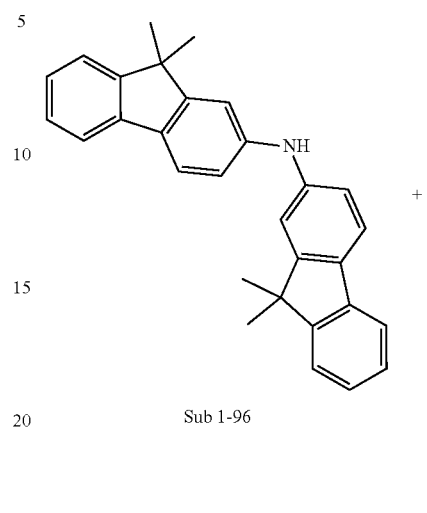

Sub 1-96

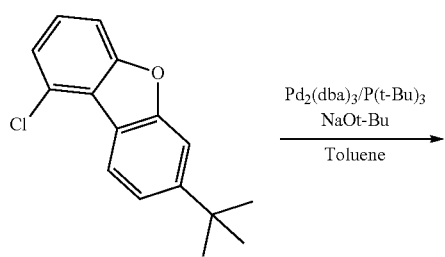

Sub 2-81

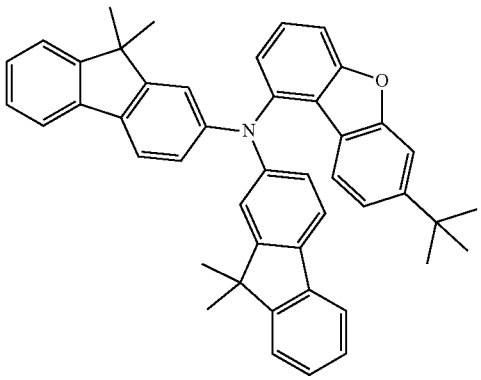

P-100

Sub 1-96 (20.0 g, 49.8 mmol) and Sub 2-81 (12.5 g, 49.8 mmol), Pd$_2$(dba)$_3$ (1.4 g, 1.5 mmol), P(t-Bu)$_3$ (0.6 g, 3.0 mmol), NaOt-Bu (9.6 g, 99.6 mmol), toluene (249 mL) were added to a round bottom flask in the same manner as Sub 1-11 to obtain 22.5 g of product. (Yield: 72.3%).

13. Synthesis Example of P-161

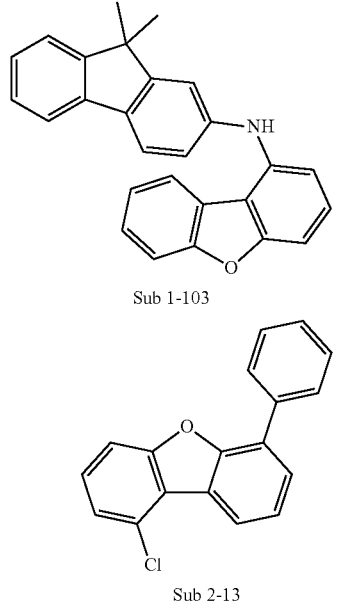

Sub 1-103

Sub 2-13

Pd$_2$(dba)$_3$/P(t-Bu)$_3$
NaOt-Bu
Toluene

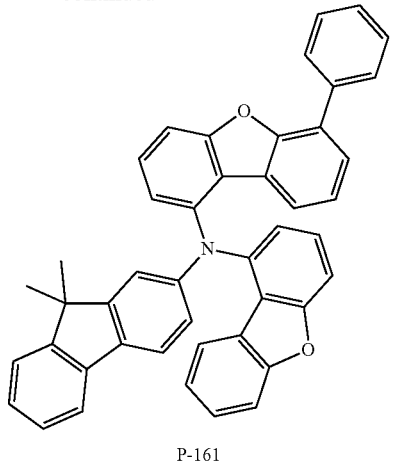

P-161

Sub 1-103 (20.0 g, 53.3 mmol) and Sub 2-13 (14.3 g, 53.3 mmol), Pd$_2$(dba)$_3$ (1.5 g, 1.6 mmol), P(t-Bu)$_3$ (0.7 g, 3.2 mmol), NaOt-Bu (10.2 g, 106.5 mmol), toluene (266 mL) were added to a round bottom flask in the same manner as Sub 1-11 to obtain 24.1 g of product. (Yield: 73.2%)

Meanwhile, the FD-MS values of compounds P-1 to P-137 of the present invention prepared according to the above synthesis examples are shown in Table 3.

TABLE 3

| Compound | FD-MS | Compound | FD-MS |
|---|---|---|---|
| P-1 | m/z = 603.26($C_{45}H_{33}NO$ = 603.77) | P-2 | m/z = 695.26($C_{51}H_{37}NS$ = 695.92) |
| P-3 | m/z = 679.29($C_{51}H_{37}NO$ = 679.86) | P-4 | m/z = 695.26($C_{51}H_{37}NS$ = 695.92) |
| P-5 | m/z = 771.30($C_{57}H_{41}NS$ = 772.02) | P-6 | m/z = 805.33($C_{61}H_{43}NO$ = 806.02) |
| P-7 | m/z = 745.28($C_{55}H_{39}NS$ = 745.98) | P-8 | m/z = 679.29($C_{51}H_{37}NO$ = 679.86) |
| P-9 | m/z = 755.32($C_{57}H_{41}NO$ = 755.96) | P-10 | m/z = 755.32($C_{57}H_{41}NO$ = 755.96) |
| P-11 | m/z = 771.30($C_{57}H_{41}NS$ = 772.02) | P-12 | m/z = 771.30($C_{57}H_{41}NS$ = 772.02) |
| P-13 | m/z = 719.26($C_{53}H_{37}NS$ = 719.95) | P-14 | m/z = 603.26($C_{45}H_{33}NO$ = 603.77) |
| P-15 | m/z = 669.25($C_{49}H_{35}NS$ = 669.89) | P-16 | m/z = 603.26($C_{45}H_{33}NO$ = 603.77) |
| P-17 | m/z = 829.33($C_{63}H_{43}NO$ = 830.04) | P-18 | m/z = 745.28($C_{55}H_{39}NS$ = 745.98) |
| P-19 | m/z = 923.36($C_{69}H_{49}NS$ = 924.22) | P-20 | m/z = 755.32($C_{57}H_{41}NO$ = 755.96) |
| P-21 | m/z = 785.31($C_{58}H_{43}NS$ = 786.05) | P-22 | m/z = 921.40($C_{70}H_{51}NO$ = 922.18) |
| P-23 | m/z = 719.26($C_{53}H_{37}NS$ = 719.95) | P-24 | m/z = 871.38($C_{66}H_{49}NO$ = 872.12) |
| P-25 | m/z = 719.32($C_{54}H_{41}NO$ = 719.93) | P-26 | m/z = 823.38($C_{62}H_{49}NO$ = 824.08) |
| P-27 | m/z = 821.37($C_{62}H_{47}NO$ = 822.06) | P-28 | m/z = 795.30($C_{59}H_{41}NS$ = 796.04) |
| P-29 | m/z = 857.31($C_{64}H_{43}NS$ = 858.12) | P-30 | m/z = 853.34($C_{62}H_{47}NOS$ = 854.12) |
| P-31 | m/z = 889.28($C_{64}H_{43}NS_2$ = 890.18) | P-32 | m/z = 859.33($C_{64}H_{45}NS$ = 860.13) |
| P-33 | m/z = 843.35($C_{64}H_{45}NO$ = 844.07) | P-34 | m/z = 839.36($C_{62}H_{49}NS$ = 840.14) |
| P-35 | m/z = 753.34($C_{55}H_{47}NS$ = 754.05) | P-36 | m/z = 735.35($C_{55}H_{45}NO$ = 735.97) |
| P-37 | m/z = 887.36($C_{66}H_{49}NS$ = 888.19) | P-38 | m/z = 947.41($C_{72}H_{53}NO$ = 948.22) |
| P-39 | m/z = 719.32($C_{54}H_{41}NO$ = 719.93) | P-40 | m/z = 719.32($C_{54}H_{41}NO$ = 719.93) |
| P-41 | m/z = 673.30($C_{49}H_{39}NO_2$ = 673.86) | P-42 | m/z = 725.22($C_{51}H_{35}NS_2$ = 725.97) |
| P-43 | m/z = 759.26($C_{55}H_{37}NOS$ = 759.97) | P-44 | m/z = 759.26($C_{55}H_{37}NOS$ = 759.97) |
| P-45 | m/z = 769.30($C_{57}H_{39}NO_2$ = 769.94) | P-46 | m/z = 769.30($C_{57}H_{39}NO_2$ = 769.94) |
| P-47 | m/z = 768.31($C_{57}H_{40}N_2O$ = 768.96) | P-48 | m/z = 801.25($C_{57}H_{39}NS_2$ = 802.07) |
| P-49 | m/z = 679.29($C_{51}H_{37}NO$ = 679.86) | P-50 | m/z = 771.30($C_{57}H_{41}NS$ = 772.02) |
| P-51 | m/z = 844.35($C_{63}H_{44}N_2O$ = 845.06) | P-52 | m/z = 847.33($C_{63}H_{45}NS$ = 848.12) |
| P-53 | m/z = 997.37($C_{75}H_{51}NS$ = 998.30) | P-54 | m/z = 994.39($C_{75}H_{50}N_2O$ = 995.24) |
| P-55 | m/z = 729.30($C_{55}H_{39}NO$ = 729.92) | P-56 | m/z = 947.36($C_{71}H_{49}NS$ = 948.24) |
| P-57 | m/z = 811.33($C_{60}H_{45}NS$ = 812.09) | P-58 | m/z = 861.34($C_{63}H_{47}NOSi$ = 862.16) |
| P-59 | m/z = 844.35($C_{63}H_{44}N_2O$ = 845.06) | P-60 | m/z = 785.28($C_{57}H_{39}NOS$ = 786.01) |
| P-61 | m/z = 909.44($C_{67}H_{59}NS$ = 910.28) | P-62 | m/z = 811.35($C_{60}H_{45}NO_2$ = 812.03) |
| P-63 | m/z = 1022.43($C_{74}H_{58}N_2OS$ = 1023.35) | P-64 | m/z = 709.26($C_{51}H_{35}NO_3$ = 709.85) |
| P-65 | m/z = 736.25($C_{52}H_{36}N_2OS$ = 736.93) | P-66 | m/z = 795.35($C_{60}H_{45}NO$ = 796.03) |
| P-67 | m/z = 785.28($C_{57}H_{39}NOS$ = 786.01) | P-68 | m/z = 835.29($C_{61}H_{41}NOS$ = 836.07) |
| P-69 | m/z = 779.32($C_{59}H_{41}NO$ = 779.98) | P-70 | m/z = 948.35($C_{70}H_{48}N_2S$ = 949.23) |
| P-71 | m/z = 843.31($C_{63}H_{41}NO_2$ = 844.03) | P-72 | m/z = 803.32($C_{61}H_{41}NO$ = 804.01) |
| P-73 | m/z = 941.31($C_{71}H_{43}NS$ = 942.19) | P-74 | m/z = 917.37($C_{67}H_{51}NOS$ = 918.21) |
| P-75 | m/z = 785.28($C_{57}H_{39}NOS$ = 786.01) | P-76 | m/z = 792.41($C_{58}H_{52}N_2O$ = 793.07) |
| P-77 | m/z = 795.41($C_{58}H_{53}NO_2$ = 796.07) | P-78 | m/z = 785.28($C_{57}H_{39}NOS$ = 786.01) |
| P-79 | m/z = 679.29($C_{51}H_{37}NO$ = 679.86) | P-80 | m/z = 765.31($C_{55}H_{43}NOS$ = 766.02) |
| P-81 | m/z = 769.30($C_{57}H_{39}NO_2$ = 769.94) | P-82 | m/z = 769.30($C_{57}H_{39}NO_2$ = 769.94) |
| P-83 | m/z = 765.31($C_{55}H_{43}NOS$ = 766.02) | P-84 | m/z = 803.41($C_{60}H_{53}NO$ = 804.09) |

TABLE 3-continued

| Compound | FD-MS | Compound | FD-MS |
|---|---|---|---|
| P-85 | m/z = 715.38($C_{53}H_{49}NO$ = 715.98) | P-86 | m/z = 813.40($C_{61}H_{51}NO$ = 814.09) |
| P-87 | m/z = 860.32($C_{63}H_{44}N_2S$ = 861.12) | P-88 | m/z = 850.39($C_{63}H_{50}N_2O$ = 851.11) |
| P-89 | m/z = 761.51($C_{55}H_{15}D_{28}NO$ = 762.13) | P-90 | m/z = 779.36($C_{57}H_{29}D_{10}NO_2$ = 780.01) |
| P-91 | m/z = 643.29($C_{48}H_{37}NO$ = 643.83) | P-92 | m/z = 609.30($C_{45}H_{39}NO$ = 609.81) |
| P-93 | m/z = 789.29($C_{57}H_{40}FNS$ = 790.01) | P-94 | m/z = 796.29($C_{58}H_{40}N_2S$ = 797.03) |
| P-95 | m/z = 603.26($C_{45}H_{33}NO$ = 603.77) | P-96 | m/z = 909.36($C_{68}H_{47}NO_2$ = 910.13) |
| P-97 | m/z = 935.36($C_{70}H_{49}NS$ = 936.23) | P-98 | m/z = 643.29($C_{48}H_{37}NO$ = 643.83) |
| P-99 | m/z = 841.34($C_{61}H_{47}NOS$ = 842.11) | P-100 | m/z = 623.32($C_{46}H_{41}NO$ = 623.84) |
| P-101 | m/z = 751.33($C_{55}H_{45}NS$ = 752.03) | P-102 | m/z = 619.23($C_{45}H_{33}NS$ = 619.83) |
| P-103 | m/z = 751.33($C_{55}H_{45}NS$ = 752.03) | P-104 | m/z = 735.35($C_{55}H_{45}NO$ = 735.97) |
| P-105 | m/z = 783.39($C_{57}H_{53}NS$ = 784.12) | P-106 | m/z = 791.41($C_{59}H_{53}NO$ = 792.08) |
| P-107 | m/z = 633.21($C_{45}H_{31}NOS$ = 633.81) | P-108 | m/z = 831.35($C_{63}H_{45}NO$ = 832.06) |
| P-109 | m/z = 755.32($C_{57}H_{41}NO$ = 755.96) | P-110 | m/z = 617.24($C_{45}H_{31}NO_2$ = 617.75) |
| P-111 | m/z = 887.41($C_{67}H_{53}NO$ = 888.17) | P-112 | m/z = 921.36($C_{69}H_{47}NO_2$ = 922.14) |
| P-113 | m/z = 937.34($C_{69}H_{47}NOS$ = 938.20) | P-114 | m/z = 897.4($C_{65}H_{55}NOS$ = 898.22) |
| P-115 | m/z = 719.32($C_{54}H_{41}NO$ = 719.93) | P-116 | m/z = 907.38($C_{69}H_{49}NO$ = 908.16) |
| P-117 | m/z = 977.62($C_{70}H_7D_{42}NS$ = 978.49) | P-118 | m/z = 791.55($C_{57}H_{17}D_{30}NO$ = 792.19) |
| P-119 | m/z = 723.49($C_{52}H_9D_{30}NO$ = 724.07) | P-120 | m/z = 739.47($C_{52}H_9D_{30}NS$ = 740.13) |
| P-121 | m/z = 679.29($C_{51}H_{37}NO$ = 679.86) | P-122 | m/z = 769.30($C_{57}H_{39}NO_2$ = 769.94) |
| P-123 | m/z = 795.35($C_{60}H_{45}NO$ = 796.03) | P-124 | m/z = 872.12($C_{66}H_{49}NO$ = 872.12) |
| P-125 | m/z = 603.26($C_{45}H_{33}NO$ = 603.77) | P-126 | m/z = 719.32($C_{54}H_{41}NO$ = 719.93) |
| P-127 | m/z = 527.22($C_{39}H_{29}NO$ = 527.67) | P-128 | m/z = 619.23($C_{45}H_{33}NS$ = 619.83) |
| P-129 | m/z = 695.26($C_{51}H_{37}NS$ = 695.92) | P-130 | m/z = 603.26($C_{45}H_{33}NO$ = 603.77) |
| P-131 | m/z = 603.26($C_{45}H_{33}NO$ = 603.77) | P-132 | m/z = 603.26($C_{45}H_3NO$ = 603.77) |
| P-133 | m/z = 603.26($C_{45}H_{33}NO$ = 603.77) | P-134 | m/z = 619.23($C_{45}H_{33}NS$ = 619.83) |
| P-135 | m/z = 661.33($C_{49}H_{43}NO$ = 661.89) | P-136 | m/z = 583.29($C_{43}H_{37}NO$ = 583.78) |
| P-137 | m/z = 603.26($C_{45}H_{33}NO$ = 603.77) | P-138 | m/z = 589.33($C_{43}H_{43}NO$ = 589.82) |
| P-139 | m/z = 665.37($C_{49}H_{47}NO$ = 665.92) | P-140 | m/z = 601.33($C_{44}H_{43}NO$ = 601.83) |
| P-141 | m/z = 641.37($C_{47}H_{47}NO$ = 641.9) | P-142 | m/z = 563.32($C_{41}H_{41}NO$ = 563.79) |
| P-143 | m/z = 627.35($C_{46}H_{45}NO$ = 627.87) | P-144 | m/z = 679.38($C_{50}H_{49}NO$ = 679.95) |
| P-145 | m/z = 693.27($C_{51}H_{35}NO_2$ = 693.85) | P-146 | m/z = 617.24($C_{45}H_{31}NO_2$ = 617.75) |
| P-147 | m/z = 617.24($C_{45}H_{31}NO_2$ = 617.75) | P-148 | m/z = 693.27($C_{51}H_{35}NO_2$ = 693.85) |
| P-149 | m/z = 725.22($C_{51}H_{35}NS_2$ = 725.97) | P-150 | m/z = 649.19($C_{45}H_{31}NS_2$ = 649.87) |
| P-151 | m/z = 725.22($C_{51}H_{35}NS_2$ = 725.97) | P-152 | m/z = 617.24($C_{45}H_{31}NO_2$ = 617.75) |
| P-153 | m/z = 741.27($C_{55}H_{35}NO_2$ = 741.89) | P-154 | m/z = 817.3($C_{61}H_{39}NO_2$ = 817.99) |
| P-155 | m/z = 771.21($C_{55}H_{33}NS_2$ = 772) | P-156 | m/z = 815.28($C_{61}H_{37}NO_2$ = 815.97) |
| P-157 | m/z = 693.27($C_{51}H_{35}NO_2$ = 693.85) | P-158 | m/z = 708.26($C_{51}H_{36}N_2S$ = 708.92) |
| P-159 | m/z = 768.31($C_{57}H_{40}N_2O$ = 768.96) | P-160 | m/z = 692.28($C_{51}H_{36}N_2O$ = 692.86) |
| P-161 | m/z = 617.24(C45H31NO2 = 617.75) | P-162 | m/z = 617.24(C45H31NO2 = 617.75) |
| P-163 | m/z = 617.24(C45H31NO2 = 617.75) | P-164 | m/z = 617.24(C45H31NO2 = 617.75) |
| P-165 | m/z = 741.27(C55H35NO2 = 741.89) | P-166 | m/z = 633.21(C45H31NOS = 633.81) |
| P-167 | m/z = 633.21(C45H31NOS = 633.81) | P-168 | m/z = 649.19(C45H31NS2 = 649.87) |
| P-169 | m/z = 693.27(C51H35NO2 = 693.85) | P-170 | m/z = 693.27(C51H35NO2 = 693.85) |
| P-171 | m/z = 709.24(C51H35NOS = 709.91) | P-172 | m/z = 693.27(C51H35NO2 = 693.85) |
| P-173 | m/z = 623.27(C45H25D6NO2 = 623.78) | P-174 | m/z = 622.27(C45H26D5NO2 = 622.78) |
| P-175 | m/z = 630.32(C45H18D13NO2 = 630.83) | P-176 | m/z = 624.28(C45H24D7NO2 = 624.79) |
| P-177 | m/z = 597.27(C43H35NO2 = 597.76) | P-178 | m/z = 643.29(C48H37NO = 643.83) |
| P-179 | m/z = 693.27(C51H35NO2 = 693.85) | P-180 | m/z = 693.27(C51H35NO2 = 693.85) |
| P-181 | m/z = 698.3(C51H30D5NO2 = 698.88) | P-182 | m/z = 693.27(C51H35NO2 = 693.85) |
| P-183 | m/z = 693.27(C51H35NO2 = 693.85) | P-184 | m/z = 673.3(C49H39NO2 = 673.86) |

Manufacturing Evaluation of Organic Electronic Elements

Example 1

Green Organic Light Emitting Device
(Emitting-Auxiliary Layer)

After vacuum depositing 4,4',4"-tris[2-naphthyl(phenyl)amino]triphenylamine (hereinafter abbreviated as 2-TNATA) on the ITO layer (anode) formed on the glass substrate to form a hole injection layer with a thickness of 60 nm, and on the hole injection layer, N,N'-bis(1-naphthalenyl)-N,N'-bis-phenyl-(1,1'-biphenyl)-4,4'-diamine (hereinafter abbreviated as NPB) was vacuum deposited to a thickness of 60 nm to form a hole transport layer.

Subsequently, compound P-11 of the present invention was vacuum deposited on the hole transport layer to a thickness of 20 nm to form an emitting-auxiliary layer, and 4,4'-N,N'-dicarbazole-biphenyl (hereinafter abbreviated as CBP) was used as a host material, and tris(2-phenylpyridine)-iridium (hereinafter abbreviated as Ir(ppy)$_3$) was used as a dopant material, and the dopant was doped at a weight of 95:5 to form an emitting layer with a thickness of 30 nm.

Next, (1,1'-biphenyl-4-olato)bis(2-methyl-8-quinolinolato)aluminum (hereinafter abbreviated as BAlq) is vacuum deposited on the emitting layer to form a hole blocking layer with a thickness of 10 nm, and tris(8-quinolinol) aluminum (hereinafter abbreviated as Alq$_3$) was vacuum deposited to a thickness of 40 nm on the hole blocking layer to form an electron transport layer. Afterwards, LiF was deposited on the electron transport layer to form an electron injection layer with a thickness of 0.2 nm, and then Al was deposited to form a cathode with a thickness of 150 nm.

Example 2 to Example 28

An organic light emitting device was manufactured in the same manner as in Example 1, except that the compound of the present invention shown in Table 4 was used as the emitting-auxiliary layer material instead of the compound P-11 of the present invention.

Comparative Example 1 to Comparative Example 4

An organic electroluminescent device was manufactured in the same manner as in Example 1, except that Comparative Compounds A to Comparative Compound D were used instead of Compound P-11 of the present invention as the emitting-auxiliary layer material.

[comparative compound A]

[comparative compound B]

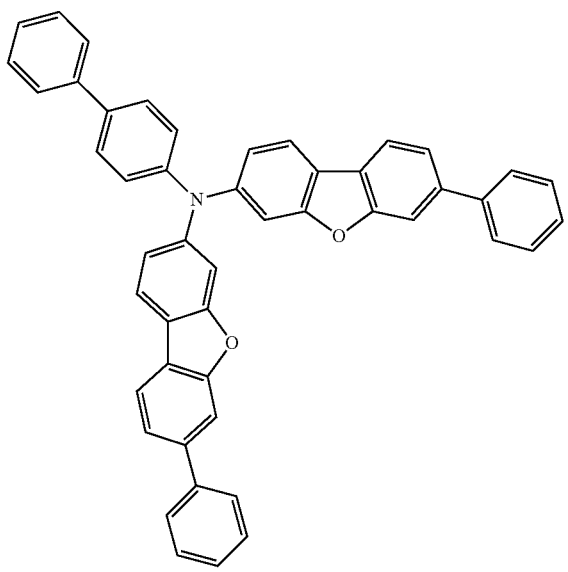

[comparative compound C]

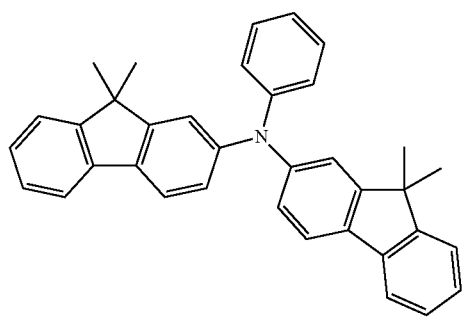

[comparative compound D]

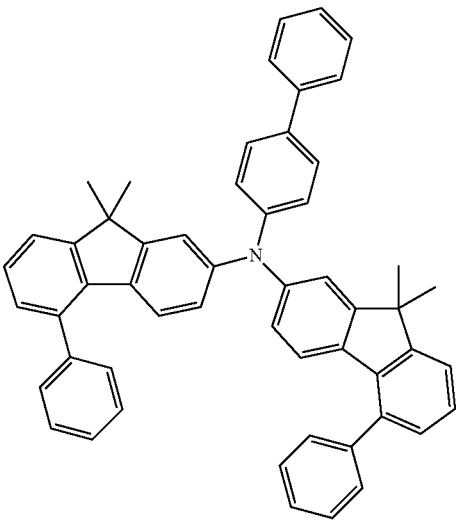

Example 29

An organic light emitting device was manufactured in the same manner as in Example 1, except that the emitting-auxiliary layer was formed by vacuum depositing compound P-91 of the present invention to a thickness of 25 nm on the hole transport layer.

Example 30 to Example 55

An organic light emitting device was manufactured in the same manner as in Example 29, except that the compounds of the present invention shown in Table 5 were used instead of the compound P-91 of the present invention as the emitting-auxiliary layer material.

Comparative Example 5 to Comparative Example 8

An organic electroluminescent device was manufactured in the same manner as in Example 29, except that Comparative Compounds A to Comparative Compound D were used instead of Compound P-91 of the present invention as the emitting-auxiliary layer material.

Example 56

An organic light emitting device was manufactured in the same manner as in Example 1, except that, as an emitting auxiliary layer material, the compound P-40 of the present invention was vacuum deposited to a thickness of 15 nm to form a first emitting-auxiliary layer, and then, on the first emitting-auxiliary layer, the compound PA-1 was vacuum deposited to a thickness of 5 nm to form a second emitting-auxiliary layer.

[PA-1]

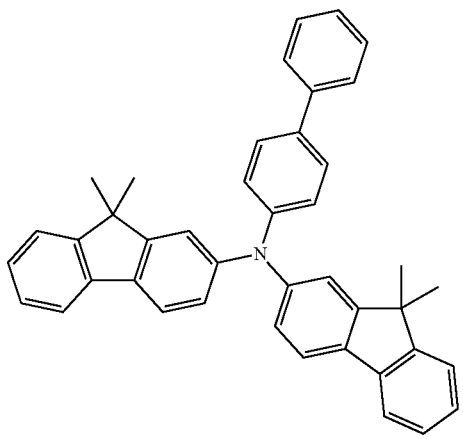

Example 57 to Example 71

An organic light emitting device was manufactured in the same manner as in Example 54, except that the compounds of the present invention and the compound PA-1 shown in Table 6 were used as the first emitting-auxiliary layer material and the second emitting-auxiliary layer material.

Comparative Example 9 to Comparative Example 16

An organic light emitting device was manufactured in the same manner as in Example 54, except that Comparative Compounds A to Comparative Compound D and the compound PA-1 shown in Table 6 were used as the first emitting-auxiliary layer material and the second emitting-auxiliary layer material.

Example 72

An organic light emitting device was manufactured in the same manner as in Example 1, except that, as an emitting auxiliary layer material, the compound P-91 of the present invention was vacuum deposited to a thickness of 15 nm to form a first emitting-auxiliary layer, and then, on the first emitting-auxiliary layer, the compound PA-1 was vacuum deposited to a thickness of 10 nm to form a second emitting-auxiliary layer.

Example 73 to Example 91

An organic light emitting device was manufactured in the same manner as in Example 70, except that the compounds of the present invention and the compound PA-1 shown in Table 7 were used as the first emitting-auxiliary layer material and the second emitting-auxiliary layer material.

Comparative Example 17 to Comparative Example 24

An organic light emitting device was manufactured in the same manner as in Example 70, except that Comparative Compounds A to Comparative Compound D and the compound PA-1 shown in Table 7 were used as the first emitting-auxiliary layer material and the second emitting-auxiliary layer material.

A forward bias direct current voltage was applied to the organic electroluminescent device manufactured by Examples 1 to 89 of the present invention and Comparative Examples 1 to 24, and the electroluminescence (EL) characteristics were measured using PR-650 from Photoresearch. As a result of the measurement, T95 life was measured at a standard luminance of 5000 cd/m$^2$ through life measuring apparatus manufactured by McScience. Table 4 to Table 7 show the results of Manufacturing evaluation of elements.

TABLE 4

| | compound | Voltage | Current Density (mA/cm$^2$) | Brightness (cd/m$^2$) | Efficiency (cd/A) | T(95) |
|---|---|---|---|---|---|---|
| comparative example(1) | comparative compound A | 5.9 | 13.0 | 5000.0 | 38.4 | 100.3 |
| comparative example(2) | comparative compound B | 6.1 | 12.6 | 5000.0 | 39.8 | 99.6 |
| comparative example(3) | comparative compound C | 5.8 | 13.3 | 5000.0 | 37.5 | 102.1 |
| comparative example(4) | comparative compound D | 5.7 | 13.8 | 5000.0 | 36.2 | 103.5 |
| example(1) | P-11 | 5.4 | 10.6 | 5000.0 | 47.0 | 131.0 |
| example(2) | P-25 | 5.4 | 10.8 | 5000.0 | 46.3 | 129.4 |
| example(3) | P-27 | 5.4 | 10.3 | 5000.0 | 48.5 | 124.3 |
| example(4) | P-30 | 5.3 | 10.2 | 5000.0 | 48.8 | 125.5 |
| example(5) | P-32 | 5.3 | 9.9 | 5000.0 | 50.6 | 131.4 |
| example(6) | P-40 | 4.9 | 9.1 | 5000.0 | 54.9 | 135.9 |
| example(7) | P-49 | 4.9 | 9.1 | 5000.0 | 55.2 | 136.6 |
| example(8) | P-50 | 5.2 | 9.7 | 5000.0 | 51.4 | 133.7 |
| example(9) | P-57 | 5.4 | 10.9 | 5000.0 | 45.9 | 123.2 |
| example(10) | P-66 | 5.0 | 9.6 | 5000.0 | 52.1 | 134.8 |
| example(11) | P-69 | 5.3 | 8.9 | 5000.0 | 56.0 | 132.2 |
| example(12) | P-74 | 5.4 | 10.7 | 5000.0 | 46.6 | 128.6 |
| example(13) | P-75 | 5.1 | 10.2 | 5000.0 | 48.8 | 127.7 |
| example(14) | P-78 | 5.4 | 10.5 | 5000.0 | 47.4 | 126.2 |
| example(15) | P-80 | 5.1 | 10.1 | 5000.0 | 49.3 | 128.0 |
| example(16) | P-82 | 5.4 | 9.7 | 5000.0 | 51.3 | 130.6 |
| example(17) | P-84 | 5.0 | 10.1 | 5000.0 | 49.7 | 135.2 |
| example(18) | P-86 | 5.0 | 9.5 | 5000.0 | 52.6 | 130.1 |
| example(19) | P-87 | 5.3 | 11.1 | 5000.0 | 45.1 | 132.5 |
| example(20) | P-97 | 5.1 | 9.1 | 5000.0 | 54.8 | 134.3 |

TABLE 4-continued

|  | compound | Voltage | Current Density (mA/cm²) | Brightness (cd/m²) | Efficiency (cd/A) | T(95) |
|---|---|---|---|---|---|---|
| example(21) | P-110 | 5.6 | 12.2 | 5000.0 | 40.9 | 110.4 |
| example(22) | P-112 | 5.2 | 10.0 | 5000.0 | 50.0 | 133.0 |
| example(23) | P-120 | 5.0 | 8.9 | 5000.0 | 55.9 | 137.1 |
| example(24) | P-121 | 5.2 | 9.4 | 5000.0 | 53.2 | 129.8 |
| example(25) | P-122 | 5.2 | 10.5 | 5000.0 | 47.8 | 122.1 |
| example(26) | P-123 | 5.1 | 9.3 | 5000.0 | 53.8 | 131.9 |
| example(27) | P-127 | 5.6 | 12.5 | 5000.0 | 40.0 | 109.8 |
| example(28) | P-139 | 5.0 | 9.7 | 5000.0 | 51.4 | 129.9 |

TABLE 5

|  | compound | Voltage | Current Density (mA/cm²) | Brightness (cd/m²) | Efficiency (cd/A) | T(95) |
|---|---|---|---|---|---|---|
| comparative example(5) | comparative compound A | 6.5 | 17.3 | 5000.0 | 28.9 | 88.7 |
| comparative example(6) | comparative compound B | 6.4 | 15.6 | 5000.0 | 32.1 | 98.6 |
| comparative example(7) | comparative compound C | 6.0 | 20.0 | 5000.0 | 25.0 | 85.5 |
| comparative example(8) | comparative compound D | 5.9 | 18.1 | 5000.0 | 27.6 | 94.3 |
| example(29) | P-91 | 5.3 | 11.8 | 5000.0 | 42.2 | 118.9 |
| example(30) | P-95 | 5.0 | 9.9 | 5000.0 | 50.7 | 135.5 |
| example(31) | P-98 | 5.1 | 9.9 | 5000.0 | 50.3 | 135.1 |
| example(32) | P-100 | 5.3 | 9.8 | 5000.0 | 51.2 | 130.3 |
| example(33) | P-102 | 5.4 | 12.6 | 5000.0 | 39.7 | 113.8 |
| example(34) | P-107 | 5.3 | 11.6 | 5000.0 | 43.0 | 119.4 |
| example(35) | P-110 | 5.5 | 12.8 | 5000.0 | 39.0 | 109.2 |
| example(36) | P-115 | 5.5 | 11.5 | 5000.0 | 43.6 | 120.0 |
| example(37) | P-125 | 5.3 | 11.3 | 5000.0 | 44.4 | 121.0 |
| example(38) | P-126 | 5.4 | 12.5 | 5000.0 | 40.1 | 115.4 |
| example(39) | P-127 | 5.6 | 12.9 | 5000.0 | 38.8 | 108.7 |
| example(40) | P-128 | 5.4 | 12.3 | 5000.0 | 40.8 | 116.2 |
| example(41) | P-129 | 5.3 | 11.1 | 5000.0 | 45.1 | 122.6 |
| example(42) | P-130 | 5.5 | 11.4 | 5000.0 | 43.9 | 120.8 |
| example(43) | P-131 | 5.5 | 11.0 | 5000.0 | 45.3 | 124.7 |
| example(44) | P-132 | 5.3 | 11.2 | 5000.0 | 44.7 | 121.3 |
| example(45) | P-133 | 5.4 | 12.0 | 5000.0 | 41.7 | 118.7 |
| example(46) | P-134 | 5.4 | 12.1 | 5000.0 | 41.3 | 117.1 |
| example(47) | P-135 | 5.4 | 10.2 | 5000.0 | 48.8 | 128.5 |
| example(48) | P-136 | 5.5 | 11.9 | 5000.0 | 42.1 | 121.9 |
| example(49) | P-137 | 5.5 | 11.5 | 5000.0 | 43.5 | 120.5 |
| example(50) | P-138 | 5.4 | 10.3 | 5000.0 | 48.7 | 127.2 |
| example(51) | P-146 | 5.3 | 11.4 | 5000.0 | 43.8 | 122.3 |
| example(52) | P-148 | 5.3 | 11.0 | 5000.0 | 45.3 | 121.9 |
| example(53) | P-152 | 5.3 | 11.3 | 5000.0 | 44.2 | 122.8 |
| example (54) | P-161 | 5.4 | 10.2 | 5000.0 | 48.8 | 126.8 |
| example (55) | P-178 | 5.4 | 10.5 | 5000.0 | 47.6 | 125.4 |

TABLE 6

|  | First emitting-auxiliary layer | Second emitting-auxiliary layer | Voltage | Current Density (mA/cm²) | Brightness (cd/m²) | Efficiency (cd/A) | T(95) |
|---|---|---|---|---|---|---|---|
| comparative example(9) | comparative compound A | PA-1 | 6.0 | 13.3 | 5000.0 | 37.5 | 99.9 |
| comparative example(10) | comparative compound B | PA-1 | 5.8 | 12.5 | 5000.0 | 40.1 | 104.3 |
| comparative example(11) | comparative compound C | PA-1 | 5.7 | 15.0 | 5000.0 | 33.4 | 95.4 |
| comparative example(12) | comparative compound D | PA-1 | 5.4 | 13.9 | 5000.0 | 36.0 | 101.5 |

TABLE 6-continued

|  | First emitting-auxiliary layer | Second emitting-auxiliary layer | Voltage | Current Density (mA/cm$^2$) | Brightness (cd/m$^2$) | Efficiency (cd/A) | T(95) |
|---|---|---|---|---|---|---|---|
| comparative example(13) | PA-1 | comparative compound A | 5.9 | 13.9 | 5000.0 | 35.9 | 100.2 |
| comparative example(14) | PA-1 | comparative compound B | 5.9 | 12.1 | 5000.0 | 41.2 | 103.8 |
| comparative example(15) | PA-1 | comparative compound C | 5.5 | 15.7 | 5000.0 | 31.8 | 97.1 |
| comparative example(16) | PA-1 | comparative compound D | 5.6 | 13.4 | 5000.0 | 37.3 | 102.0 |
| example(56) | P-40 | PA-1 | 4.7 | 8.4 | 5000.0 | 59.8 | 143.1 |
| example(57) | P-49 | PA-1 | 4.7 | 8.2 | 5000.0 | 60.9 | 142.6 |
| example(58) | P-82 | PA-1 | 5.2 | 8.8 | 5000.0 | 57.0 | 136.5 |
| example(59) | P-97 | PA-1 | 4.9 | 8.4 | 5000.0 | 59.2 | 140.5 |
| example(60) | P-110 | PA-1 | 5.5 | 11.5 | 5000.0 | 43.4 | 115.3 |
| example(61) | P-127 | PA-1 | 5.5 | 11.6 | 5000.0 | 43.0 | 114.8 |
| example(62) | P-121 | PA-1 | 5.1 | 8.6 | 5000.0 | 58.0 | 134.6 |
| example(63) | P-123 | PA-1 | 5.0 | 8.7 | 5000.0 | 57.5 | 134.5 |
| example(64) | PA-1 | P-40 | 4.7 | 8.2 | 5000.0 | 61.3 | 145.5 |
| example(65) | PA-1 | P-49 | 4.7 | 8.0 | 5000.0 | 62.2 | 143.8 |
| example(66) | PA-1 | P-82 | 5.1 | 8.5 | 5000.0 | 58.7 | 138.2 |
| example(67) | PA-1 | P-97 | 4.9 | 8.2 | 5000.0 | 60.7 | 142.5 |
| example(68) | PA-1 | P-121 | 5.1 | 8.4 | 5000.0 | 59.3 | 136.3 |
| example(69) | PA-1 | P-123 | 4.9 | 8.5 | 5000.0 | 58.6 | 136.4 |
| example(70) | PA-1 | P-110 | 5.5 | 11.7 | 5000.0 | 42.7 | 113.7 |
| example(71) | PA-1 | P-127 | 5.6 | 11.4 | 5000.0 | 44.0 | 114.9 |

TABLE 7

|  | First emitting-auxiliary layer | Second emitting-auxiliary layer | Voltage | Current Density (mA/cm$^2$) | Brightness (cd/m$^2$) | Efficiency (cd/A) | T(95) |
|---|---|---|---|---|---|---|---|
| comparative example(17) | comparative compound A | PA-1 | 6.2 | 14.9 | 5000.0 | 33.5 | 95.4 |
| comparative example(18) | comparative compound B | PA-1 | 6.1 | 13.3 | 5000.0 | 37.7 | 101.1 |
| comparative example(19) | comparative compound C | PA-1 | 5.8 | 16.7 | 5000.0 | 30.0 | 91.8 |
| comparative example(20) | comparative compound D | PA-1 | 5.6 | 15.2 | 5000.0 | 33.0 | 99.5 |
| comparative example(21) | PA-1 | comparative compound A | 5.9 | 15.2 | 5000.0 | 32.8 | 96.7 |
| comparative example(22) | PA-1 | comparative compound B | 5.9 | 13.1 | 5000.0 | 38.1 | 100.7 |
| comparative example(23) | PA-1 | comparative compound C | 5.5 | 17.2 | 5000.0 | 29.1 | 92.3 |
| comparative example(24) | PA-1 | comparative compound D | 5.6 | 14.6 | 5000.0 | 34.2 | 98.6 |
| example(72) | P-95 | PA-1 | 4.8 | 8.9 | 5000.0 | 56.1 | 143.1 |
| example(73) | P-98 | PA-1 | 4.9 | 9.0 | 5000.0 | 55.5 | 142.9 |
| example(74) | P-100 | PA-1 | 5.0 | 8.5 | 5000.0 | 58.7 | 139.8 |
| example(75) | P-125 | PA-1 | 5.2 | 10.2 | 5000.0 | 48.8 | 126.2 |
| example(76) | P-126 | PA-1 | 5.3 | 11.1 | 5000.0 | 45.1 | 120.5 |
| example(77) | P-127 | PA-1 | 5.5 | 11.7 | 5000.0 | 42.9 | 113.1 |
| example(78) | P-133 | PA-1 | 5.2 | 10.8 | 5000.0 | 46.2 | 123.0 |
| example(79) | P-135 | PA-1 | 5.3 | 9.8 | 5000.0 | 51.0 | 135.4 |
| example(80) | P-136 | PA-1 | 5.4 | 11.3 | 5000.0 | 44.2 | 124.2 |
| example(81) | P-137 | PA-1 | 5.4 | 10.6 | 5000.0 | 47.3 | 124.8 |
| example(82) | PA-1 | P-95 | 4.7 | 8.5 | 5000.0 | 58.7 | 144.5 |
| example(83) | PA-1 | P-98 | 4.9 | 8.7 | 5000.0 | 57.3 | 143.4 |
| example(84) | PA-1 | P-100 | 5.1 | 9.3 | 5000.0 | 53.5 | 135.1 |
| example(85) | PA-1 | P-125 | 5.2 | 10.1 | 5000.0 | 49.6 | 128.7 |
| example(86) | PA-1 | P-126 | 5.3 | 10.8 | 5000.0 | 46.2 | 122.2 |
| example(87) | PA-1 | P-127 | 5.5 | 11.4 | 5000.0 | 44.0 | 115.0 |
| example(88) | PA-1 | P-133 | 5.3 | 10.2 | 5000.0 | 48.8 | 124.9 |
| example(89) | PA-1 | P-135 | 5.3 | 10.0 | 5000.0 | 50.2 | 132.6 |
| example(90) | PA-1 | P-136 | 5.4 | 11.6 | 5000.0 | 43.1 | 121.8 |
| example(91) | PA-1 | P-137 | 5.3 | 10.3 | 5000.0 | 48.4 | 127.3 |

As can be seen from the results in Table 4 to Table 7, when a green organic electroluminescent device is manufactured using the material for an organic electroluminescent device of the present invention as a material for the emitting-auxiliary layer, the driving voltage, luminous efficiency, and lifespan of the organic electroluminescent device can be improved compared to the comparative examples using Comparative Compounds A to Comparative Compounds D, which have similar basic structures to the compound of the present invention.

Comparative Compounds A to Comparative Compounds D are similar to the compounds of the present invention in that fluorine or dibenzofuran, or dibenzothiophene is substituted in the tertiary amine compound, but the compounds of the present invention differ from comparative compounds in that at least one fluorene and at least one dibenzofuran or dibenzothiophene are substituted in the molecule.

In the case of Comparative Compound A and Comparative Compound B, which are tertiary amine compounds substituted with dibenzofuran or dibenzothiophene, because they contain hetero elements, their stability against electrons increases and they have a longer lifespan than Comparative Compound C and Comparative Compound D, but they require a high driving voltage. In the case of Comparative Compound C and Comparative Compound D, which are fluorene-substituted tertiary amine compounds, they exhibit a low driving voltage, but the 9th position of the fluorene moiety is vulnerable to electric charges, resulting in a relatively short lifespan.

However, it is believed that unlike the comparative compounds, the compound of the present invention has at least one fluorene and at least one dibenzofuran or dibenzothiophene substituted in the molecule, so that not only can the advantages of each moiety be utilized, but it has an energy level suitable for the emitting-auxiliary layer, which affects the performance of the entire element.

Table 4 shows examples where substituents are each introduced into at least one fluorene and at least one dibenzofuran or dibenzothiophene among the compounds of the present invention.

In more detail, when substituents are introduced to fluorene, dibenzofuran, and dibenzothiophene, due to steric hindrance of molecules, a high T1 energy level is formed, and pi-pi stacking between molecules is suppressed, and due to the substituent, the molecular structure shields the amine moiety, and the electrons in the molecule are separated toward the amine moiety, causing the charge to move relatively quickly, therefore the charge balance of the entire element is improved, and although the planarity of the molecules decreases during device deposition, but the Tg value decreases, making it possible to manufacture elements even at relatively low temperatures during deposition.

Also, as the distance between molecules increases due to steric hindrance, the effect of lowering the crystallinity of the thin film, that is, creating an amorphous state, is believed to improve hole mobility and increase the stability of the compound itself.

Moreover, by introducing additional substituents to fluorene, dibenzofuran, and dibenzothiophene, conjugation increases, the electron cloud of HOMO expands, and the HOMO-LUMO band gap also increases, thereby increasing hole injection and hole transport characteristics, allowing holes to be transferred from the hole transport layer to the emitting layer, and having an energy level suitable as an emitting-auxiliary layer that must block electrons coming from the emitting layer.

Table 5 is a manufacturing evaluation of an element conducted to confirm the characteristics of the compounds of the present invention when a substituent is introduced into one of fluorene, dibenzofuran, or dibenzothiophene. In the manufacturing evaluation of the element, the better results were obtained in Examples 29 to 53 using the compounds of the present invention than in Comparative Examples 5 to 8.

In more detail, among the compounds of the present invention, when an amine group was substituted at position 1 of dibenzofuran, generally better device results were obtained than when an amine group was substituted at other positions. Among them, when a substituent was introduced at position 7 or 8 of dibenzofuran, significantly excellent measurement results of the element were obtained.

When additional substituents are introduced, the steric hindrance of the structure increases as described above, and when an amine group is substituted at position 1 of dibenzofuran, the effect of steric hindrance is greater when an additional substituent is introduced at position 8 than when an additional substituent is introduced at position 7 of dibenzofuran.

However, when the 7th position of dibenzofuran is substituted with an alkyl group, such as tert-butyl or adamantyl group, which have very large bulkiness among alkyl groups, steric hindrance similar to that of substitution at the 8th position occurs, resulting in excellent device results.

When an alkyl group, which can greatly increase steric hindrance, is substituted, mobility decreases due to steric hindrance, but the effect of suppressing the formation of crystalline substances is significant, so it is believed to have an advantageous effect during deposition of elements.

It is judged that when an amine group is introduced at position 1 of dibenzofuran and a substituent is introduced at position 8 of dibenzofuran, steric hindrance characteristics are maximized compared to when an amine group or substituent is introduced at any other position of dibenzofuran, so HOMO is formed at a high level and mobility is also improved, resulting in low voltage characteristics. Also, it can be seen that by protecting the active site by introducing an additional substituent at position 8, the active site of dibenzofuran, (a position with high reactivity due to low electron density), the chemical stability of the structure itself is increased and the lifespan is also improved.

Even in the case of dibenzothiophene with an amine group and substituent introduced at the same substitution position, excellent results of elements were obtained compared to the comparative compound. However, overall, better results were obtained in a structure substituted with dibenzofuran, which has relatively greater structural stability including a more electronegative O atom.

Even in the case of fluorene, different results were obtained for each substitution position. In particular, even in the case of a structure in which an amine group was substituted at position 2, better results were obtained than when an amine group was substituted at other positions. It is believed that this is because, for fluorene, position 2 is the active site, so when an amine group is substituted in that region, a high HOMO is formed, mobility is also improved, and has low voltage characteristics.

In the case of fluorene, when additional substituents other than amine groups are introduced, conjugation is prolonged as described above, so there is an advantage in terms of lifespan, but mobility appears to decrease and driving voltage increases.

That is, among the compounds of the present invention, it can be confirmed that high efficiency, long lifespan, and low voltage characteristics are exhibited in the structure in which 1-dibenzofuran and 2-fluorene are substituted with a substituent introduced at the 7th or 8th position. This is because 2-fluorene compensates for the relatively poor mobility of dibenzofuran, and 1-dibenzofuran, which has a substituent introduced at position 7 or 8, which has a long-life structure, compensates for the relatively poor lifespan characteristics of 2-fluorene, creating a synergistic effect.

The examples shown in Tables 4 and 5 are evaluation examples of elements composed of only one emitting-auxiliary layer, and the examples shown in Tables 6 and 7 are evaluation examples of elements composed of 2 emitting-auxiliary layers.

PA-1 used in Tables 5 and 6 is a fluorene-based compound generally used in an emitting-auxiliary layer, and it was confirmed that when manufacturing an element with 2 emitting-auxiliary layers using PA-1, comparative compounds, and compounds of the present invention, the overall performance was improved compared to an element consisting of only one emitting-auxiliary layer made of the same material.

In the case, when 2 emitting-auxiliary layers exist, different HOMO-LUMO energy levels are formed depending on the material applied to each emitting-auxiliary layer, by appropriately controlling the HOMO-LUMO energy levels of the first and second emitting-auxiliary layers, the interaction with the emitting layer (transfer of holes to the emitting layer and blocking electrons from the emitting layer) can be controlled.

In the case of the first emitting-auxiliary layer, hole injection from the hole transport layer to the emitting-auxiliary layer must be performed well, and in the case of the second emitting-auxiliary layer, hole injection from the emitting-auxiliary layer to the emitting layer must be performed better, and it is judged that more appropriate hole injection is achieved when the compound of the present invention is applied to the first and second emitting-auxiliary layers than the comparative compound.

In particular, among the compounds of the present invention, as mentioned above, it was confirmed that excellent results are obtained when compounds with additional substituents introduced into fluorene, and dibenzofuran, or dibenzothiophene are applied as the first or second emitting-auxiliary layer.

When either $Ar^1$ or $Ar^2$ is hydrogen, the structure with a substituent in dibenzofuran showed excellent characteristics, and among the compounds of the present invention, in the case of a structure containing dibenzofuran substituted with an alkyl group with high steric hindrance at position 7 and an amine group at position 1, when used in the first emitting-auxiliary layer, as described above, since mobility is relatively low and hole mobility can be effectively controlled, the efficiency of the element can be greatly increased. In the case of a structure in which an additional substituent is introduced at position 8 and the amine group contains dibenzofuran at position 1, the HOMO-LUMO band gap is formed wide in the second emitting-auxiliary layer, so not only the hole injection characteristics but also overall performance of the element is significantly improved by effectively blocking electrons from the emitting layer.

Therefore, the compound of the present invention, which satisfies all of the relevant compositions, showed significant effects in terms of drive, efficiency, and lifespan of element data compared to comparative compounds, and it suggests that even if the basic molecular structure is similar to Comparative Compound A to Comparative Compound D and the compound of the present invention, the properties of the compound, such as hole characteristics, light efficiency characteristics, energy level, hole injection and mobility characteristics, charge balance between holes and electrons, volume density, and intermolecular distance, may vary depending on the substitution position and composition of the substituents, and also rather than one configuration affecting the results of the entire element, the performance of the element may vary due to complex factors.

In the case of an emitting-auxiliary layer, it is necessary to understand the interrelationship between the hole transport layer and the emitting layer (host), so even if a similar core is used, it is very difficult even for a person skilled in the art to infer the characteristics of the emitting-auxiliary layer using the compound of the present invention.

Additionally, in the above-described device manufacturing evaluation results, the characteristics of elements were explained by applying the compound of the present invention only to the emitting-auxiliary layer, but the compound of the present invention can be applied to the hole transport layer or applied to both the hole transport layer and the emitting-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

INDUSTRIAL AVAILABILITY

According to the present invention, it is possible to manufacture an organic device having excellent device characteristics of high luminance, high light emission and long life, and thus has industrial applicability.

What is claimed is:
1. A compound of Formula 1:

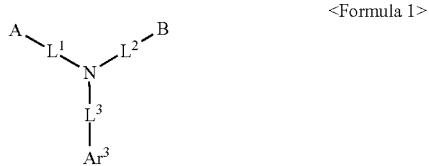

<Formula 1> wherein:
1) A is

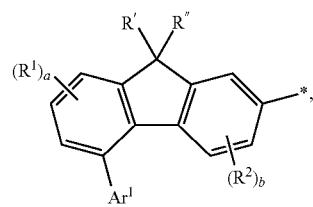

2) B is

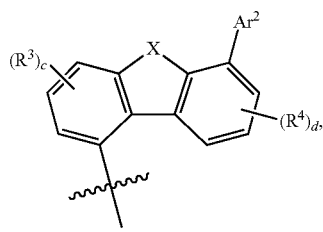

3) X is O or S,
4) $R^1$, $R^2$, $R^3$ and $R^4$ are each independently the same or different, and each independently selected from the group consisting of hydrogen; deuterium; halogen; a cyano group; a nitro group; an $C_6$-$C_{60}$ aryl group; a fluorenyl group; a $C_2$-$C_{60}$ heterocyclic group including at least one heteroatom of O, N, S, Si and P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group, and an adjacent plurality of $R^1$s or of plurality of $R^2$s or of plurality of $R^3$s or of plurality of $R^4$s may be bonded to each other to form an aromatic hydrocarbon ring,
5) R' and R" are each independently selected from the group consisting of an $C_6$-$C_{60}$ aryl group; a $C_1$-$C_{60}$ alkyl group,
6) a, b, c and d are each independently an integer of 0 to 3,
7) $Ar^1$ is a hydrogen; or deuterium,
8) $Ar^2$ is an $C_6$-$C_{60}$ aryl group; or a $C_1$-$C_{60}$ alkyl group,
9) $Ar^3$ is a substituent represented by Formula Ar-5:

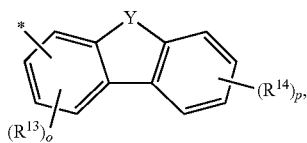

Formula Ar-5 wherein $R^{13}$ and $R^{14}$ are the same as the definition of $R^1$ above,
o is an integer of 0 to 3, p is an integer of 0 to 4,
Y is O, S, $CR^xR^y$ or $NR^z$,
$R^x$, $R^y$ and $R^z$ are the same as the definition of R' above,
10) $L^1$, $L^2$ and $L^3$ are each independently a single bond or a $C_6$-$C_{60}$ arylene group,
11) * refers to the position to be bonded to $L^1$ of Formula 1, or refers to the position to be bonded to $L^3$ of Formula Ar-5,
12) ⌇⌇⌇ refers to the position to be bonded to $L^2$ of Formula 1,
13) wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_6$-$C_{20}$ aryloxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_1$-$C_{20}$ heteroalkyl group; a $C_7$-$C_{20}$ arylalkyl group; and a $C_8$-$C_{20}$ arylalkenyl group, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein at least one of $L^1$ to $L^3$ is represented by any of Formulas L-1 to L-3:

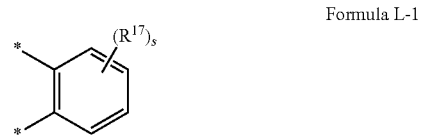

Formula L-1

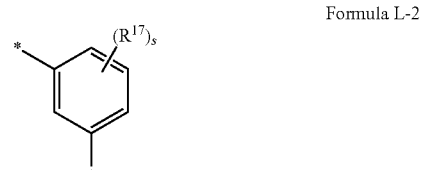

Formula L-2

Formula L-3 wherein:
1) $R^{17}$ is the same as the definition of $R^1$,
2) s is an integer of 0 to 4,
3) * means the position to be bonded.

3. The compound of claim 1, wherein both $L^1$ and $L^2$ are a single bond.

4. An organic electronic element comprising a first electrode; a second electrode; and an organic material layer formed between the first electrode and the second electrode: wherein the organic material layer comprises a compound represented by Formula 1 according to claim 1.

5. The organic electronic element of claim 4, wherein the organic material layer comprises an emitting layer; and a hole transport band formed between the first electrode and the emitting layer; wherein the hole transport band comprises the compound represented by Formula 1.

6. The organic electronic element of claim 5, wherein the hole transport band comprises an emitting auxiliary layer and the emitting auxiliary layer comprises a compound represented by Formula 1.

7. The organic electronic element of claim 6, wherein the emitting-auxiliary layer comprises a first emitting-auxiliary layer adjacent to the hole transport layer and a second emitting-auxiliary layer adjacent to the emitting layer, wherein the first emitting-auxiliary layer and/or the second emitting-auxiliary layer comprise the compound represented by Formula 1.

8. The organic electronic element of claim 4, wherein the organic material layer comprises an emitting layer; a hole transport layer formed between the first electrode and the emitting layer; and a plurality of emitting-auxiliary layers formed between the emitting layer and the hole transport layer, wherein the emitting-auxiliary layer comprises a first emitting-auxiliary layer adjacent to the hole transport layer and a second emitting-auxiliary layer adjacent to the emitting layer, and wherein the first emitting-auxiliary layer comprises the compound of Formula 1.

9. The organic electronic element of claim 4, wherein the organic material layer comprises an emitting layer; a hole transport layer formed between the first electrode and the emitting layer; and a plurality of emitting-auxiliary layers formed between the emitting layer and the hole transport layer, wherein the emitting-auxiliary layer comprises a first emitting-auxiliary layer adjacent to the hole transport layer and a second emitting-auxiliary layer adjacent to the emitting layer, and wherein the second emitting-auxiliary layer comprises the compound of Formula 1.

10. The organic electronic element of claim 4, further comprising a light efficiency enhancing layer formed on at least one surface of the first electrode and the second electrode, the surface being opposite to the organic material layer.

11. The organic electronic element of claim 10, wherein the light efficiency enhancing layer comprises a compound of Formula 1.

12. The organic electronic element of claim 4, wherein the organic material layer comprises 2 or more stacks comprising a hole transport layer, an emitting layer and an electron transport layer sequentially formed on the first electrode.

13. The organic electronic element of claim 12, wherein the organic material layer further comprises a charge generation layer formed between the 2 or more stacks.

14. An electronic device comprising a display device comprising the organic electronic element of claim 4; and a control unit for driving the display device.

15. The electronic device according to claim 14, wherein the organic electronic element is at least one of an OLED, an organic solar cell, an organic photo conductor (OPC), organic transistor (organic TFT) and an element for monochromic or white illumination.

* * * * *